US010426905B2

(12) United States Patent
Vaska et al.

(10) Patent No.: US 10,426,905 B2
(45) Date of Patent: *Oct. 1, 2019

(54) METHODS AND SYSTEMS FOR IMPROVING AIRWAY PATENCY

(71) Applicant: SOMNICS, INC., Zhubei (TW)

(72) Inventors: Matthias Vaska, Palo Alto, CA (US); Jonathan Podmore, San Carlos, CA (US); John Edward Crowe, Menlo Park, CA (US); Sean Christopher Daniel, Palo Alto, CA (US)

(73) Assignee: SOMNICS, INC., Zhubei, Hsinchu County (TW)

( * ) Notice: Subject to any disclaimer, the term of this patent is extended or adjusted under 35 U.S.C. 154(b) by 363 days.

This patent is subject to a terminal disclaimer.

(21) Appl. No.: 15/431,586

(22) Filed: Feb. 13, 2017

(65) Prior Publication Data
US 2017/0151400 A1    Jun. 1, 2017

Related U.S. Application Data

(63) Continuation of application No. 14/626,097, filed on Feb. 19, 2015, now Pat. No. 9,610,190, which is a
(Continued)

(51) Int. Cl.
*A61F 5/56* (2006.01)
*A61M 16/00* (2006.01)
(Continued)

(52) U.S. Cl.
CPC ......... *A61M 16/0009* (2014.02); *A61F 5/566* (2013.01); *A61M 1/0005* (2013.01);
(Continued)

(58) Field of Classification Search
CPC ........ A61F 2/00; A61F 2/20; A61F 2005/563; A61F 5/56; A61F 5/566; A61C 7/08;
(Continued)

(56) References Cited

U.S. PATENT DOCUMENTS 2,560,915 A    7/1951  Bamberger
3,132,647 A    5/1964  Corniello
(Continued)

FOREIGN PATENT DOCUMENTS

EP    1862152 A1    12/2007
JP    2004522483 A    7/2004
(Continued)

OTHER PUBLICATIONS

Cartwright et al., "The effects of a non-surgical treatment for obstructive sleep apnea: the tongue retaining device;" JAMA, Aug. 1982; 248(6):705-709.
(Continued)

*Primary Examiner* — Ophelia A Hawthorne
(74) *Attorney, Agent, or Firm* — Birch, Stewart, Kolasch & Birch, LLP

(57) ABSTRACT

Apparatuses and methods for improving airway patency are provided. A medial surface of the patient's tongue is constrained with a tongue constraint of an oral device placed in the oral cavity to generate a clear region between the medial surface and the hard palate. The clear region is in fluid communication with the soft palate. The tongue constraint has superior surface and inferior surfaces configured to generate the clear region. Negative pressure is applied within the oral cavity to hold the soft palate in a position in which the airway is at least partially open. The negative pressure is applied through one or more ports of the oral device. The one or more ports remain unobstructed by the tongue when the negative pressure is applied. The applied negative pressure causes the soft palate and tongue form a seal whereby the patient's airway is substantially fluidly isolated from the clear region.

31 Claims, 39 Drawing Sheets

Related U.S. Application Data continuation of application No. 13/912,021, filed on Jun. 6, 2013, now abandoned, which is a continuation of application No. 12/882,054, filed on Sep. 14, 2010, now Pat. No. 8,505,540, which is a continuation-in-part of application No. 12/840,076, filed on Jul. 20, 2010, now Pat. No. 8,573,223, and a continuation-in-part of application No. 12/269,683, filed on Nov. 12, 2008, now Pat. No. 8,122,889.

(60) Provisional application No. 60/987,707, filed on Nov. 13, 2007.

(51) Int. Cl.
*A61M 16/04* (2006.01)
*A61M 1/00* (2006.01)
*A61M 16/08* (2006.01)

(52) U.S. Cl.
CPC .... *A61M 16/0463* (2013.01); *A61M 16/0488* (2013.01); *A61M 16/0875* (2013.01); *A61M 2016/0027* (2013.01); *A61M 2205/3331* (2013.01); *A61M 2205/3368* (2013.01); *A61M 2205/502* (2013.01); *A61M 2210/0637* (2013.01); *A61M 2210/0643* (2013.01); *A61M 2230/005* (2013.01); *A61M 2230/205* (2013.01)

(58) Field of Classification Search
CPC ........... A61C 7/00; A61C 7/10; A61C 8/0096; A61C 2201/007; A63B 71/085; A63B 2071/088; A63B 2208/12; A61B 17/663
See application file for complete search history.

(56) References Cited

U.S. PATENT DOCUMENTS

| | | |
|---|---|---|
| 3,566,869 A | 3/1971 | David |
| 3,731,675 A | 5/1973 | Kelly |
| 3,952,743 A | 4/1976 | Harrison |
| 4,164,940 A | 8/1979 | Quinby |
| 4,169,473 A | 10/1979 | Samelson |
| 4,304,227 A | 12/1981 | Samelson |
| 4,669,459 A | 6/1987 | Spiewak et al. |
| 4,676,240 A | 6/1987 | Gardy |
| 4,735,606 A | 4/1988 | Davison |
| 5,018,967 A | 5/1991 | Schwalbach |
| 5,034,006 A | 7/1991 | Hosoda et al. |
| 5,050,616 A | 9/1991 | Wolff et al. |
| 5,104,315 A | 4/1992 | McKinley |
| 5,127,411 A | 7/1992 | Schoolman et al. |
| 5,465,734 A | 11/1995 | Alvarez et al. |
| 5,490,499 A | 2/1996 | Heinonen et al. |
| 5,503,629 A | 4/1996 | Catone et al. |
| 5,513,986 A | 5/1996 | Feltham et al. |
| 5,588,836 A | 12/1996 | Landis et al. |
| 5,738,656 A | 4/1998 | Wagner |
| 5,915,385 A | 6/1999 | Hakimi |
| 5,957,133 A | 9/1999 | Hart |
| 5,989,193 A | 11/1999 | Sullivan |
| 6,454,724 B1 | 9/2002 | Greene |
| 6,467,484 B1 | 10/2002 | De Voss |
| 6,494,209 B2 | 12/2002 | Kulick |
| 6,675,802 B1 | 1/2004 | Thornton |
| 6,679,257 B1 | 1/2004 | Robertson et al. |
| 6,820,617 B2 | 11/2004 | Robertson et al. |
| 6,877,513 B2 | 4/2005 | Scarberry et al. |
| 6,955,172 B2 | 10/2005 | Nelson et al. |
| 6,976,491 B2 | 12/2005 | D'Agosto |
| 6,997,186 B2 | 2/2006 | Robertson et al. |
| 7,073,505 B2 | 7/2006 | Nelson et al. |
| 7,073,506 B2 | 7/2006 | Robertson et al. |
| 7,182,082 B2 | 2/2007 | Hoffrichter |
| 7,328,698 B2 | 2/2008 | Scarberry et al. |
| 7,451,766 B2 | 11/2008 | Miller |
| 7,509,164 B2 | 3/2009 | Jensen et al. |
| 7,935,065 B2 | 5/2011 | Martin et al. |
| 8,074,656 B2 | 12/2011 | Vaska et al. |
| 8,091,554 B2 | 1/2012 | Jiang |
| 8,122,889 B2 * | 2/2012 | Vaska ..................... A61F 5/566 128/848 |
| 8,122,890 B2 | 2/2012 | Vaska |
| 8,505,540 B2 | 8/2013 | Vaska et al. |
| 8,656,922 B2 | 2/2014 | Vaska et al. |
| 8,701,672 B2 | 4/2014 | Vaska |
| 8,979,823 B2 | 3/2015 | Podmore et al. |
| 9,549,795 B2 | 1/2017 | Podmore et al. |
| 9,610,190 B2 | 4/2017 | Vaska et al. |
| 2001/0047805 A1 | 12/2001 | Scarberry et al. |
| 2002/0082544 A1 | 6/2002 | Thrash et al. |
| 2002/0104538 A1 | 8/2002 | Emtell et al. |
| 2005/0037315 A1 | 2/2005 | Inoue et al. |
| 2005/0081859 A1 | 4/2005 | Scarberry et al. |
| 2005/0166928 A1 | 8/2005 | Jiang |
| 2005/0166929 A1 | 8/2005 | Jiang |
| 2005/0236003 A1 | 10/2005 | Meader |
| 2006/0096600 A1 | 5/2006 | Witt et al. |
| 2006/0282010 A1 | 12/2006 | Martin et al. |
| 2007/0184404 A1 | 8/2007 | Johnki |
| 2007/0277818 A1 | 12/2007 | Chen |
| 2008/0092891 A1 | 4/2008 | Cewers |
| 2008/0168989 A1 | 7/2008 | Cewers et al. |
| 2008/0188947 A1 | 8/2008 | Sanders |
| 2008/0200877 A1 | 8/2008 | Panotopoulos |
| 2008/0210244 A1 | 9/2008 | Keropian |
| 2008/0216843 A1 | 9/2008 | Jiang |
| 2008/0308112 A1 | 12/2008 | Aarts |
| 2009/0120446 A1 | 5/2009 | Vaska et al. |
| 2009/0120447 A1 | 5/2009 | Vaska et al. |
| 2009/0123886 A1 | 5/2009 | Vaska |
| 2009/0198201 A1 | 8/2009 | Adahan |
| 2009/0208898 A1 | 8/2009 | Kaplan |
| 2010/0043804 A1 | 2/2010 | Razmovski |
| 2010/0113956 A1 | 5/2010 | Curti et al. |
| 2010/0147302 A1 | 6/2010 | Selvarajan et al. |
| 2010/0288288 A1 | 11/2010 | Hegde et al. |
| 2011/0027748 A1 | 2/2011 | Fusi, II et al. |
| 2011/0220124 A1 | 9/2011 | Vaska et al. |
| 2012/0017917 A1 | 1/2012 | Podmore et al. |
| 2012/0132215 A1 | 5/2012 | Vaska et al. |
| 2012/0132216 A1 | 5/2012 | Vaska |
| 2012/0199135 A1 | 8/2012 | Podmore et al. |
| 2013/0263866 A1 | 10/2013 | Vaska et al. |
| 2015/0157433 A1 | 6/2015 | Podmore et al. |
| 2015/0157492 A1 | 6/2015 | Vaska et al. |
| 2017/0087004 A1 | 3/2017 | Podmore et al. |

FOREIGN PATENT DOCUMENTS

| | | |
|---|---|---|
| JP | 2009502301 A | 1/2009 |
| JP | 2011502715 A | 1/2011 |
| WO | WO-2004021869 A2 | 3/2004 |
| WO | WO-2005074480 A2 | 8/2005 |
| WO | WO-2005082452 A1 | 9/2005 |
| WO | WO-2005092331 A1 | 10/2005 |
| WO | WO-2009064914 A1 | 5/2009 |

OTHER PUBLICATIONS

Office action dated Dec. 3, 2015 for U.S. Appl. No 14/626,097.
Co-pending U.S. Appl. No. 15/431,522, filed Feb. 13, 2017.
Engelke et al., "Preliminary radiographic observations of the tongue-repositioning manoeuvre" Eur. J. of Orthodontics, 2006; 28: 618-623.
European search report and search opinion dated Sep. 8, 2015 for EP Application No. 15168256-4.
European search report dated Oct. 23, 2012 for EP Application No. 08849727.6.
Hoffstein, "Review of oral appliances for treatment of sleep-disordered breathing," Sleep Breath, 2007 Mani 1(1):1-22.

(56) References Cited

OTHER PUBLICATIONS

International Search Report and Written Opinion dated Mar. 17, 2009 for PCT Application No. US2008/083440.
International search report and written opinion dated Jun. 12, 2012 for PCT/US2012/024030.
Notice of allowance dated Feb. 5, 2014 for U.S. Appl. No. 13/368,182.
Notice of allowance dated May 8, 2013 for U.S. Appl. No. 12/882,054.
Notice of allowance dated Sep. 19, 2011 for U.S. Appl. No. 12/269,700.
Notice of allowance dated Oct. 7, 2016 for U.S. Appl. No. 14/624,088.
Notice of allowance dated Oct. 27, 2012 for U.S. Appl. No. 12/269,708.
Notice of allowance dated Nov. 15, 2011 for U.S. Appl. No. 12/269,683.
Notice of allowance dated Nov. 27, 2013 for U.S. Appl. No. 13/365,791.
Notice of allowance dated Nov. 30, 2016 for U.S. Appl. No. 14/626,097.
Notice of allowance dated Dec. 12, 2014 for U.S. Appl. No. 13/023,763.
Office action dated Jan. 15, 2013 for U.S. Appl. No. 12/882,054.
Office action dated Mar. 12, 2013 for U.S. Appl. No. 13/368,182.
Office action dated Mar. 17, 2011 for U.S. Appl. No. 12/269,708.
Office action dated May 18, 2016 for U.S. Appl. No. 14/626,097.
Office action dated May 25, 2011 for U.S. Appl. No. 12/269,700.
Office action dated Jun. 4, 2013 for U.S. Appl. No. 13/365,791.
Office action dated Jun. 20, 2014 for U.S. Appl. No. 13/912,021.
Office action dated Jun. 23, 2014 for U.S. Appl. No. 13/023,763.
Office action dated Jun. 23, 2016 for U.S. Appl. No. 14/624,088.
Office action dated Jul. 26, 2011 for U.S. Appl. No. 12/269,708.
Office action dated Aug. 15, 2013 for U.S. Appl. No. 13/023,763.
Office action dated Aug. 19, 2011 for U.S. Appl. No. 12/269,683.
Office action dated Oct. 10, 2014 for U.S. Appl. No. 13/023,763.
Office action dated Oct. 15, 2012 for U.S. Appl. No. 12/882,054.
Office action dated Oct. 16, 2013 for U.S. Appl. No. 13/023,763.
Office action dated Nov. 21, 2014 for U.S. Appl. No. 13/912,021.
Office action dated Dec. 3, 2013 for U.S. Appl. No. 13/368,182.

* cited by examiner

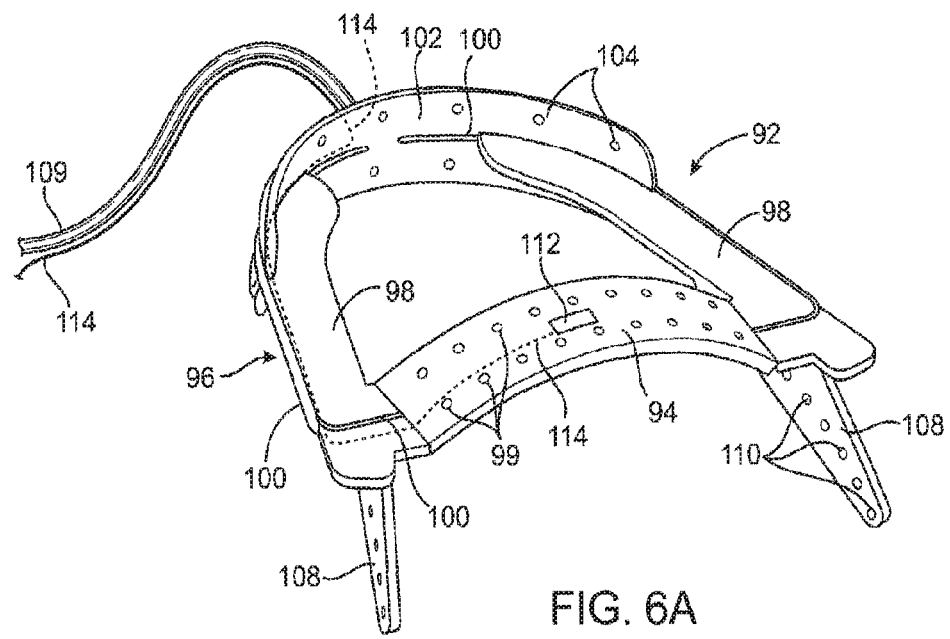
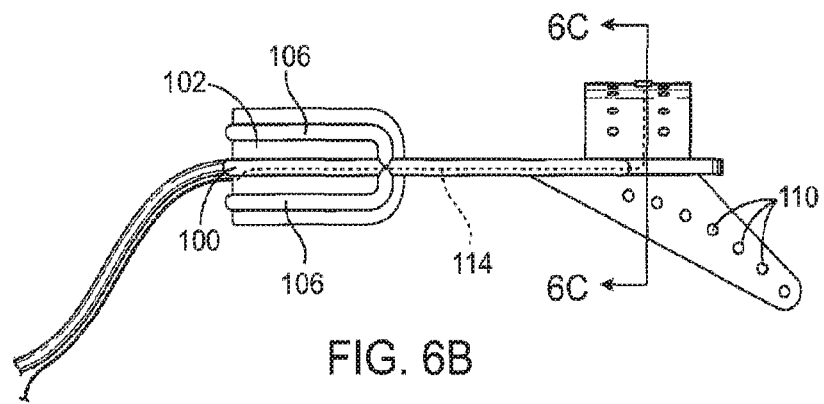
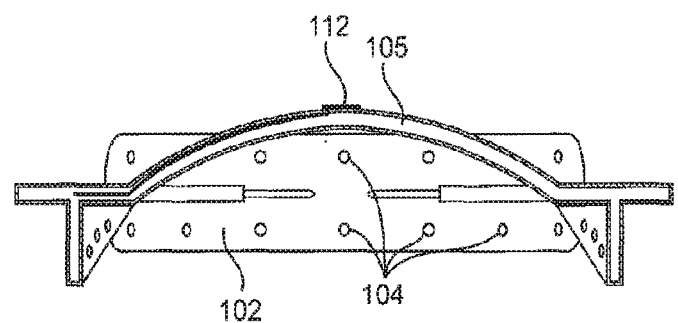

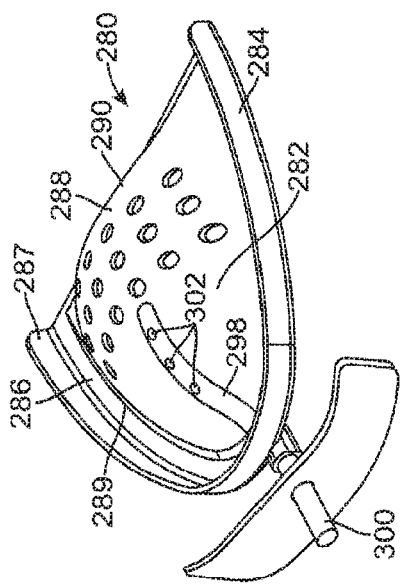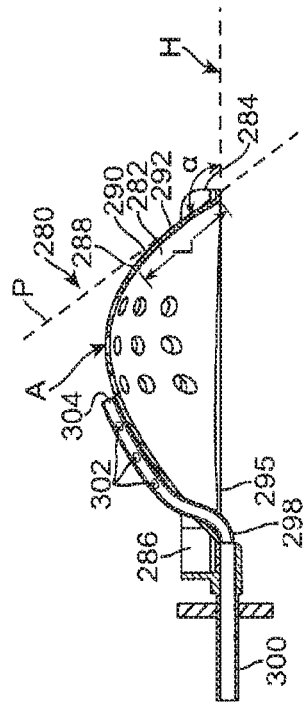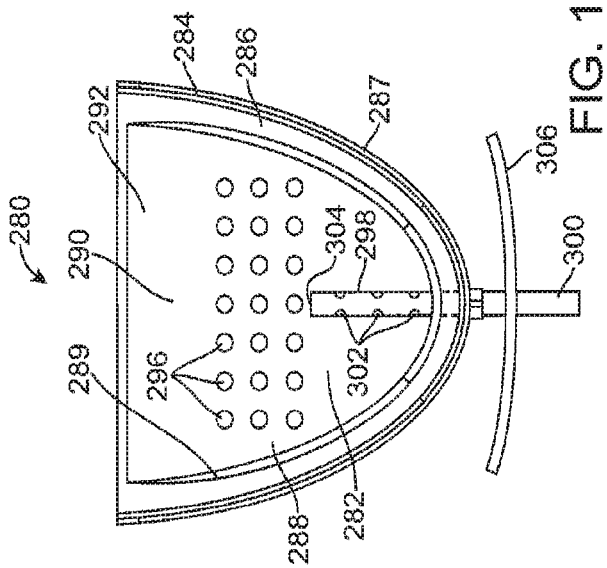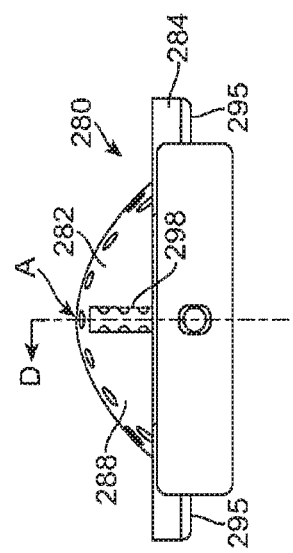
FIG. 14A
FIG. 14B
FIG. 14C
FIG. 14D

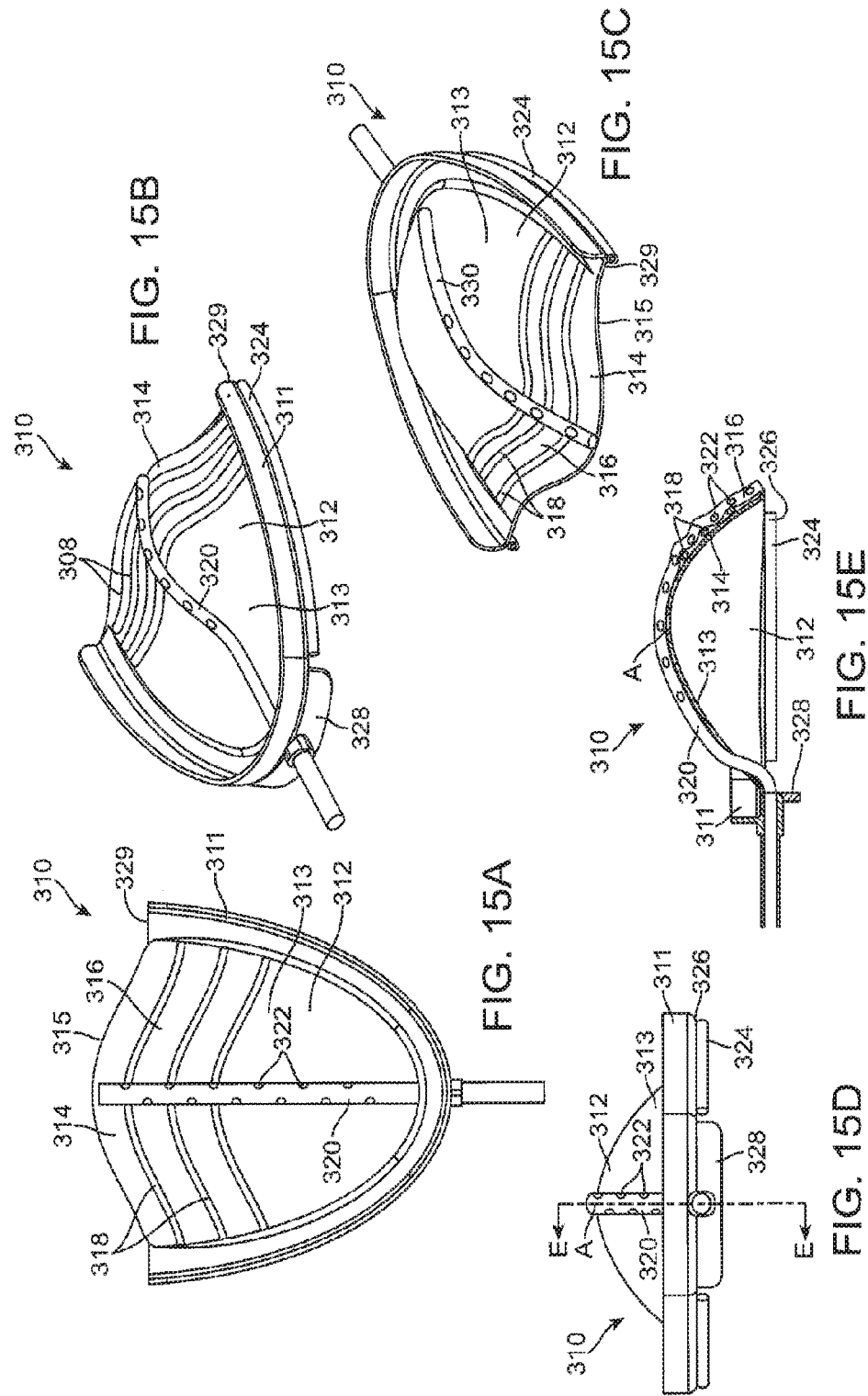

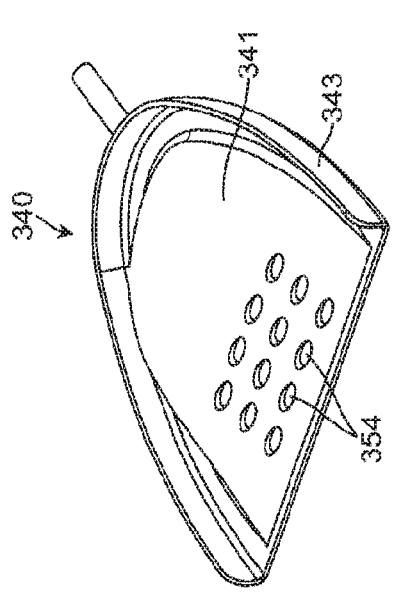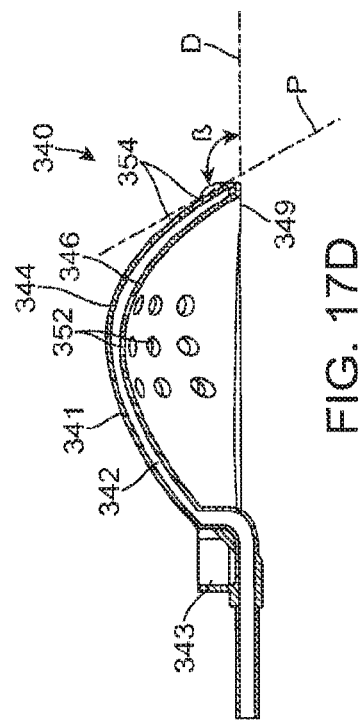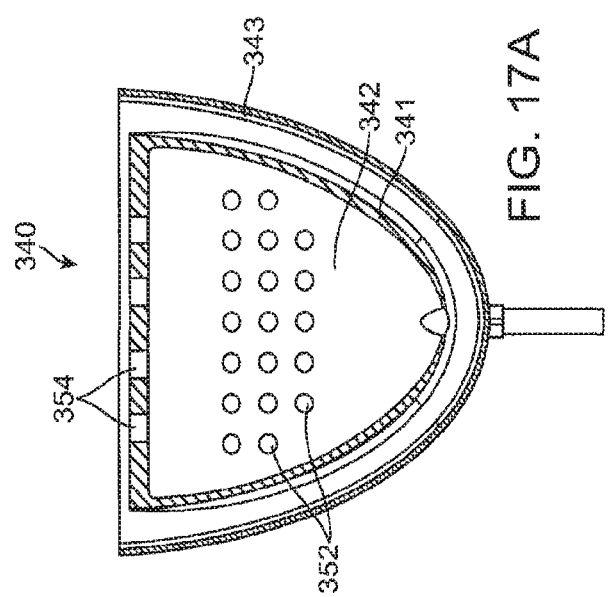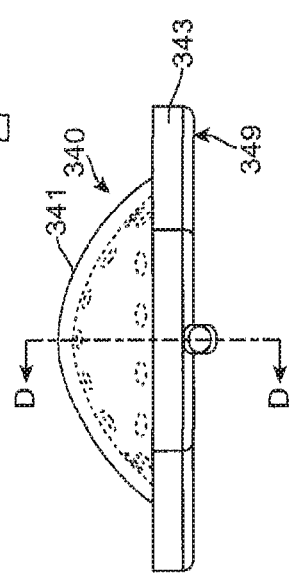
FIG. 17A
FIG. 17B
FIG. 17C
FIG. 17D

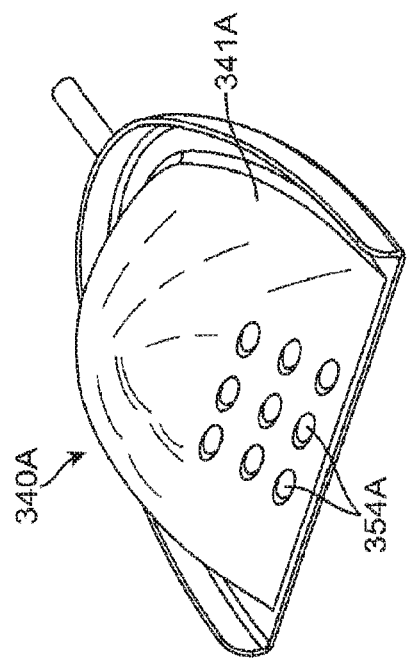
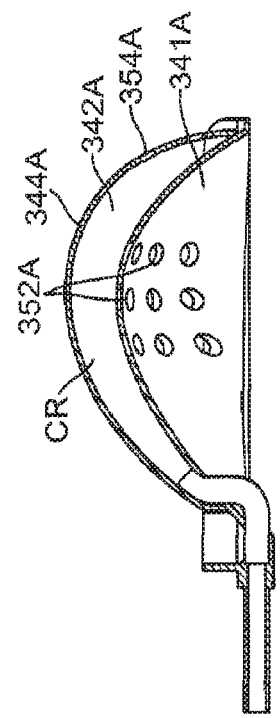
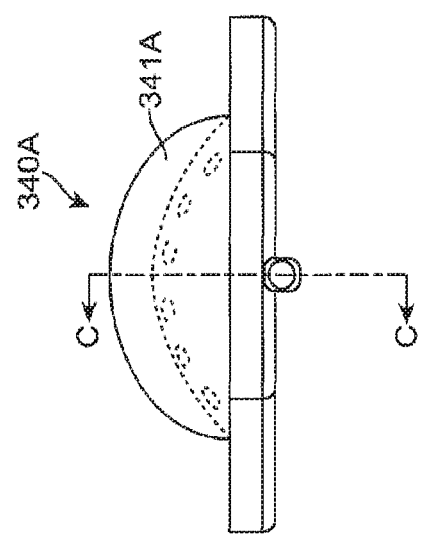

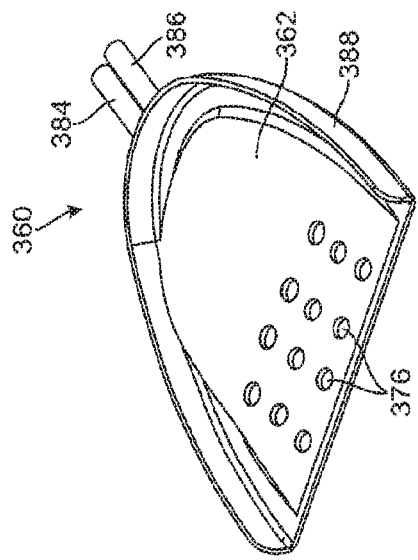
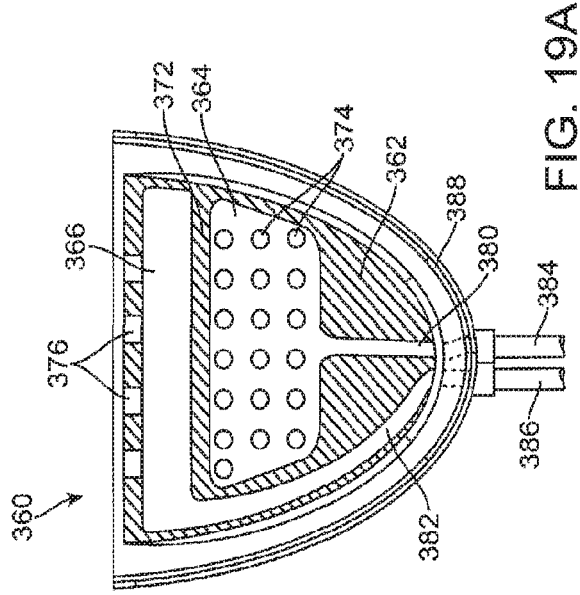
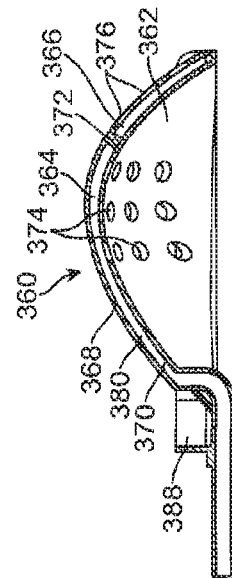
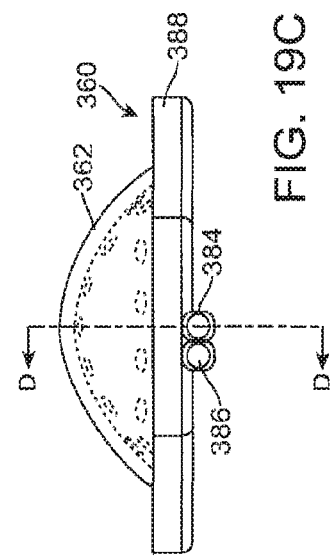
FIG. 19A
FIG. 19B
FIG. 19C
FIG. 19D

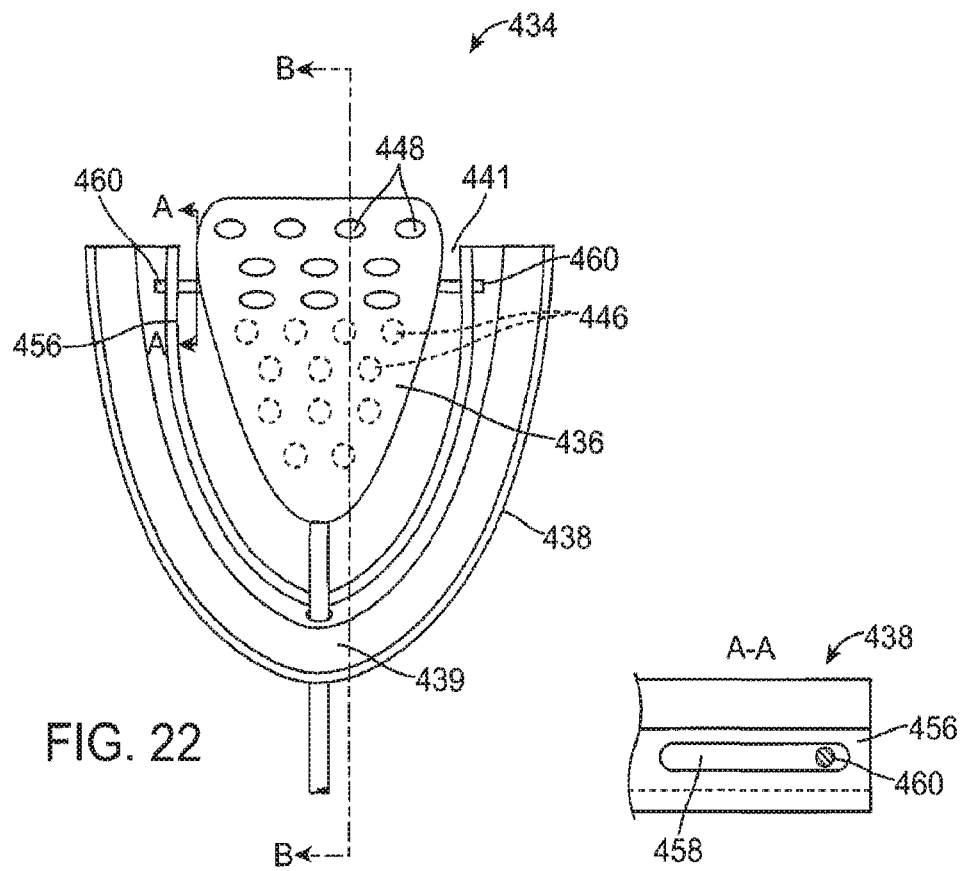
FIG. 22
FIG. 22A
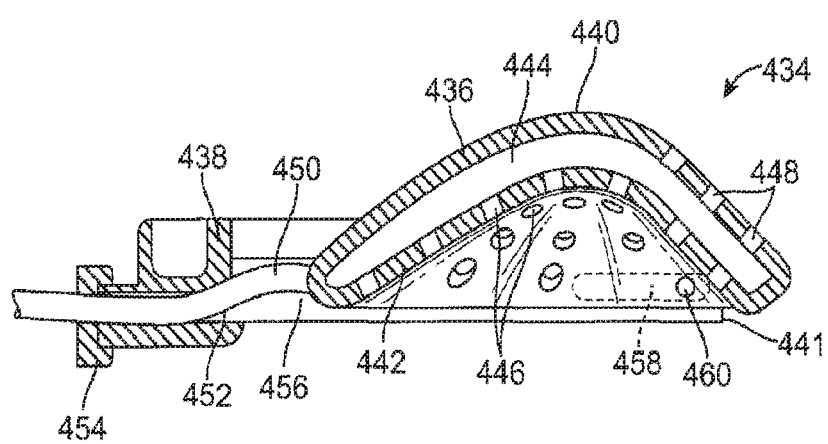
FIG. 22B

METHODS AND SYSTEMS FOR IMPROVING AIRWAY PATENCY

CROSS-REFERENCE

The present application is a continuation of U.S. patent application Ser. No. 14/626,097, filed Feb. 19, 2015, which is a continuation of U.S. patent application Ser. No. 13/912,021, filed Jun. 6, 2013, which is a continuation of U.S. patent application Ser. No. 12/882,054, filed on Sep. 14, 2010, now U.S. Pat. No. 8,505,540, which is a continuation-in-part of U.S. patent application Ser. No. 12/269,683, filed on Nov. 12, 2008, now U.S. Pat. No. 8,122,889, which claims the benefit of U.S. Provisional Application No. 60/987,707, filed Nov. 13, 2007, the full disclosures of which are incorporated herein by reference; U.S. patent application Ser. No. 12/882,054, filed on Sep. 14, 2010, is also a continuation-in-part of U.S. patent application Ser. No. 12/840,076, filed on Jul. 20, 2010, the full disclosures of which are incorporated herein by reference.

BACKGROUND OF THE INVENTION

1. Field of the Invention

The present invention relates generally to medical devices and methods. In particular, the present invention relates to an oral device that may be held in the mouth of a patient to reduce the incidence of obstructive sleep apnea or snoring.

Obstructive sleep apnea (OSA) is a serious medical condition resulting from a temporary airway blockage which occurs as a patient sleeps. The airway blockage usually occurs between the soft palate and/or the back of the tongue and the pharynx. As the patient breathes, the reduced area in the upper airway can cause snoring, and more seriously, OSA.

Sleep disruption caused by OSA can result in severe daytime sleepiness, chronic fatigue, headaches, depression, accidents, injuries, and of particular concern, OSA can reduce the amount of oxygen entering the lungs causing hypoxia. Hypoxia, in turn, can lead to pulmonary hypertension, heart disease, and stroke.

Numerous invasive and less invasive treatments have been proposed for OSA. Of particular interest to the present invention, "continuous positive airway pressure" (CPAP) delivers a continuous stream of pressurized air directly to the person's upper airway. The positive pressure maintains patency of the airway and inhibits the collapse associated with OSA. Although generally effective, CPAP suffers from a number of drawbacks that have led to a high level of non-compliance. The patient must wear a bulky facial mask which can be uncomfortable, and the system generates noise that can make falling asleep difficult. CPAP is also difficult to use because the mask requires careful fitting to avoid air leaks and facial discomfort and because the mask can easily be dislodged during sleep. Moreover, a number of unpleasant side effects, such as sore throats, dry throat and eyes, headaches, and skin rashes from the mask frequently occur. These problems have resulted in a high level of non-compliance with CPAP therapy.

As an improvement over CPAP, it has been proposed to apply a negative pressure to the forward end of the patient's mouth, typically at or just behind the lips, to pull the tongue forward in order to lift the rear portion of the tongue away from the back of the airway. See, for example, U.S. Patent Publication Nos. 2007/0277818, 2005/0166928 and 2005/0166929. While promising in theory, in practice it is very difficult to apply a vacuum in the region of the tip of the tongue to raise the base of the tongue and clear the patient's airway, particularly when the patient is lying on his or her back and gravity is pulling the tongue posteriorly. The tongue is a relatively large and compliant organ with significant mass, and applying a vacuum over a relatively small surface area at the tip will often not be effective in raising the back of the tongue against gravity. The moist and compliant tissues in the mouth are somewhat self-sealing, and this effect tends to inhibit the propagation of negative pressure, thereby confining the negative pressures to a relatively small area near the point of application. Thus, simply applying a vacuum at a location near the anterior tip of the tongue tends to draw the tongue up against the hard palate posterior to this location, creating a seal that restricts the propagation of vacuum through this region of contact toward the back of the oral cavity, where direct vacuum is usually required for maximum effectiveness.

As another improvement over CPAP, it has been proposed to place various devices in direct contact with the posterior tissues of the mouth such as the soft palate and posterior portions of the tongue. A major disadvantage of these approaches is that contact with certain tissues near the posterior area of the tongue may elicit the gag reflex and in any case the presence of such devices so far back in the mouth can be uncomfortable.

For these reasons, it would be desirable to provide alternative and improved methods and apparatus for treating obstructive sleep apnea and snoring. The methods and devices should be non-invasive and require no surgery or permanently implanted components. In addition, the methods and devices should be minimally intrusive with components that are comfortable and quiet so that disruption of the patient's sleep is minimized. Moreover, the methods and devices should avoid contacting the portions of the oral cavity that trigger the gag reflex. The methods and systems should also be simple to implement and be effective to significantly improve patency of a patient's airway during sleep. At least some of these objectives will be met by the inventions described hereinafter.

2. Description of the Background Art

Oral and external devices for treating sleep apnea and snoring are described in U.S. Patent Publication Nos. US2005/166929; US2005/166928; US2008/0188947; US2007/0277818; US2008/0216843; and US2008/0210244; and in U.S. Pat. Nos. 7,182,082; 7,073,506; 7,073,505; 6,955,172; 6,877,513; 6,494,209; 5,957,133; 5,465,734; 4,676,240; 4,304,227; 4,169,473; and 3,132,647; and in Cartwright and Samelson "The effects of a non-surgical treatment for obstructive sleep apnea: the tongue retaining device;" Journal of the American Medical Association 248 (1982).

SUMMARY OF THE INVENTION

The present invention provides methods and systems for improving airway patency in patients by creating a clear region or space above the tongue and applying a negative pressure within the clear region. The clear region creates an opening facing toward the soft palate upon which the negative pressure may act. The negative pressure acts to draw the soft palate away from the pharynx and usually to draw the rear portion of the tongue away from the pharynx as well. The clear region may also serve to create a space into which the soft palate may move while negative pressure continues to act on its free surface. In this way, the soft palate and posterior tongue are urged anteriorly without contacting tissues in a way that might elicit the gag reflex.

By moving the soft palate and optionally the tongue in a forward or anterior direction, the patency of the airway behind the palate and tongue is enhanced to improve breathing. Usually, while the negative pressure is being applied, the patient's lips will be closed or sealed to inhibit the entry of air into the clear region. Additionally, application of the negative pressure will usually draw the soft palate into partial or complete contact with a surface of the rear tongue or with the device itself so as to create a seal which substantially fluidly isolates the airway from the clear region. In that way, the desired negative pressure may be maintained within the clear region with minimum air or fluid flow needed to maintain the negative pressure within the region. Because fluid flow is minimized this therapy can be very quiet and energy-efficient.

As used herein, "superior" refers to the direction toward the top of the oral cavity (or top of the head), "inferior" refers to the direction opposite the superior direction, "anterior" refers to the direction toward the front of the oral cavity or lips, and "posterior" refers to the direction toward the back of the oral cavity and airway, opposite the anterior direction. The terms "patency" and "airway" refer to the opening or clearing of the airway leading from the nasal cavity into the trachea located generally behind the soft palate and the rear of the tongue. To improve airway patency, the airway may be wholly or partially obstructed intermittently or temporarily for some time period over a normal sleep cycle, however, the airway will be open or partially open more than it would in the patient's untreated condition. The "upper portion of the soft palate" refers to the superior portion of the soft palate extending inferiorly from the end which connects to the hard palate to a point about ⅓-½ way toward the free inferior tip of the soft palate. The phrase "medial region" or "medial surface" of the tongue refers to a superior surface of the tongue which is spaced substantially posteriorly from the anterior tip of the patient's tongue and immediately anterior or forward of the region which initiates the gag reflex. While it may vary from patient to patient, the medial region will generally be the middle one third of the upper surface of the tongue which extends between the anterior tip of the tongue and the posterior end of the tongue (the posterior end being the location on the tongue that is furthest posterior in the oral cavity); i.e., the medial surface will usually include an area of the tongue that is at least about ⅓ of the way, more preferably at least about ½ of the way, from the anterior tip of the tongue to the posterior end of the tongue. Preferably, the medial region will include an area on the tongue posterior to the midpoint between the anterior and posterior ends of the hard palate. The phrase "clear region" refers to the space or volume above the tongue which will be cleared by the methods and devices of the present invention. The clearing will usually be achieved by engaging a surface against the superior surface of the tongue, typically using a member or element which engages the tongue and which is anchored within the oral cavity so as to constrain the tongue from raising into the clear region to interrupt the negative pressure which is being maintained. The term "vacuum" and the phrase "negative pressure" each refers to a total or partial vacuum which is maintained in the clear region, typically by controlled aspiration, where the pressure is maintained primarily in the range from 5 cm $H_2O$ to 150 cm $H_2O$ below the local atmospheric pressure. The "occlusal plane" is the plane in which the upper and lower teeth meet when the patient bites the upper and lower teeth together.

In a first specific aspect of the present invention, methods for improving airway patency in a patient comprise constraining a medial surface of the patient's tongue to maintain a clear region below the palate in an oral cavity. Negative pressure is applied within the clear region to open an airway behind the soft palate. Typically, the applied negative pressure closes a posterior portion of the soft palate against the tongue to draw the soft palate forward which in turn opens the airway behind the soft palate. By closing the soft palate against the tongue, the rear of the oral cavity is at least partially sealed so that the negative pressure applied within the clear region can be more easily maintained and can more readily draw both the soft palate tissue and the rear tongue tissue in a forward direction to help open the airway in the pharynx. The front of the oral cavity may also be at least partially sealed in order to inhibit air from entering the mouth. This may be facilitated by providing a sealing structure between the upper and lower lips and/or by providing a sealing structure between the lips and the teeth.

Constraining the medial surface of the patient's tongue may be accomplished in a variety of ways. Typically, a tongue constraint will be engaged against the medial surface to either depress the tongue or maintain the tongue in a lowered or depressed configuration (relative to the roof of the oral cavity) to provide the desired clear region below the palate and above the tongue. Typically, the constraint has a flat or an arch-like structure and may have a generally concave surface which engages the tongue. The tongue will typically be engaged at a point forward of a gag reflex response region, and the negative pressure is applied using a vacuum source positioned proximate the clear region, either within the clear region or adjacent to it. Typically, the vacuum source will have a plurality of ports or openings which permit a distributed aspiration of air and fluids from the clear region within the oral cavity. Often, multiple vacuum sources such as probes, portions of the tongue constraint, or portions of other structures described hereinafter, may be employed to again improve the distribution of the aspiration within the clear region. Usually, the distributed negative pressure or aspiration ports will be positioned within the clear region or adjacent rear portions of the oral cavity in order to assure that the desired negative pressure within the clear region is achieved. This is in contrast to prior art where the vacuum source may be positioned in a forward region of the oral cavity, typically behind the lips, generally in the region of the front teeth. Negative pressure or aspiration ports may also be positioned to apply negative pressure to other posterior portions of the mouth such as the sides of the tongue. Such ports may aid in urging portions of the tongue and soft palate forward by applying negative pressure into posterior oral spaces that can be at least partially sealed off by the compliant tissues of the mouth. It may be advantageous to apply different levels of negative pressure at various locations.

In preferred aspects of these methods for improving airway patency, remaining portions of the tongue will typically not be constrained, and the level of negative pressure applied within the clear region may be adjusted for comfort, to improve efficacy, or for other purposes. In addition, it may be desirable to deliver a fluid, such as water, humidified air, or the like, in order to moisten the oral cavity which might become dry after a prolonged exposure to aspiration. The fluid will typically be delivered during the application of negative pressure, but could also be delivered before, after, and at other times. In other instances, the mouth may be too moist, and fluid such as saliva or mucus will accumulate, in which cases it will be desirable to aspirate fluid which accumulates in the oral cavity, possibly through a separate negative pressure line. Aspiration of accumulated fluid will reduce the need for the patient to swallow during sleep and may be aided by delivery of additional fluid to the oral cavity such as air as described above.

In a second specific aspect of the present invention, methods for improving airway patency comprise positioning an anchor structure in a patient's oral cavity. The anchor structure typically carries or is otherwise coupled to a tongue constraint which engages a medial surface of the patient's tongue to maintain a clear region below the palate. A negative pressure is applied by a vacuum source which is positioned proximate the clear region of the oral cavity, where the negative pressure closes a posterior portion of the soft palate against the tongue to draw the soft palate forward. Often, the at least one vacuum source is coupled to or integral with the anchor structure so that the vacuum source is positioned proximate the clear region when the anchor structure is properly in place. Alternatively, the at least one vacuum source could be positioned separately from the anchor structure, in which case it will typically be formed as a separate probe or other assembly.

The anchor structure may comprise a bite structure which is held by the patient between the patient's teeth. Typically the bite structure will comprise at least one bite surface which is held between the teeth and a lip seal which helps seal the oral cavity when the bite structure is in the mouth. Alternatively, the bite structure may comprise upper and lower tooth-receiving channels which both receive the teeth and help seal the oral cavity when the bite structure is in the mouth. As an alternative to such bite structures, the anchor may comprise a hard palate engagement surface which is held in engagement against the hard palate (the roof of mouth) to hold the anchor in position to maintain the clear region.

The negative pressure may be applied in a variety of ways, usually being applied through a plenum network in the anchor or through a separate vacuum source or probe. Usually, the plenum will be present in the anchor structure, for example extending at least through the tongue constraint. Alternatively or additionally, the plenum could extend through the bite structure, or in other embodiments could be formed separately from the anchor. In still further embodiments, the plenum network will be configured to extend laterally in the oral cavity down at least one side of the tongue, preferably down both sides of the tongue and in a generally posterior direction so that the plenum network can distribute negative pressure to posterior areas of the oral cavity that may otherwise be sealed off by the compliant tissues of the mouth.

In a third specific aspect of the present invention, an oral device comprises an anchor structure having a lip seal. A tongue constraint is coupled to the anchor structure so that the constraint engages a medial surface of the tongue when the lip seal is positioned against the patient's lips. A plenum or other network or means for applying a negative pressure in a region above the medial surface of the tongue is also provided in order to draw the soft palate inferiorly and anteriorly on the posterior region of the tongue when the anchor structure and tongue constraint are in place.

In preferred aspects of the oral device, the lip seal is configured to be positioned between the teeth and the lips, optionally comprising a bite structure, such as a U-shaped frame having a closed forward end and an open rearward end, more typically comprising a pair of bite surfaces which define the U-shaped frame wherein the lip seal is disposed at the closed forward end of the frame. Alternatively, the bite structure may comprise upper and lower tooth-receiving channels, which define the U-shaped frame. The lip seal additionally or alternatively may be configured to be positioned between the upper lip and the lower lip. As an alternative or an addition to the bite structure, the oral device may comprise a hard palate engagement surface. The hard palate engagement surface will be configured to engage the hard palate in order to hold the tongue constraint against the tongue to form the clear region wherein the negative pressure will be applied.

The tongue constraint may also comprise a variety of configurations. Typically, the tongue constraint may be a plate disposed laterally across a rearward portion of the anchor structure. The plate may comprise an arch configured to extend over the tongue and apply a force in the inferior direction.

The negative pressure applying means may also have a wide variety of configurations, but will typically include at least one vacuum port, and usually include a plenum network in any one or more of the anchor structure, tongue constraint, or other portions of the device. In particular, the negative pressure plenum may be present in the tongue constraint, in the bite structure, in the anchor structure, and most often in the tongue constraint which is positioned at the bottom of the clear region where it is desired to draw the negative pressure. The negative pressure plenum could also be formed in a separate structure attached or otherwise coupled to the anchor, and such separate structures will typically extend inferiorly into the oral cavity, more typically on either or both sides of the tongue. Of course, in many cases, it will be desirable to have the plenum formed in the anchor structure, bite structures, tongue constraints, as well as in separate components in order to maximize exposure of the clear region to the negative pressure source. A negative pressure port or plenum may also extend directly to the space lateral to the posterior portion of the tongue in order to further draw the oral tissues away from the airway.

In a fourth aspect of the present invention, systems are provided including an oral device as generally described above in combination with a vacuum source connectable to the negative pressure applying means. The vacuum source will typically comprise a pump, where a flexible tube is provided between the pump and the negative pressure plenum or other means in the oral device. The system may further comprise a pressure sensor present on the oral device and a pressure controller within or connectable to the vacuum source, whereby a desired vacuum level may be maintained within the clear region in the oral cavity. Other specific control and pumping features are described in detail below.

In a fifth aspect of the present invention a method and device are provided which do not require that a clear region be created below the palate in the oral cavity. The device comprises an anchor structure and a means for applying a negative pressure directly to at least one region lateral to a posterior region of the tongue. Any of the various plenum structures which align a vacuum source on either or both sides of the tongue, as described above, would be suitable. Methods comprise applying a negative pressure to at least one region lateral to a posterior portion of the tongue in the oral cavity to open the airway behind the soft palate. Optionally, a clear region below the palate may be opened, and a negative pressure applied therein to enhance opening of the airway.

In a further aspect of the invention, a method for improving airway patency in a patient comprises the steps of placing an oral device in the oral cavity, the oral device having a tongue constraint to engage a medial surface of the tongue, the tongue constraint constraining the medial surface in a position spaced-apart from the hard palate, whereby a continuous vacuum flow path extends from the lips to the soft palate; and applying a vacuum through the vacuum flow path directly to the soft palate such that the soft palate forms a seal against one or both of the tongue and the oral device such that the airway is substantially fluidly isolated from the vacuum flow path.

The tongue constraint will engage and constrain the tongue over an area selected so that the tongue cannot be drawn upward into contact with a posterior portion of the hard palate when the vacuum is applied such that the vacuum flow path becomes obstructed. Because the tongue is soft and compliant, application of vacuum between the tongue and palate will draw the tongue up against the hard palate unless it is physically constrained at the location where a clear region is desired. If not constrained in this manner, this contact between tongue and palate will create a seal that restricts the propagation of vacuum through this region of contact toward the soft palate. Therefore a clear region must be maintained particularly in the region of the soft palate in order to effectively apply vacuum forces to the soft palate. This usually requires that the tongue be engaged in an area substantially posterior to its anterior tip. In most embodiments, the tongue constraint engages the medial surface at a point at least about ⅓ of the distance from an anterior tip of the tongue to a posterior end of the tongue. Preferably, the tongue constraint engages the medial surface at a point posterior to the midpoint between the anterior and posterior ends of the hard palate. The tongue constraint may engage the tongue as far back as 20 mm posterior to the posterior end of the hard palate where it joins to the soft palate. Optionally the tongue constraint may extend anteriorly to or near the front teeth so as to engage the anterior tip of the tongue, but alternatively the tongue constraint may be spaced posteriorly from the front teeth so as to engage only the medial surface of the tongue. Laterally, the tongue constraint will preferably have a shape and size adapted to engage and constrain at least a majority of the width of the tongue. In most embodiments the tongue constraint will span substantially the entire space between the patient's molars. Alternatively the tongue constraint may be configured to engage only a middle portion of the tongue with lateral areas of the tongue remaining unconstrained, or to engage only lateral portions of the tongue with the middle portion unconstrained.

The oral device will mechanically enforce the vacuum flow path to ensure it is continuous from the front of the oral cavity to the soft palate; in some embodiments, the device itself engages tissue along substantially all or a majority of the vacuum flow path to keep it open; in other embodiments, the device engages tissue along a posterior portion of the vacuum flow path, particularly in the medial region of the tongue and posterior thereof, in a manner which maintains the patency of the entire vacuum flow path. Usually the vacuum flow path will comprise a clear region formed between the tongue and the hard palate. Some portions of the tongue may engage the hard palate, however a sufficient portion of the tongue will be spaced-apart from the hard palate so as to create a continuous vacuum flow path from the front of the oral cavity to the soft palate. The clear region is in fluid communication with the soft palate through an opening facing away from the tongue and preferably in a posterior direction toward the soft palate. The vacuum flow path may also comprise a vacuum lumen integral with or coupled to the oral device. Such a vacuum lumen may route the vacuum flow path in a manner that avoids the region between the anterior portion of the tongue and hard palate by routing the vacuum lumen around the outside of the teeth, through the bite line, around the lateral edges of the tongue, or below the tongue. With such configurations, the anterior portion of the tongue may contact the hard palate without affecting vacuum delivery to the soft palate.

The method may further comprise the step of delivering positive pressure to the airway posterior to the seal. Preferably the positive pressure is delivered through the oral cavity, but alternatively could be delivered through the nasal airway.

Vacuum may be applied through a first port oriented away from the tongue such that the first port remains unblocked by the tongue. Preferably, the first port is disposed over or posterior to the medial region of the tongue, preferably being posterior to the midpoint between the anterior and posterior ends of the hard palate. Further, the first port is preferably oriented in a direction so as to apply vacuum directly to an anterior surface of the soft palate. Usually, the soft palate will engage a posterior portion of the oral device when vacuum is applied through the first port. In addition the method may include applying a vacuum to a superior surface of the tongue. The vacuum is usually applied to the superior surface of the tongue through an inferior port in the oral device. Vacuum may also be applied to a lateral surface of the tongue or to other posterior oral tissues. Usually, the vacuum has a negative pressure in the range from −5 cm $H_2O$ to −150 cm $H_2O$.

The method will usually include sealing the patient's lips to inhibit air entering the oral cavity while the vacuum is being applied. The lips may be sealed by placing a sealing structure between the lips and the teeth, between the lips, or on the outside of the lips. The method may further include the step of positioning a pressure monitor in the oral cavity to monitor for leaks.

In addition, saliva may be aspirated from the oral cavity by the vacuum. Preferably the saliva is aspirated so as to minimize any variation in the vacuum pressure applied within the oral cavity. This may be accomplished by the use of a vent in communication with the vacuum flow path. In some embodiments, the method includes maintaining a substantially constant vacuum pressure while the saliva is being aspirated.

The method may optionally include the step of repositioning the patient's jaw into a first position, and maintaining the jaw in the first position while the vacuum is applied. The first position may be a slightly jaw-open position, in which the upper and lower teeth are held slightly apart from each other, or an anterior position in which the lower jaw is held slightly anterior of its normal, relaxed position.

In still another aspect, the invention provides a method for improving airway patency in a patient comprising the steps of constraining a superior surface of the patient's tongue to maintain a clear region between the superior surface and the hard palate, the clear region being in fluid communication with the soft palate through a posterior opening facing in a posterior direction toward the soft palate; and applying a negative pressure within the clear region to hold the soft palate in a position in which airway is at least partially open, wherein the posterior opening remains unobstructed by the tongue when the negative pressure is applied. Using the methods of the invention, the airway may be wholly or partially obstructed for short time periods over a patient's sleep cycle, however, these time periods will be less than in the patient's untreated condition. In a preferred aspect the posterior opening lies in a first plane which is disposed at an angle of at least about 45 degrees, more preferably at least about 90 degrees, relative to an occlusal plane defined by a plane of contact between the patient's upper and lower teeth. In this way, the posterior opening is configured to apply negative pressure directly to at least the upper portion of the soft palate when the airway is unobstructed.

The medial surface of the tongue is usually constrained by a tongue constraint positioned in the patient's oral cavity so as to create the clear region. Usually the tongue constraint engages the medial surface at a point at least about ⅓ of the distance from an anterior tip of the tongue to a posterior end of the tongue. Usually the tongue constraint also engages the medial surface at a point at least ½ the distance from the anterior to the posterior ends of the hard palate. In addition, the tongue constraint will preferably have a shape and size adapted to engage and constrain at least a majority of the width of the tongue. In this way the clear region and the posterior opening are defined on an inferior side by the tongue constraint and on a superior side by the patient's hard or soft palate. The clear region may be in communication with at least one inferior port in the tongue constraint facing toward the tongue such that when negative pressure is applied at least one inferior port is blocked by the tongue while the posterior opening remains unblocked by the tongue. In a preferred aspect of the method, the soft palate engages the tongue, the tongue constraint, and/or another structure coupled to the tongue constraint to create a seal which substantially fluidly isolates the airway from the clear region. Usually the method also includes placing a lip seal along the patient's lips to help seal the oral cavity when the negative pressure is applied.

Negative pressure may be applied through at least one vacuum lumen or plenum network coupled to or integral with the tongue constraint. The vacuum lumen or plenum network may alternatively be coupled to or integral with a bite structure to which the tongue constraint is attached. The plenum network or vacuum lumen may also extend down at least one lateral side of the tongue. Alternatively negative pressure may be applied through at least one vacuum lumen positioned in the oral cavity separately from the tongue constraint.

Usually the method will include positioning an anchor structure in the oral cavity, the tongue constraint being coupled to or integral with the anchor structure. In some embodiments, positioning the anchor structure comprises holding a bite structure between the teeth. Alternatively positioning the anchor structure may comprise engaging a hard palate engagement surface against the hard palate to hold the anchor in position. Preferably, the tongue constraint comprises a plate having a width at least about ½ the width of the tongue. The plate may have lateral edges extending from an anterior to a posterior end thereof, the lateral edges being fixedly attached to the anchor structure.

The method may further include either or both the steps of detecting a leak in the sealed region of the oral cavity with a detector positioned in the oral cavity, or receiving an indication of airway patency from a sensor positioned in the oral cavity. For this purpose, the oral device may include one or more sensors coupled thereto, such sensors comprising pressure sensors, flow sensors, temperature sensors, oximetry sensors, piezoelectric sensors, accelerometers, moisture sensors, contact sensors, or other types of sensors.

In addition the method may include aspirating liquid which accumulates in the oral cavity. Preferably, liquid is aspirated so as to minimize any pressure variation within the oral cavity. In one embodiment, a vent in communication with the vacuum flow path may be used to accelerate clearing of liquid from the vacuum flow path. In such cases the method usually comprises maintaining a substantially constant negative pressure while the liquid is aspirated. Typically the liquid is saliva.

The method may also include a step of delivering positive pressure to the airway while the negative pressure is applied. The positive pressure may be delivered via the oral cavity or via the nasal airway.

In other embodiments the method further comprises repositioning the patient's jaw from an undeflected position to a deflected position, and maintaining the jaw in the deflected position while the negative pressure is applied. The deflected position may be a position anterior to the patient's natural lower jaw position, or a position in which the upper and lower jaws are slightly apart.

In a further aspect, the invention provides a method for improving airway patency in a patient comprising applying a first pressure through a first port at a first location in the patient's oral cavity; and applying a second pressure through a second port at a second location in the patient's oral cavity, the second pressure being different than the first pressure; wherein the tongue and soft palate are held in a position in which airway is at least partially open. Usually at least one of the first and second pressures will be negative pressure.

Usually the first pressure is applied to the tongue through the first port, and the second pressure is applied to the soft palate through the second port. Typically the first and second ports are each coupled to an oral device positionable in the oral cavity. The first and second ports may be movable relative to each other within the oral cavity.

The method may also include constraining the tongue so as to maintain a clear region between the tongue and the hard palate while the first and second pressures are applied. In this case at least one of the first and second ports is usually disposed in a tongue constraint which constrains the tongue. In addition a seal may be created between the soft palate, the tongue and/or a portion of the tongue constraint when the negative pressure is applied such that the airway is substantially fluidly isolated from the first and second ports.

In a particular embodiment at least one of the first and second pressures is positive pressure. The positive pressure may be applied through the first port, the first port being positioned to apply the positive pressure to the airway. Negative pressure may be applied through the second port within the oral cavity while the positive pressure is applied to the airway. The second port is preferably substantially fluidly isolated from the airway after the negative pressure is applied.

In a further aspect of the invention, an apparatus for improving airway patency comprises an oral device positionable in a patient's oral cavity and having a tongue constraint for constraining a medial surface of the patient's tongue in a position spaced apart from the patient's hard palate. In addition, a continuous vacuum flow path is maintained from the patient's lips to the patient's soft palate, the oral device being configured to maintain a seal between the soft palate and one or both of the tongue and the oral device when vacuum is applied through the vacuum flow path such that the airway is substantially fluidly isolated from the vacuum flow path. The oral device will mechanically enforce the vacuum flow path to ensure it is continuous from the front of the oral cavity to the soft palate; in some embodiments, the device itself engages tissue along substantially all or a majority of the vacuum flow path to keep it open; in other embodiments, the device engages tissue at least along a posterior portion of the vacuum flow path, particularly in the medial region of the tongue and posterior thereof, in a manner which maintains the patency of the entire vacuum flow path.

The tongue constraint will engage and constrain the tongue over an area selected so that the tongue cannot be drawn upward into contact with the hard palate when the vacuum is applied such that the vacuum flow path becomes obstructed. This usually requires that the tongue be engaged in an area substantially posterior to its anterior tip. In most embodiments, the tongue constraint engages the medial surface at a point at least about ⅓ of the distance from an anterior tip of the tongue to a posterior end of the tongue. Preferably, the tongue constraint engages the medial surface at a point posterior to the midpoint between the anterior and posterior ends of the hard palate. The tongue constraint may engage the tongue as far back as 20-25 mm posterior to the posterior end of the hard palate where it joins to the soft palate. In addition, the tongue constraint will preferably have a shape and size adapted to engage and constrain at least a majority of the width of the tongue. A posterior portion of the oral device, either part of the tongue constraint or another component, may be configured to engage the soft palate when vacuum is applied. A smooth surface facing toward the soft palate is preferably provided on the posterior side of the oral device which atraumatically engages the soft palate as it is drawn forward by the vacuum.

In preferred embodiments, the vacuum flow path comprises a clear region formed between the tongue and the hard palate. The vacuum flow path may also comprise a vacuum lumen integral with or coupled to the oral device. A delivery lumen may also be coupled to the oral device for delivering positive pressure to the airway. A pressure sensor, oximetry sensor, and/or various other sensors may also be coupled to the oral device. The clear region will be in fluid communication with the soft palate through an opening facing away from the tongue so as to remain unblocked by the tongue when vacuum is applied. Preferably, the opening is disposed over or posterior to the medial region of the tongue, preferably being posterior to the midpoint between the anterior and posterior ends of the hard palate. Further, the opening is preferably facing in a direction generally toward the soft palate so as to apply vacuum directly to the soft palate. The oral device may also include one or more inferior ports in communication with the vacuum flow path and configured to apply vacuum to a superior surface of the tongue, and/or lateral ports configured to apply vacuum to a lateral surface of the tongue and/or other posterior oral tissues.

The apparatus may also include one or more inferior ports in communication with a vacuum lumen fluidly separate from the vacuum flow path, such that vacuum may be exerted on the tongue independently from that exerted on the soft palate.

Usually the apparatus will include a lip seal for sealing the patient's lips to inhibit leaks into the oral cavity. The lip seal may comprise a sealing structure positionable between the lips and the teeth, between the upper and lower lips, or along the lips outside the oral cavity.

The apparatus may include a jaw engagement structure coupled to the oral device adapted to maintain the patient's jaw in a position selected to help keep the airway open. The jaw engagement structure may comprise a tab on the oral device adapted to engage the patient's lower teeth to maintain the lower jaw in an anterior position. The jaw engagement structure may alternatively comprise a spacer disposed on the oral device and positionable between the patient's upper and lower teeth to maintain the jaw in an open position.

The oral device will typically comprise an anchor structure adapted to maintain the position of the oral device within the oral cavity. The anchor structure may comprise a bite structure having channels adapted to receive one or both of the patient's upper or lower teeth. Preferably, the tongue constraint comprises a plate having a width at least about ½ the width of the tongue. The plate may have lateral edges extending from an anterior to a posterior end thereof. In order to provide rigidity to the plate and minimize deflection, at least a posterior portion of the lateral edges are fixed to the anchor structure, usually in the region of the patient's molars. In preferred embodiments, the plate continuously spans substantially the entire distance between the patient's molars, and is fixed on its lateral edges to a bite structure held by the molars.

In yet another aspect of the invention, an oral device for improving patency of a patient's airway comprises a tongue constraint positionable in an oral cavity and adapted to engage a medial surface of a tongue and constrain the medial surface in a position spaced-apart from a hard palate so as to create a clear region therebetween, the clear region being in communication with a soft palate through a posterior opening facing in a posterior direction toward the soft palate; and means for conveying a vacuum to the clear region while the tongue constraint engages the tongue such that the soft palate is held in a position in which the airway is at least partially open, wherein the posterior opening is configured to remain unobstructed by the tongue when the negative pressure is applied. Usually the tongue constraint will constrain the medial surface at a point lying at least about ⅓ of the way from an anterior tip of the tongue to a posterior end of the tongue, and preferably posterior to the midpoint between the anterior and posterior ends of the hard palate. The posterior opening is preferably disposed over or posterior to the medial region of the tongue, preferably being posterior to the midpoint between the anterior and posterior ends of the hard palate.

The posterior opening preferably lies in a first plane which is disposed at an angle of about 45-180 degrees, more preferably about 75-135 degrees in the superior direction relative to the occlusal plane, the occlusal plane being a plane of contact between the patient's lower teeth and the patient's upper teeth when the patient bites the teeth together, or a plane containing the inferior surface of a bite structure on the oral device configured to fit between the upper and lower teeth. With this superior-facing and/or posterior-facing orientation, the posterior opening is configured to apply negative pressure to at least the upper portion of the soft palate when the airway is unobstructed, the upper portion being the superior portion of the soft palate having an upper end joined to the hard palate. The posterior opening may be bounded on an inferior side by the tongue constraint and on a superior side by the patient's hard or soft palate. Alternatively, the posterior opening may lie in a wall of the tongue constraint which is separate from that portion of the tongue constraint that engages the tongue. For example, the tongue constraint may have superior and inferior walls enclosing a hollow interior chamber, wherein the inferior wall engages the tongue and the posterior opening is in the superior wall. Alternatively the tongue constraint may have a plate that engages the tongue, and the posterior opening may be in a posterior wall or landing pad which extends in a superior direction from a posterior edge of the plate and is configured to atraumatically engage the soft palate.

In some embodiments, the clear region is further in communication with at least one inferior port in the tongue constraint facing toward the tongue. The tongue constraint is preferably adapted to maintain the soft palate in engagement with one or both of the tongue and the tongue constraint when vacuum is conveyed to the clear region to create a seal which substantially fluidly isolates the airway from the clear region. Usually, the tongue constraint is configured such that fluid within the clear region is in direct contact with an inferior surface of the hard palate.

The means for conveying the vacuum will typically comprise at least one vacuum lumen coupled to or integral with the tongue constraint. The means for conveying a vacuum may also comprise a plenum network coupled to or integral with the tongue constraint. The vacuum lumen or the plenum network may be formed by one or more hollow regions, passages, or chambers within the tongue constraint or in a bite structure associated therewith. Such a vacuum lumen or plenum network may route the vacuum flow path in a manner that avoids the region between the anterior portion of the tongue and hard palate by routing the vacuum lumen around the outside of the teeth, through the bite line, around the lateral edges of the tongue, or below the tongue. With such configurations, the anterior portion of the tongue may contact the hard palate without affecting vacuum delivery to the soft palate. The vacuum lumen or plenum network may alternatively or additionally extend down at least one lateral side of the tongue.

A pressure lumen may also be coupled to the tongue constraint for delivering fluid under positive pressure to the airway or other regions of the oral cavity. Delivering positive pressure fluid to the oral cavity may facilitate clearance of saliva, while delivering positive pressure air to the airway may improve the pressure gradient that improves airway patency.

The oral device may also comprise an anchor structure coupled to or integral with the tongue constraint. The anchor structure may include a bite structure positionable between the upper and lower teeth, the bite structure typically having tooth-receiving channels which receive the teeth. The anchor structure may alternatively or additionally include a hard palate engagement surface positionable against the hard palate to hold the tongue constraint in position.

The oral device will usually include a lip seal positionable along the patient's lips to help seal the oral cavity when vacuum is applied. The lip seal may be configured for positioning between the lips and teeth within the oral cavity, between the upper and lower lips, or along the outside of the lips external to the oral cavity.

The oral device may further include a pressure sensor coupled to the tongue constraint for monitoring pressure in the oral cavity, an oximetry sensor coupled to the tongue constraint for monitoring the patient's blood oxygen level, or any of a variety of other sensors for monitoring various other conditions.

The oral device may be configured to maintain the patient's upper and/or lower jaws in a desired position other than their normal resting positions. The oral device may comprise a jaw engagement structure coupled to the tongue constraint and adapted to maintain the patient's jaw in a position selected to help keep the airway open. The jaw engagement structure may comprise a tab on the oral device adapted to engage the patient's lower teeth to maintain the lower jaw in an anterior position. The jaw engagement structure may alternatively comprise a spacer disposed on the oral device and positionable between the patient's upper and lower teeth to maintain the jaw in an open position.

A posterior portion of the oral device may be configured to engage the soft palate when vacuum is applied. The posterior portion will usually comprise an atraumatic surface against which the soft palate may be drawn. In a particular embodiment, the oral device may include a soft pad on a posterior surface of the tongue constraint configured to engage the soft palate. A soft pad may also be provided on an inferior surface of the tongue constraint configured to engage the tongue.

In an alternative configuration the tongue constraint is movably coupled to the anchor structure to allow the tongue constraint to move within the oral cavity to reposition the tongue and/or soft palate therein. The tongue constraint may be pivotally coupled, slidably coupled, or otherwise movably coupled to the anchor structure. Preferably the tongue constraint will have vacuum ports in communication with the vacuum applying means to allow the tongue constraint to adhere to the tongue.

The oral device may further include a soft palate landing pad coupled to or integral with the tongue constraint, the soft palate landing pad having a posterior surface adapted to engage the soft palate when the soft palate is in a position in which the airway patency is improved. In some embodiments the soft palate landing pad is movably coupled to the tongue constraint. The soft palate landing pad may also include at least one posterior port adapted to convey a vacuum toward the soft palate. Usually the posterior surface is disposed at an angle of about 45-180 degrees, more preferably about 60-135 degrees relative to an occlusal plane defined by a plane of contact between the patient's upper and lower teeth. In exemplary embodiments, the soft palate landing pad comprises a wall extending superiorly from a posterior edge of the tongue constraint.

In still another aspect of the invention, an apparatus for improving airway patency comprises an oral device positionable in an oral cavity; a first port coupled to or integral with the oral device in a first location; a second port coupled to or integral with the oral device in a second location; means for applying a first pressure through the first port; and means for applying a second pressure through the second port, the second pressure being different than the first pressure; wherein the oral device is configured such that application of the first and second pressures through the first and second ports in the oral cavity holds the tongue and the soft palate in a position in which the airway is at least partially open.

In preferred embodiments the oral device comprises a tongue constraint positionable in the oral cavity and adapted to engage a superior surface of a tongue and constrain at least a portion of the tongue in a position spaced-apart from a posterior portion of the hard palate. In some embodiments the first and second ports are movable relative to each other within the oral cavity. Preferably, the first and second ports are adapted to maintain the soft palate in sealing engagement with the tongue and/or the oral device such that the oral cavity is substantially fluidly isolated from the airway.

The means for applying the first pressure may comprise a first pump and the means for applying the second pressure may comprise a second pump. "Pump" is intended to mean a negative pressure generator, a positive pressure generator, a hand pump, syringe, suction cup, or other means of creating positive or negative pressure. Alternatively, the means for applying the first pressure may comprise a first pump and a first pressure regulator, and the means for applying the second pressure may comprise the first pump and a second pressure regulator.

Usually the second port is configured to apply the second pressure to the soft palate, while the first port is configured to apply the first pressure to the tongue.

The oral device may further comprise an anchor structure adapted to anchor the oral device within the oral cavity. In some embodiments the first port is immovable relative to the anchor structure, while the second port is movable relative the anchor structure. In specific embodiments the second port is disposed in a landing pad movably coupled to the anchor structure.

The means for applying a first pressure may be adapted to apply positive pressure through the first port. In such cases, the first port is usually adapted to apply the positive pressure to the patient's airway. For example, the first port may be disposed in a conduit adapted to extend posteriorly from the oral device into the patient's airway.

In a further aspect, a system according to the invention comprises an oral device positionable in a patient's oral cavity and adapted to create a continuous vacuum flow path from the patient's lips to the patient's soft palate; a vacuum source in fluid communication with the vacuum flow path; and a liquid collector in communication with the vacuum flow path adapted to collect liquid aspirated from the oral cavity.

Usually a conduit such as a tube will be connected between the oral device and the liquid collector. The vacuum source is preferably adapted to maintain substantially the same negative pressure in the vacuum flow path when aspirated liquid is present in the conduit between the vacuum flow path to the vacuum source as when no liquid is present therein. In such embodiments the system will usually include a pressure sensor in communication with the oral cavity. The vacuum source may comprise a pump and a controller, the pressure sensor being coupled to the controller such that the controller regulates the pump in response to signals received from the pressure sensor. The system may also include a pressure tube coupled to the oral device and having a port in communication with the oral cavity, the pressure sensor being in communication with the pressure tube. Alternatively the pressure sensor is attached to the oral device and further comprises a lead coupled thereto for conveying electrical signals from the sensor.

A vacuum tube may be coupled to the oral device in communication with the vacuum flow path, the vacuum tube being in fluid communication with the vacuum source. The weight of any aspirated liquid in the vacuum tube can create pressure offsets depending on the orientation of the tube and the amount of liquid in the tube. In order to facilitate the flow of aspirated liquid to the liquid collector, the system may include a vent in fluid connection with the vacuum flow path preferably in or near the oral cavity. In one embodiment, the vacuum tube has a vent hole therein through which air may flow into the vacuum flow path. In another embodiment, a vent tube may be connected to the oral device or the vacuum tube in communication with the vacuum flow path, the vent tube having an opening to allow the introduction of a small amount of air into the vacuum flow path. By using this venting technique to clear the liquid, the pressure-offsetting effects of liquid present in the vacuum tube will be minimized.

The liquid collector preferably comprises an airtight space having an inlet and an outlet, the vacuum tube being connected to the inlet, the outlet being fluidly connected to the vacuum source. The liquid collector collects the aspirated liquid in the airtight space up to a maximum level, and the inlet and the outlet are usually separated from the maximum level by a liquid-free space. The vacuum is thereby conveyed from the outlet to the inlet through the liquid-free space.

The oral device usually comprises a tongue constraint adapted to maintain at least a medial portion of the tongue in a position spaced apart from the patient's hard palate so as to maintain a clear region therebetween. Preferably the oral device is adapted to maintain the soft palate in sealing engagement with the tongue and/or the oral device so that airway is more patent and substantially fluidly isolated from the vacuum flow path.

In yet another aspect, a system according to the invention comprises an oral device positionable in a patient's oral cavity and adapted to maintain a continuous vacuum flow path from the patient's lips to the patient's soft palate and substantially seal the patient's airway from the vacuum flow path; a vacuum source in fluid communication with the vacuum flow path; and a sensor for detecting at least one condition within the oral cavity.

In a preferred embodiment, the system will further include a controller coupled to the sensor and the vacuum source for controlling the vacuum source in response to signals generated by the sensor. In one embodiment the sensor comprises a pressure sensor and the controller is adapted to automatically regulate the vacuum source so as to maintain a substantially constant negative pressure in the oral cavity. Alternatively, pressure readings from the pressure sensor are used to regulate the vacuum source so as to maintain the pressure in the oral cavity at one or more desired levels.

The system may further include a recording device coupled to the sensor and adapted to record data received from the sensor over a time period. The recording device may comprise a memory device such as a read-only memory device, random-access memory device, or removable memory device such as an optical disk or flash drive. Usually the system will further include a computer in communication with the memory device, a display adapted to display information from the memory device to the user and a user input device adapted to transmit information from the user to the computer. Preferably, the time period is selectable by the user to be any of a plurality of times periods.

In most embodiments the sensor is attached to the oral device so as to be positionable in the oral cavity. In other embodiments the system further includes a tube attached to the oral device and having a port located in the oral cavity when the oral device is positioned therein, the sensor being in communication with the tube outside the oral cavity.

The sensor may comprise a pressure sensor adapted to detect pressure in the patient's oral cavity, an oximetry sensor adapted to detect oxygen levels in the oral cavity or in the patient's blood or tissue, an impedance sensor adapted to detect contact between the oral device and tissues in the oral cavity, an accelerometer adapted to detect the orientation of the patient's head, a piezoelectric sensor for detecting a sound selected from breathing, snoring, teeth grinding, or heartbeat, a moisture sensor to detect moisture in the oral cavity, a flow sensor for detecting air flows or leaks in the oral cavity, or a temperature sensor. In one configuration the temperature sensor is adapted to detect the temperature of air in or adjacent to the airway. For example, the temperature sensor may be mounted to the oral device so that when the oral device is in place, the sensor is positioned just below the nostrils so as to sense air temperature just outside the nasal airway, allowing the patient's rate of breathing to be monitored. The system may further include at least a second sensor for monitoring a second condition in the oral cavity. The second sensor is preferably coupled to the oral device along with the first sensor.

The system may further include a transmission device for electronically transmitting information from the recording device to an external device. The transmission device may be a modem, a docking station, a cable connector, a wireless transmitter, or other type of data transmission device.

Preferably, the oral device is adapted to maintain the soft palate in sealing engagement with the tongue and/or the oral device such that the airway is substantially fluidly isolated from the vacuum flow path. In such cases the sensor may be adapted to monitor whether the airway is fluidly isolated from the vacuum flow path. For example the sensor may be a pressure sensor for monitoring pressure in the oral cavity, or a flow sensor for monitoring flow rate through the vacuum flow path.

The system may further include an alarm adapted to provide a visual or audible signal in response to data received from the sensor. For example, if pressure or oxygen level in the oral cavity is at an undesirable level, the system may provide an audible alarm to wake the patient and/or notify them that a change is required, e.g. ensuring the oral device is positioned properly, repositioning the patient's head, etc.

Additionally, the system may include a liquid collector in communication with the vacuum source for collecting liquid aspirated from the oral cavity. Usually a vent will be provided in communication with the vacuum flow path in or near the oral cavity so as to allow the introduction of a small amount of air into the vacuum flow path such that aspirated liquid moves quickly from the vacuum flow path to the liquid collector. Preferably, the vacuum source is adapted to automatically maintain a desired level of negative pressure in the oral cavity as liquid is being aspirated. In such embodiments the sensor may comprise a pressure sensor for monitoring pressure in the oral cavity.

A further understanding of the nature and advantages of the invention may be gained by reference to the following detailed description taken in conjunction with the drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 3A is a perspective view, FIG. 3B is a top view, and FIG. 3C is a bottom view.

FIGS. 6A-6C illustrate a fifth embodiment of an oral device constructed in accordance with the principles of the present invention, where FIG. 6A is a perspective view, FIG. 6B is a side view, and FIG. 6C is a cross-sectional view taken along line 6C-6C of FIG. 6B.

FIG. 6D is a side cross-sectional view and FIG. 6E is a sectional view taken along line 6E-6E in FIG. 6D.

FIG. 7A is a perspective view, FIG. 7B is a side view, and FIG. 7C is a cross-sectional view taken along line 7C-7C in FIG. 7B.

FIG. 8A is a perspective view, FIG. 8B is a detailed view of an adjustable tongue constraint, FIG. 8C is a side view of the device, and FIG. 8D is a cross-sectional view taken along lines 8D-8D of FIGS. 8A and 8C.

FIG. 10A is a perspective view, FIG. 10B is a top view, and FIG. 10C is a cross-sectional view taken along line 10C-10C of FIG. 10B.

FIG. 13A illustrates the manual vacuum generator attached to the oral device of FIG. 4, with FIG. 13B showing the device in use with a saliva collector, and FIG. 13C showing the internal components of the device.

FIGS. 14A-14D are top, oblique, front and side cross-sectional views, respectively of an oral device according to the invention in a further embodiment thereof.

FIGS. 15A-E are top, front oblique, rear oblique, front, and side cross-sectional views, respectively, of an oral device according to the invention still another embodiment thereof, in which the lip seal is removed for clarity.

FIGS. 17A-17D are top cutaway, oblique, front, and side cross-sectional views, respectively of an oral device according to the invention in still another embodiment thereof, in which the lip seal is removed for clarity.

FIGS. 18A-18C are oblique, front, and side cross-sectional views, respectively of an oral device according to the invention in still another embodiment thereof, in which the lip seal is removed for clarity.

FIGS. 19A-19D are top cutaway, oblique, front and side cross-sectional views, respectively, of an oral device according to the invention in still another embodiment thereof, in which the lip seal is removed for clarity.

FIGS. 22 and 22B are top and side cross-sectional views, respectively of an oral device according to the invention in still another embodiment thereof, in which the lip seal is removed for clarity.

FIG. 22A is a side partial cross-section taken along line A-A in FIG. 22.

DETAILED DESCRIPTION OF THE INVENTION

Figure 1:
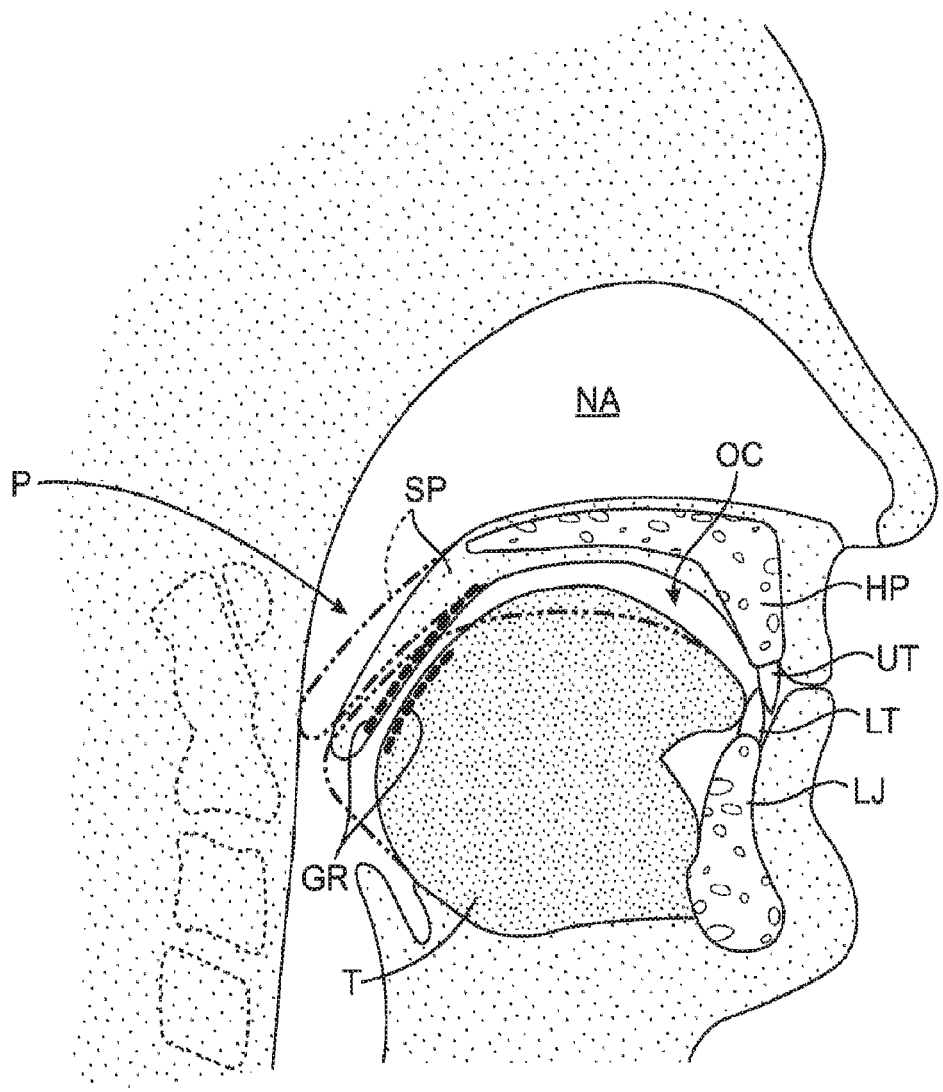
FIG. 1 illustrates the relevant anatomy of the nasal and oral cavities.

Referring to FIG. 1, the anatomy of the oral and nasal cavities relevant to obstructive sleep apnea (OSA) and the placement of the devices of the present invention will be described. The upper teeth UT of the patient are anchored in the hard palate HP, and the lower teeth LT are anchored in the lower jaw or mandible LJ. The soft palate SP extends in a rearward or posterior and inferior direction from the hard palate, and together the hard palate and soft palate divide the nasal airway NA from the oral cavity OC. The lower extent of the oral cavity is largely defined by the upper surface of the tongue T in this view, and it will be appreciated that both the soft palate SP and the tongue are mobile structures capable of movement between the positions shown in full line and broken line in FIG. 1. A nasal airway NA extends inferiorly into the pharynx P which defines the airway generally behind the soft palate SP and the tongue T. The regions on the tongue and soft palate shown with a heavy dashed line are the areas responsible for the gag reflex GR.

Obstructive sleep apnea occurs when the soft palate, the tongue or both move in a posterior direction so that they contact the rear or posterior surface of the pharynx P. The posterior motion of the soft palate and/or tongue may also reduce the size of the airway without contacting the pharynx P causing a partial blockage. The temporary blockage of the airway behind the soft palate and tongue will cause the disrupted breathing pattern characteristic of OSA and usually associated with snoring.

Figure 2A:
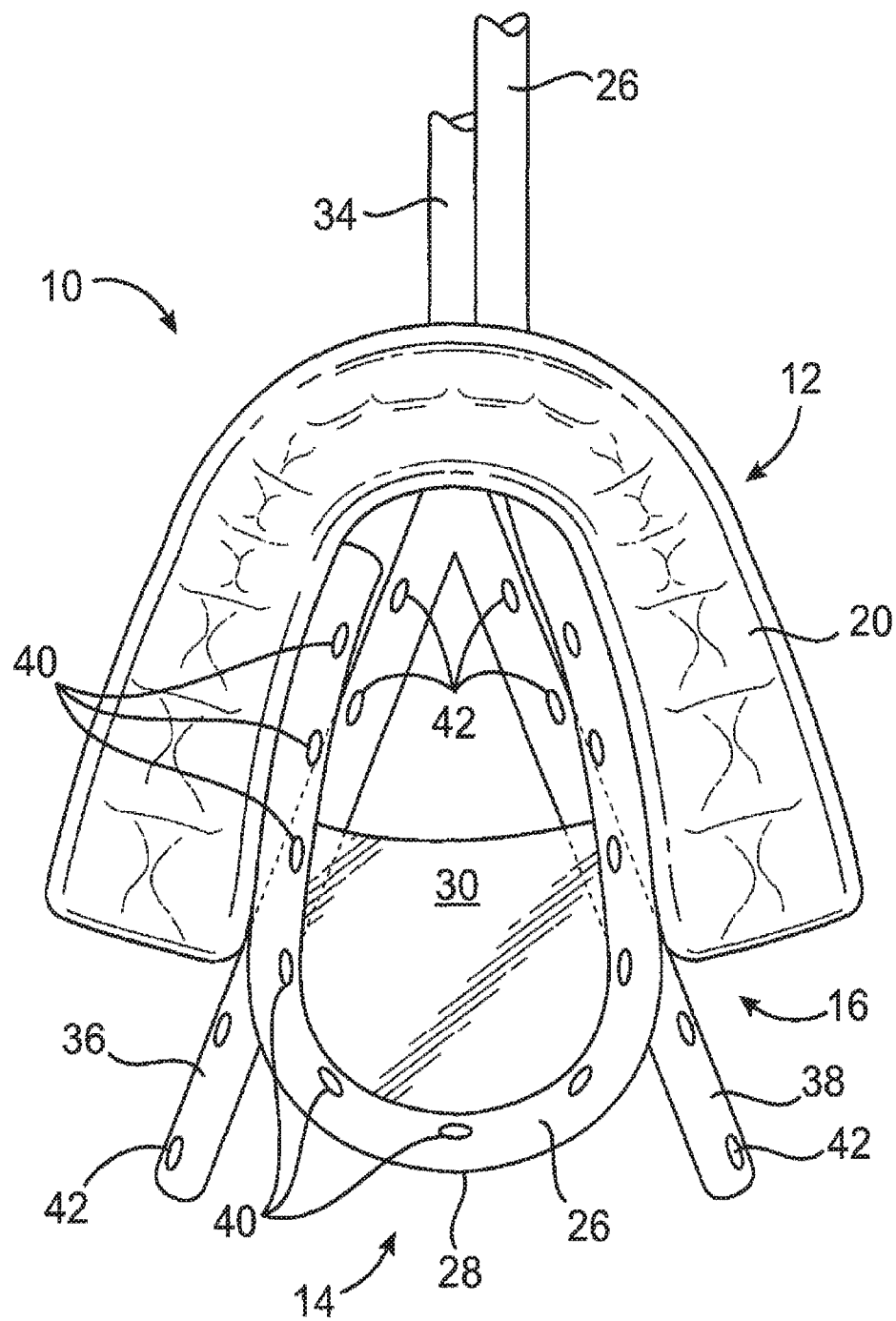
FIG. 2A illustrates a first embodiment of an oral device constructed in accordance with the principles of the present invention.
Figure 2B:
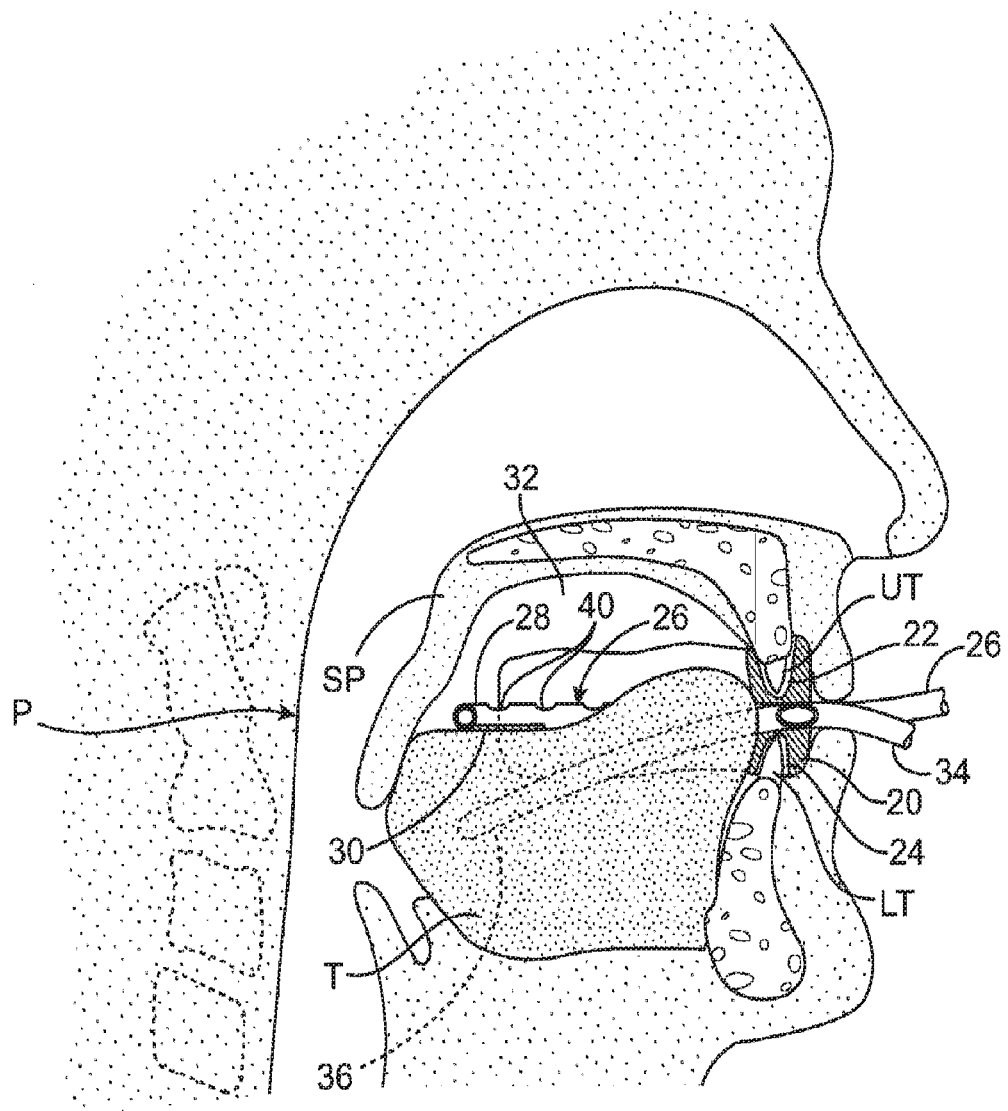
FIG. 2B illustrates use of the device of FIG. 2A for inhibition of OSA when placed in an oral cavity of a patient.

Referring now to FIGS. 2A and 2B, a first exemplary oral device 10 constructed in accordance with the principles of the present invention comprises an anchor structure 12, a tongue constraint 14, and a plenum structure 16 adapted to aspirate the oral cavity and apply a negative pressure therein while the anchor structure is held in the patient's mouth. The anchor structure 12 includes a bite structure 20 having upper and lower tooth-receiving channels 22 and 24, respectively, as best seen in FIG. 2B. The portions of upper and lower tooth-receiving channels 22 and 24 that contact the lips help to create a seal which inhibits entry of air into the oral cavity. The tongue constraint 14 comprises a J-shaped tube 26 which passes through or is otherwise coupled to the anchor structure 20 so that a posterior end 28 of the tube lies over a posterior end of the medial region of the tongue, as best seen in FIG. 2B. Optionally, the tongue constraint 14 may further include a tongue retraction plate 30 which extends over the medial region of the tongue to help constrain the tongue inferiorly to create a clear or open region 32 over the tongue and beneath the soft palate, as best seen in FIG. 2B.

The plenum structure 16 is partly formed within the J-shaped tube 26 of the tongue constraint and partly provided by a separate lateral tongue vacuum tube 34. The vacuum tube 34 has a Y-shaped geometry with legs 36 and 38 extending laterally and generally inferiorly on either side of the tongue. Legs 36 and 38 serve to create negative pressure in portions of the oral cavity that may otherwise be sealed off by the compliant mouth tissues, thereby helping to urge the tongue and soft palate forward. Both the J-shaped tube 26 and the tongue vacuum tube 34 have a plurality of vacuum ports 40 and 42, respectively, distributed along their lengths. Typically, the tubes 26 and 34 will have inside lumen diameters in the range from 0.5 mm to 5 mm, with ports having widths in the range from 0.5 mm to 10 mm, often having an oval shape as illustrated, but optionally having other shapes. By having multiple points spaced throughout the oral cavity, particularly within the posterior region of the oral cavity, the ability to provide a continuous aspiration to maintain the desired level of negative pressure or vacuum is greatly enhanced. It will be appreciated that even if certain ones of the vacuum ports 40 and 42 become blocked, others will remain open to expose the clear region created by the tongue retraction plate 30 to the desired pressure. As can be seen in FIG. 2B, vacuum tube 26, plenum structure 16, and clear region 32 provide a continuous vacuum flow path from the patient's lips to the soft palate through which vacuum may be applied. By applying the desired vacuum or negative pressure, the soft palate SP will be drawn inferiorly and anteriorly against the posterior region of the tongue T, generally forming a seal which substantially fluidly isolates the airway from the vacuum flow path and permits the negative pressure to draw the soft palate and tongue anteriorly to open up the airway behind the soft palate and tongue adjacent the pharynx P.

Figure 3A:
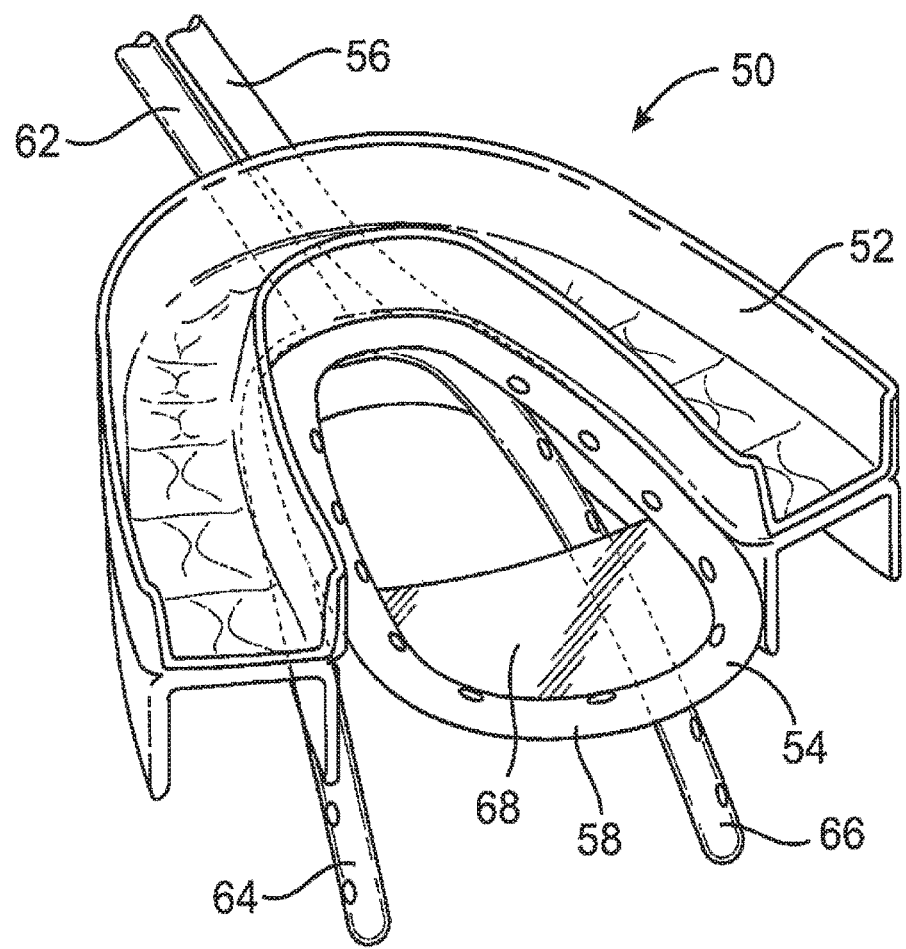
FIGS. 3A-3C illustrate a second embodiment of an oral device constructed in accordance with the principles of the present invention, where
Figure 3B:
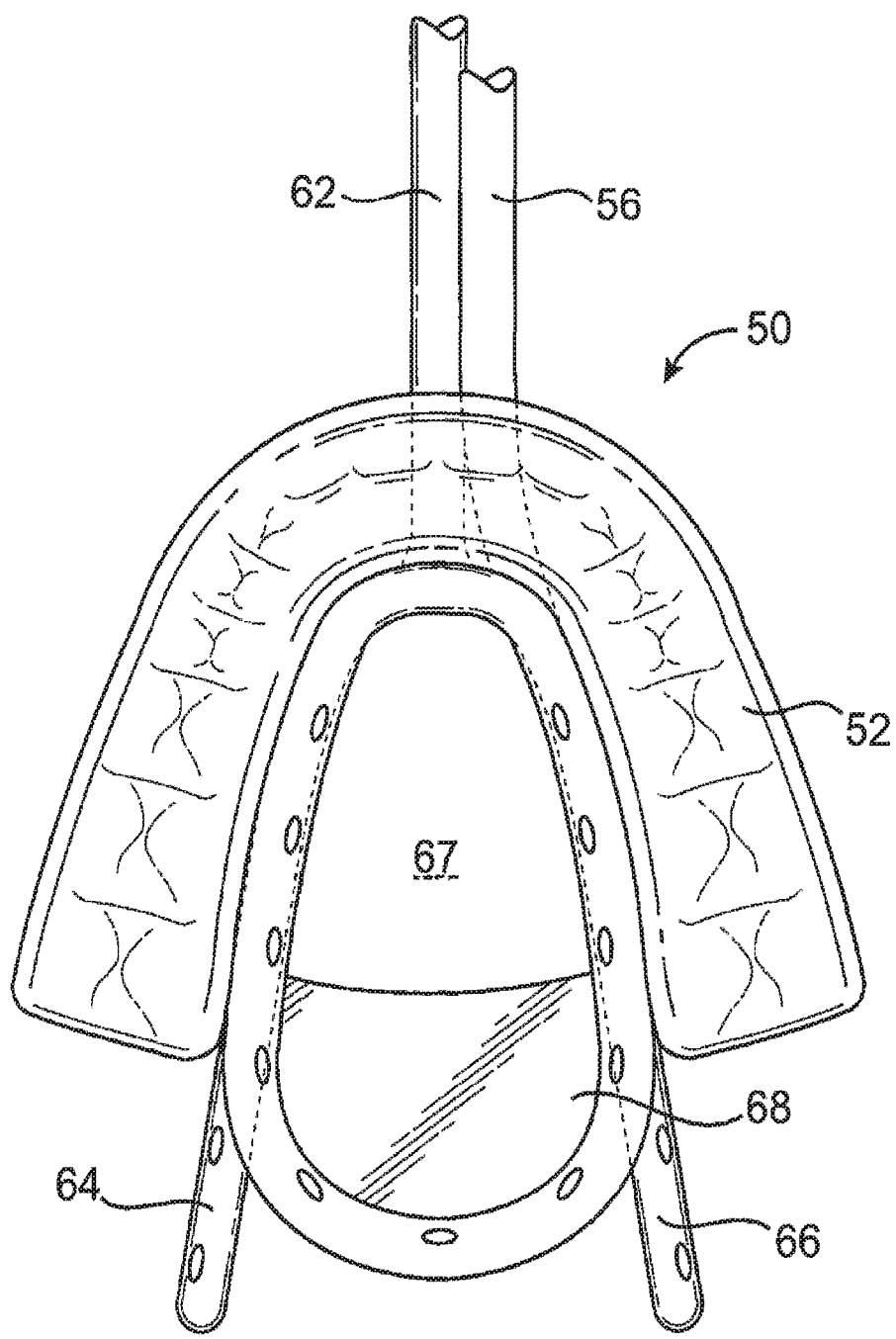
Figure 3C:
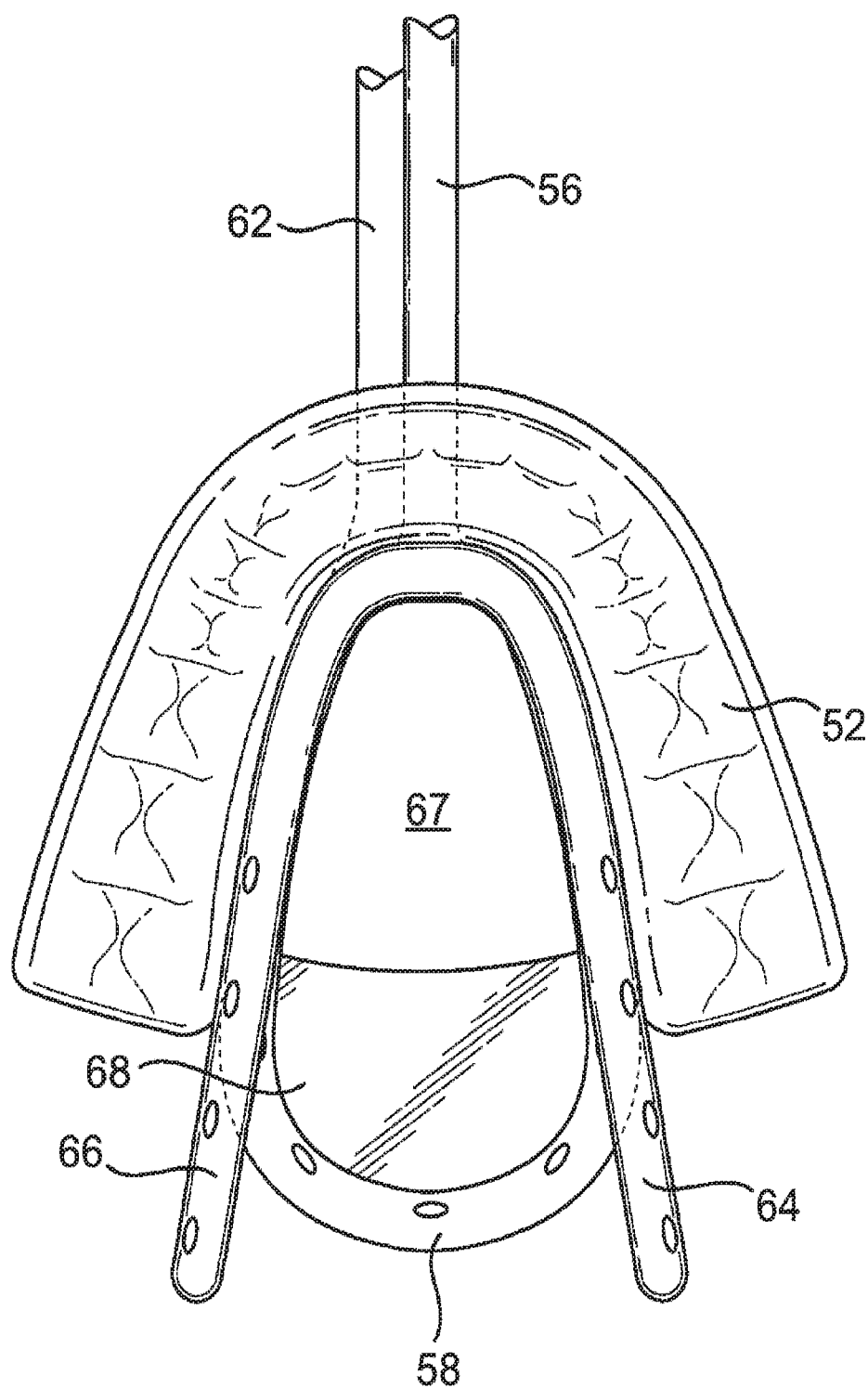

Referring now to FIGS. 3A-3C, a second exemplary embodiment of the oral device 50 will be described. The oral device 50 includes generally the same components as the oral device 10 with an anchor structure 52 being generally identical to the anchor structure 12. A tongue constraint 54 is similar to tongue constraint 14, except that it is formed from a tube 56 having an oval tubular structure 58 at its proximal end. The oval tube 58 allows the vacuum or negative pressure connection to extend through both sides of the tube, rather than terminating at one end, as with the J-shaped tube 26 of device 10. This provides for more robust operation by allowing negative pressure to be applied even if the lumen of oval tube 58 becomes clogged. Oral device 50 also includes a plenum structure comprising a tube 62 with inferiorly oriented arms 64 and 66 which is generally similar to the lateral vacuum tube structure 34 of oral device 10. The arms 64 and 66, however, are curved rather than straight as in the earlier embodiment. Oral device 50 generally provides for more open space 67 on the anterior side of the tongue retraction plate 68.

Figure 4:
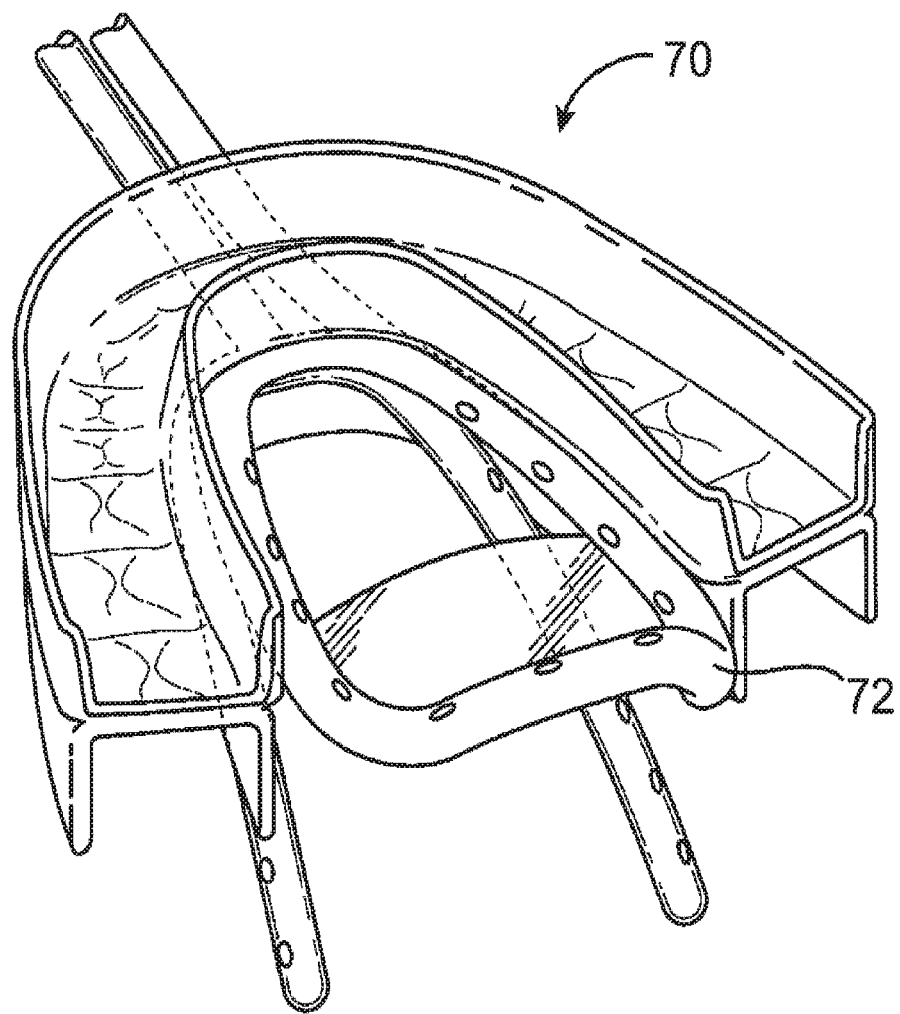
FIG. 4 is a perspective view of a third embodiment of an oral device constructed in accordance with the principles of the present invention.

FIG. 4 is a further variation of an oral device 70 which is almost identical to device 50, except that a tongue constraint structure 72 has an arcuate or curved lateral cross section in contrast to the straight cross section of tongue constraints 54 and 14 in oral devices 50 and 10, respectively. The arcuate shape of the tongue constraint structure 72 may improve the comfort of the device by allowing for a more natural tongue position. The palate and the tongue naturally take on a similar domed shape.

Figure 5:
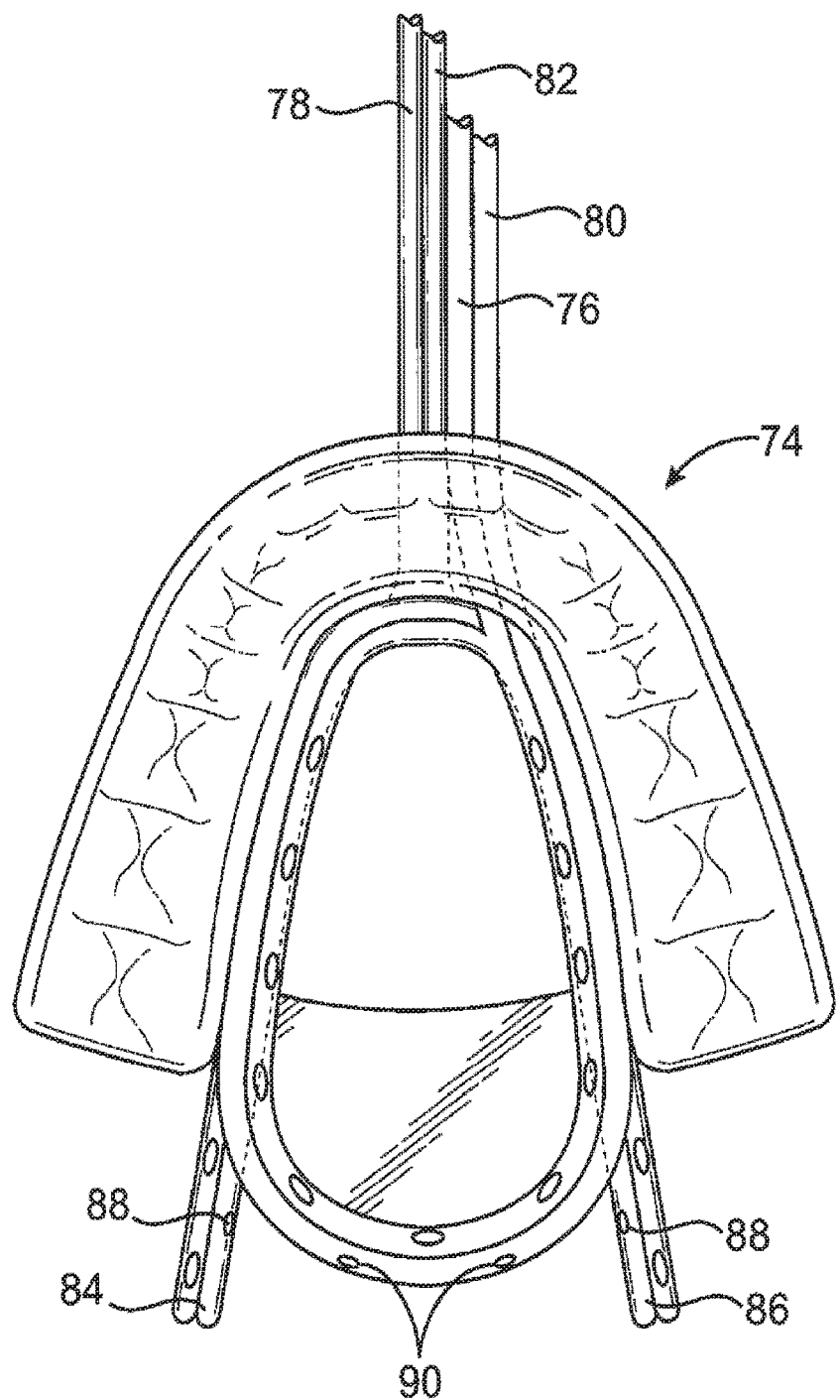
FIG. 5 is a top view of a fourth embodiment of an oral device constructed in accordance with the principles of the present invention.
Figure 6D:
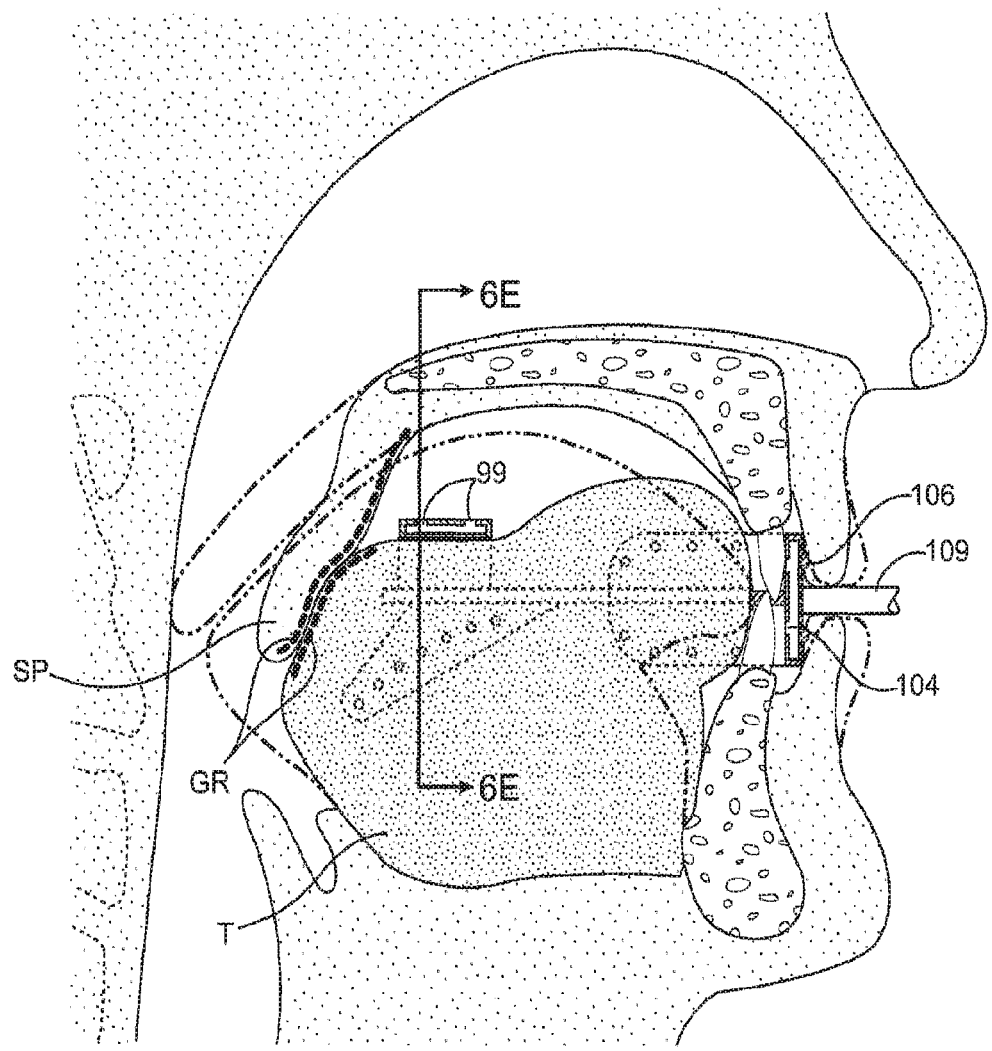
FIGS. 6D and 6E illustrate use of the device of FIGS. 6A-6C for inhibiting OSA when placed in an oral cavity of a patient, where
Figure 6E:
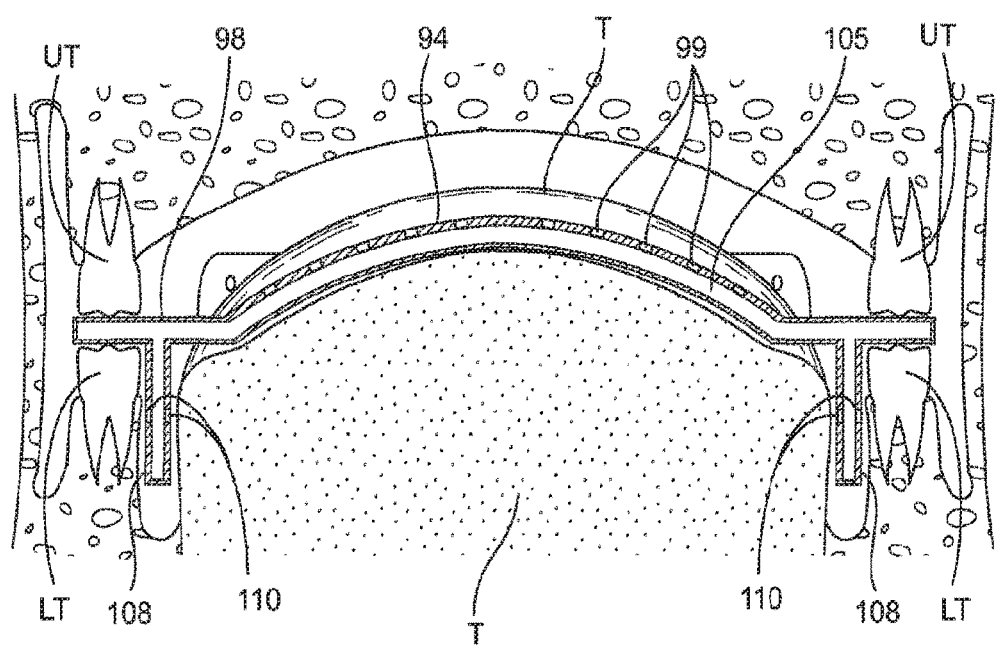

FIG. 5 is a further variation of an oral device 74 which is almost identical to device 50 with tube 76 being generally identical to tube 56 and tube 78 generally being identical to tube 62. Oral device 74 also includes tubes 80 and 82 which generally follow the paths of tubes 76 and 78, respectively. Tube 82 bifurcates into arms 84 and 86 in a similar manner as arms 64 and 66. Ports 88 and 90 are in fluid communication with tubes 82 and 80, respectively. Tubes 80 and 82 can be thereby be used to monitor the negative pressure in the oral cavity at the locations of ports 88 and 90 by connecting tubes 80 and 82 to pressure sensors. In addition fluids such as humid air or warmed saline may be introduced via tubes 80 and 82 and ports 88 and 90 in order to enhance patient comfort by moistening the oral cavity or by helping to aspirate fluids such as saliva that may have collected in the oral cavity.

Referring now to FIGS. 6A-6E, a third exemplary embodiment of the oral device 92 will be described. The oral device 92 generally provides similar components as the oral device 70. An anchor structure 96 includes bite structure 98 which is configured to be held between the patient's upper and lower teeth. Bite structure 98 does not include tooth-receiving channels and is open at the front allowing the front teeth to overlap, thus improving patient comfort by minimizing the bulk of the device and allowing the mouth to close more than oral device 70 allows. Instead of relying on tubes to convey the negative pressure, tongue constraint structure 94 is hollow and includes one or more vacuum ports 99, thereby reducing the overall size and bulk of the tongue constraint structure. Portions of bite structure 98 may be hollow and used to convey the negative pressure. A tubular structure 100 may additionally be employed to convey the negative pressure. A lip seal structure 102 facilitates creating a seal at the mouth by contacting the inner surface of the lips proximate the mouth opening. The lip seal structure 102 may also be hollow in order to convey negative pressure to vacuum ports 104 which are positioned to help ensure that negative pressure is well-distributed proximate the lips, thus providing for improved lip sealing forces. One or more lateral tongue structures 108 may be flexible and also hollow in order to convey negative pressure to vacuum ports 110 which are positioned to enhance the distribution of negative pressure into the oral spaces lateral to the tongue. A vacuum plenum 105 may thusly comprise contiguous hollow portions of lip seal structure 102, tubular structure 100, bite structure 98, tongue constraint structure 94, lateral tongue structures 108, and a vacuum tube 109 that is connected to a source of negative pressure. Optionally, lip seal protrusion 106 may enhance the formation of a seal at the lips by concentrating lip contact forces at the protrusion. Optionally, a sensor 112 such as a pressure sensor with connecting cable 114 may be mounted on tongue constraint structure 94 or on any other part of the device for example to monitor the pressures developed in the oral cavity.

Figure 7A:
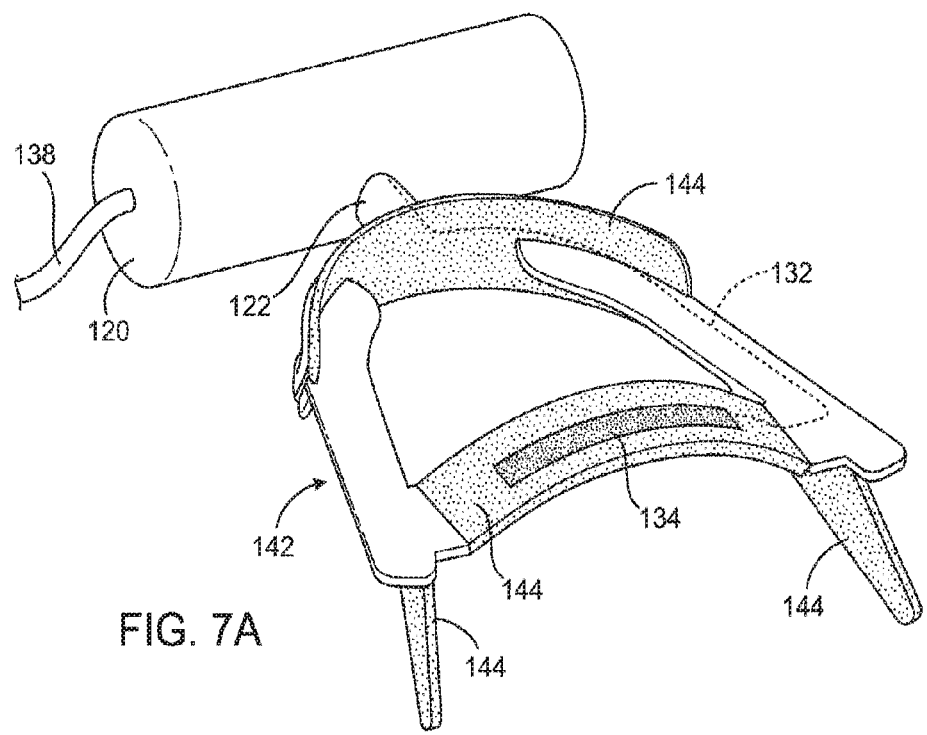
FIGS. 7A-7C illustrate a sixth embodiment of an oral device constructed in accordance with the principles of the present invention, where
Figure 7B:
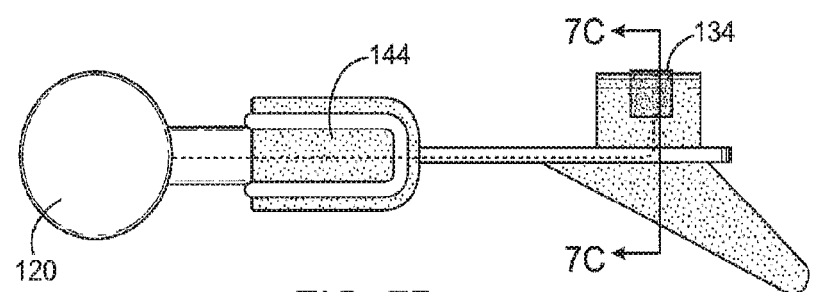
Figure 7C:
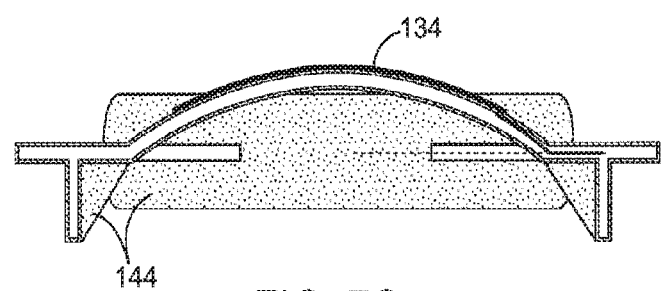
Figure 7D:
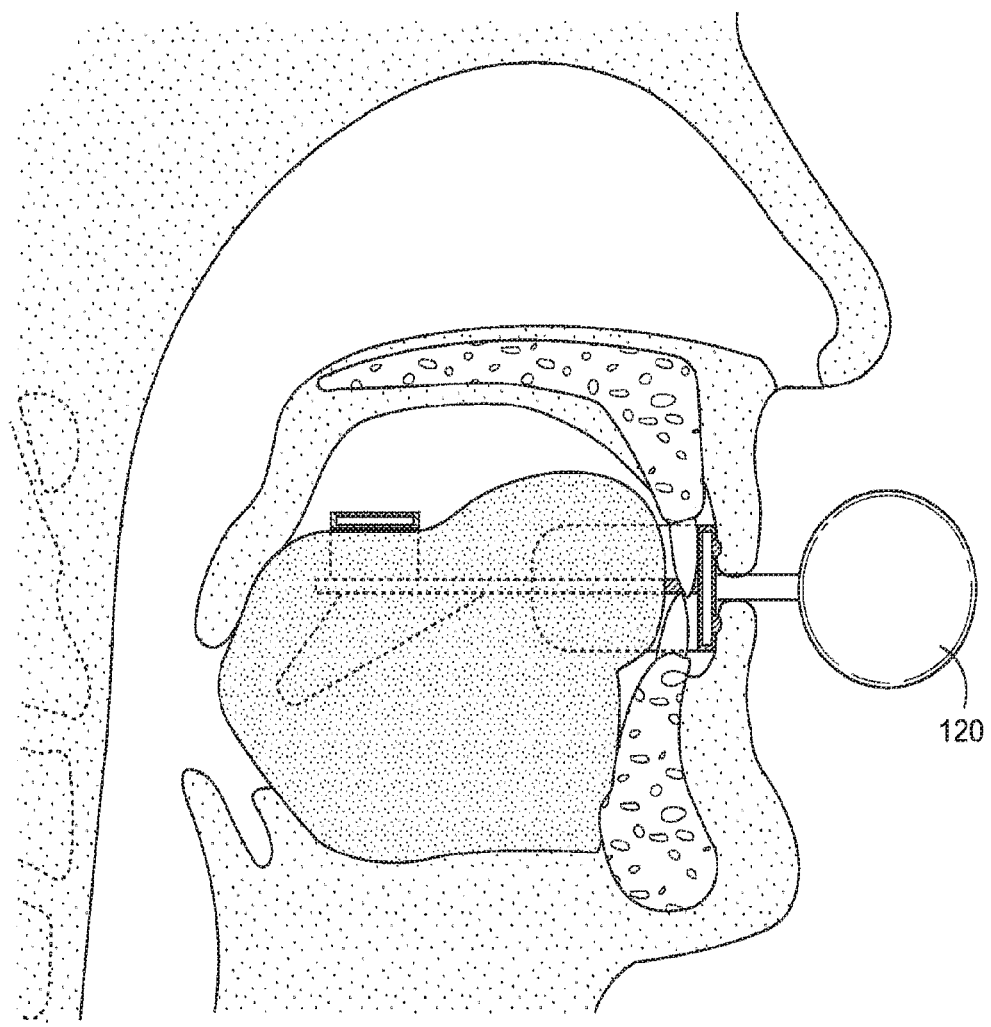
FIGS. 7D-7F illustrate use of the device of FIG. 7A-7C for inhibiting OSA when placed in the oral cavity of a patient.
Figure 7F:
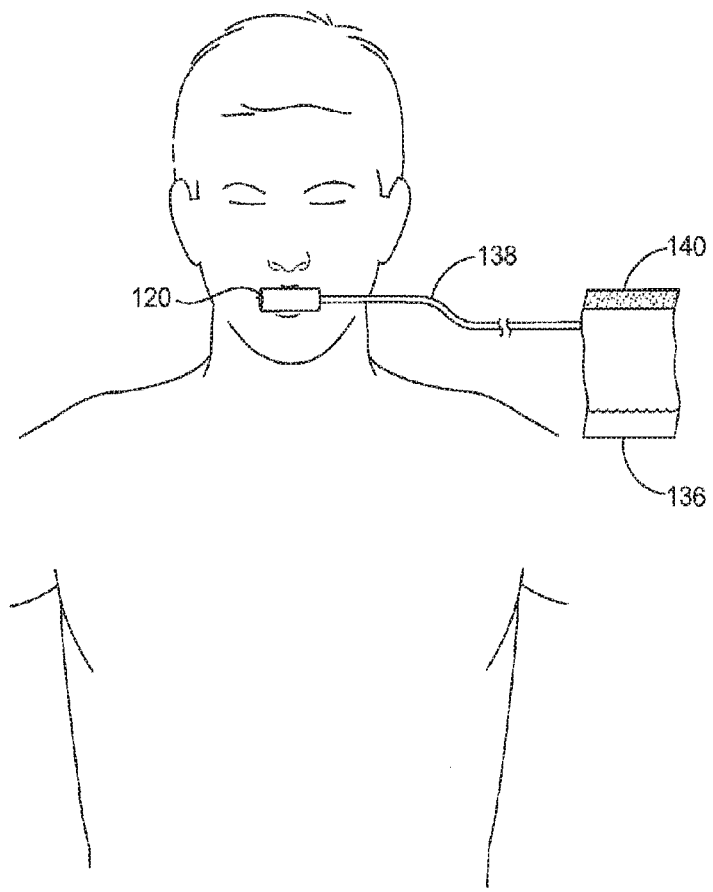
Figure 7E:
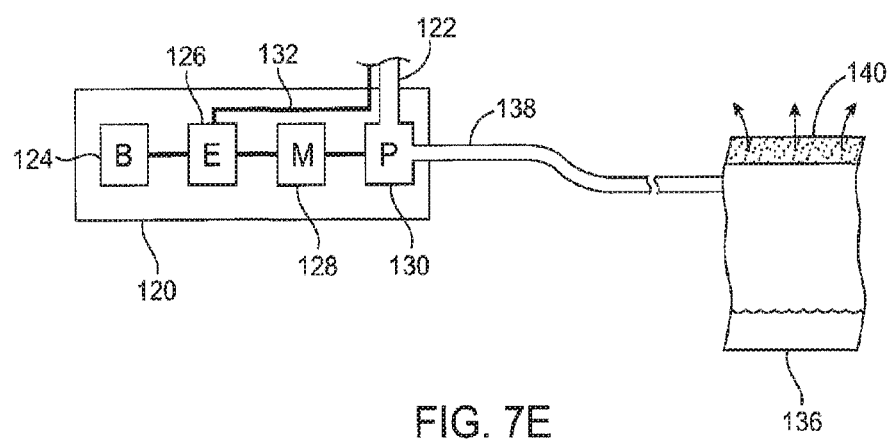

Referring now to FIGS. 7A-7F, an oral device 142 that employs a portable vacuum source 120 which can be used with the vacuum plenum of any of the oral devices described is illustrated. Portable vacuum source 120 includes a connection port or tube 122 which can be connected to the vacuum plenums of any of the previously or subsequently described oral devices. The portable vacuum source 120 includes battery 124, control electronics 126, a motor 128, and a pump 130, as best seen in FIG. 7E. Connector line 132 may be provided to allow the electronics 126 to be connected to sensors or other components on the oral device. For example, the oral device may be provided with an electric heater 134 to provide warmth that may improve patient comfort. Optionally, saliva collection reservoir 136 may be connected to the portable vacuum source 120 by a flexible connecting tube 138, as best seen in FIG. 7F. The saliva collection reservoir 136 will have a porous cover 140 which will allow air to bleed while retaining the saliva in the reservoir. Instead of the discrete vacuum ports that are employed in the previously described oral devices, oral device 142 employs a porous material 144 such as porous polyethylene to distribute the negative pressure into the oral cavity. Porous material 144 has small pores which act to filter out particulates that could collect and clog the vacuum tubes. Porous material 144 also has a large number of pores and a large surface area of pores which help to maximize the spatial extent of negative pressure within the oral cavity.

Figure 8A:
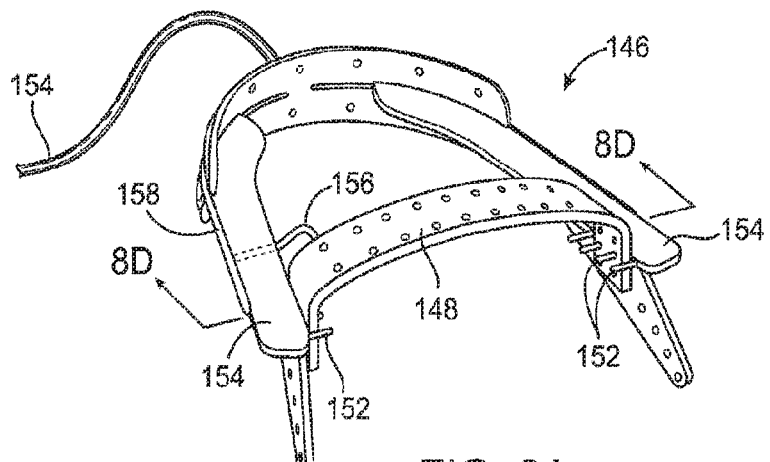
FIGS. 8A-8D illustrate a seventh embodiment of an oral device constructed in accordance with the principles of the present invention, where
Figure 8B:
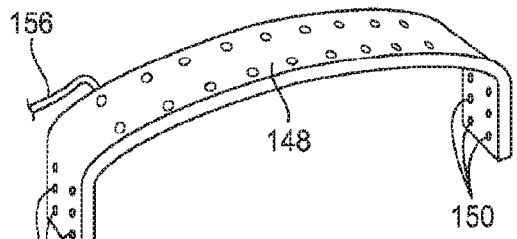
Figure 8C:
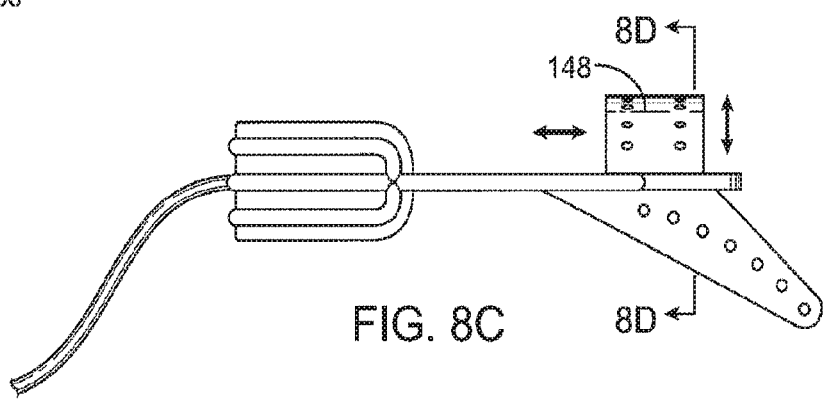
Figure 8D:
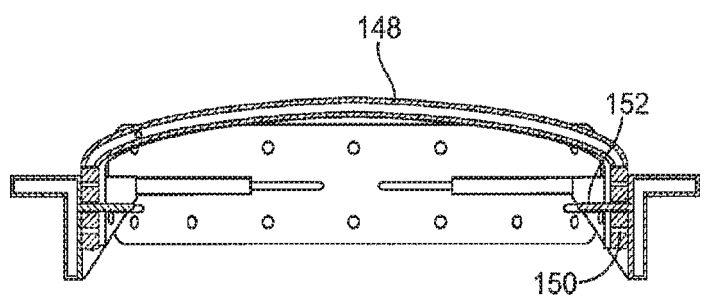

Referring now to FIGS. 8A-8D, an oral device 146 which is very similar to oral device 92 except that it employs an adjustable tongue constraint structure 148 which can be used with any of the oral devices described is illustrated. Adjustable tongue constraint structure 148 has three pairs of through holes 150 at each side. Each pair of through holes 150 may be engaged with a pair of the four protrusions 152 which extend from each of the bite structures 154. It can be appreciated that adjustable tongue constraint structure 148 may be moved superiorly, inferiorly, anteriorly, and posteriorly by engaging various pairs of holes 150 with appropriate pairs of protrusions 152 as best shown in FIG. 8A. Such adjustability facilitates the fitting of oral device 146 to the anatomy of a particular patient. Adjustable tongue constraint structure 148 is hollow and is connected to vacuum tube 154 by means of flexible tube 156 and tubular structure 158. Bite structures 154 may also be hollow in order to convey negative pressure as with oral device 92.

Figure 9A:
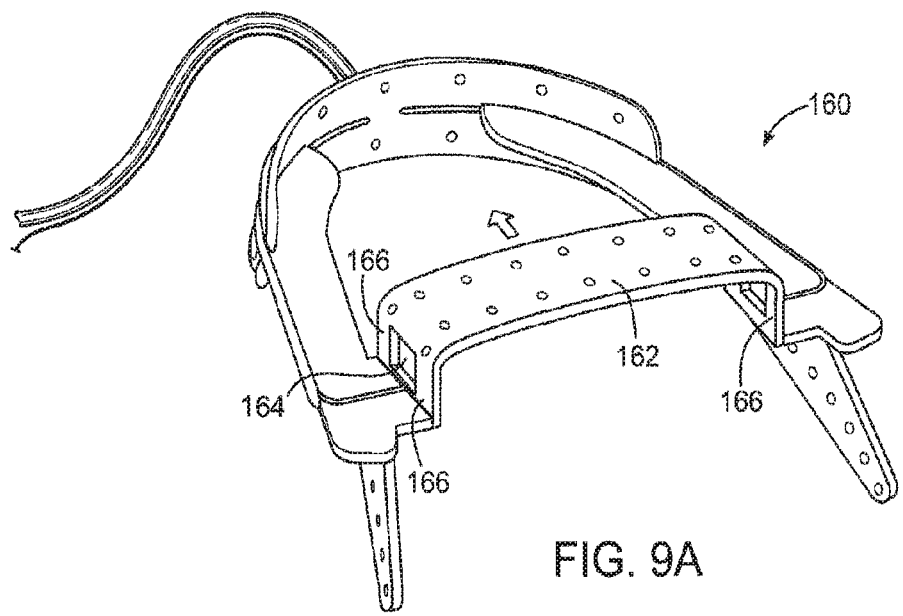
FIGS. 9A-9C illustrate an eighth embodiment of an oral device constructed in accordance with the principles of the present invention, with FIG. 9A being a perspective view, FIG. 9B being a side view, and FIG. 9C being a cross-sectional view taken along line 9C-9C of FIG. 9B.
Figure 9B:
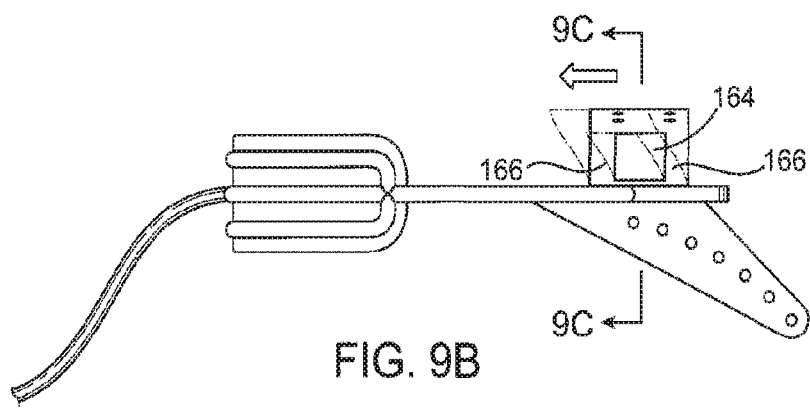
Figure 9C:
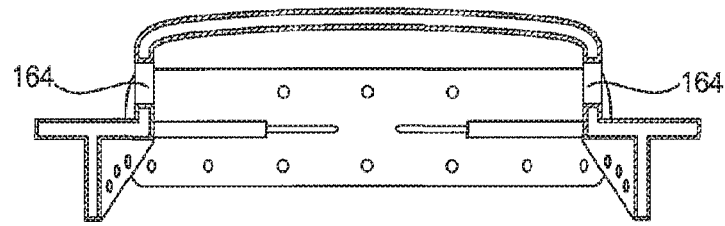

Referring now to FIGS. 9A-9C, an oral device 160 which is very similar to oral device 92 except that it employs a flexing tongue constraint structure 162 which can be used with any of the oral devices described is illustrated. Flexing tongue constraint structure 162 is very similar to tongue constraint structure 94 except that a window 164 is formed at each lateral end of the flexing tongue constraint structure 162. Windows 164 are sized to create a pair of narrow flexure arms 166 at each lateral end of flexing tongue constraint structure 162. Flexure arms 166 are fabricated from a flexible material such as polyurethane so that flexing tongue constraint structure 162 is allowed to flex anteriorly when the portion of the tongue it contacts is urged anteriorly by the negative pressure in the oral cavity. This anterior motion of flexing tongue constraint structure 162, best seen in FIG. 9B, may facilitate further anterior motion of the tongue and soft palate as compared with oral device 92, thereby improving the ability of oral device 160 to open the airway. Because flexing tongue constraint structure 162 and flexure arms 166 are hollow, negative pressures are conveyed in a very similar manner as with oral device 92.

Figure 10A:
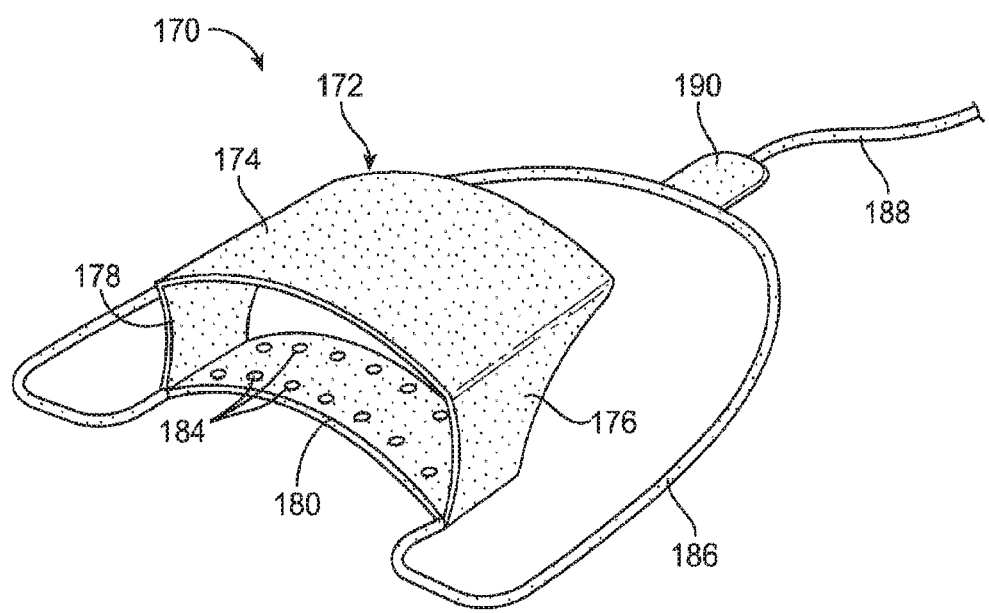
FIGS. 10A-10C illustrate a ninth embodiment of an oral device constructed in accordance with the principles of the present invention, where
Figure 10B:
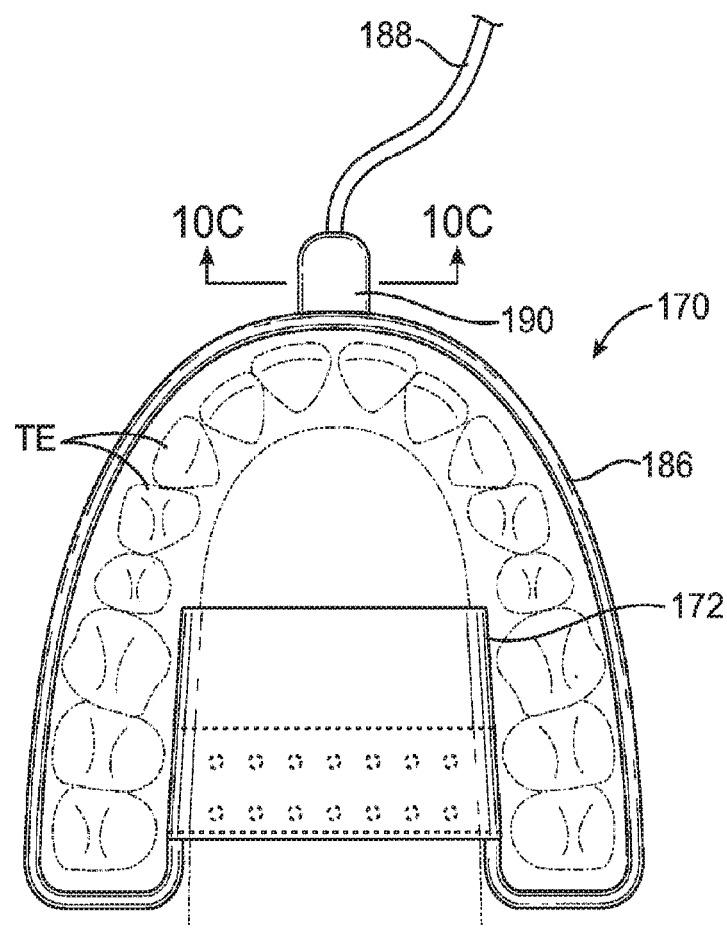
Figure 10C:
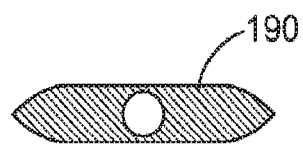
Figure 10D:
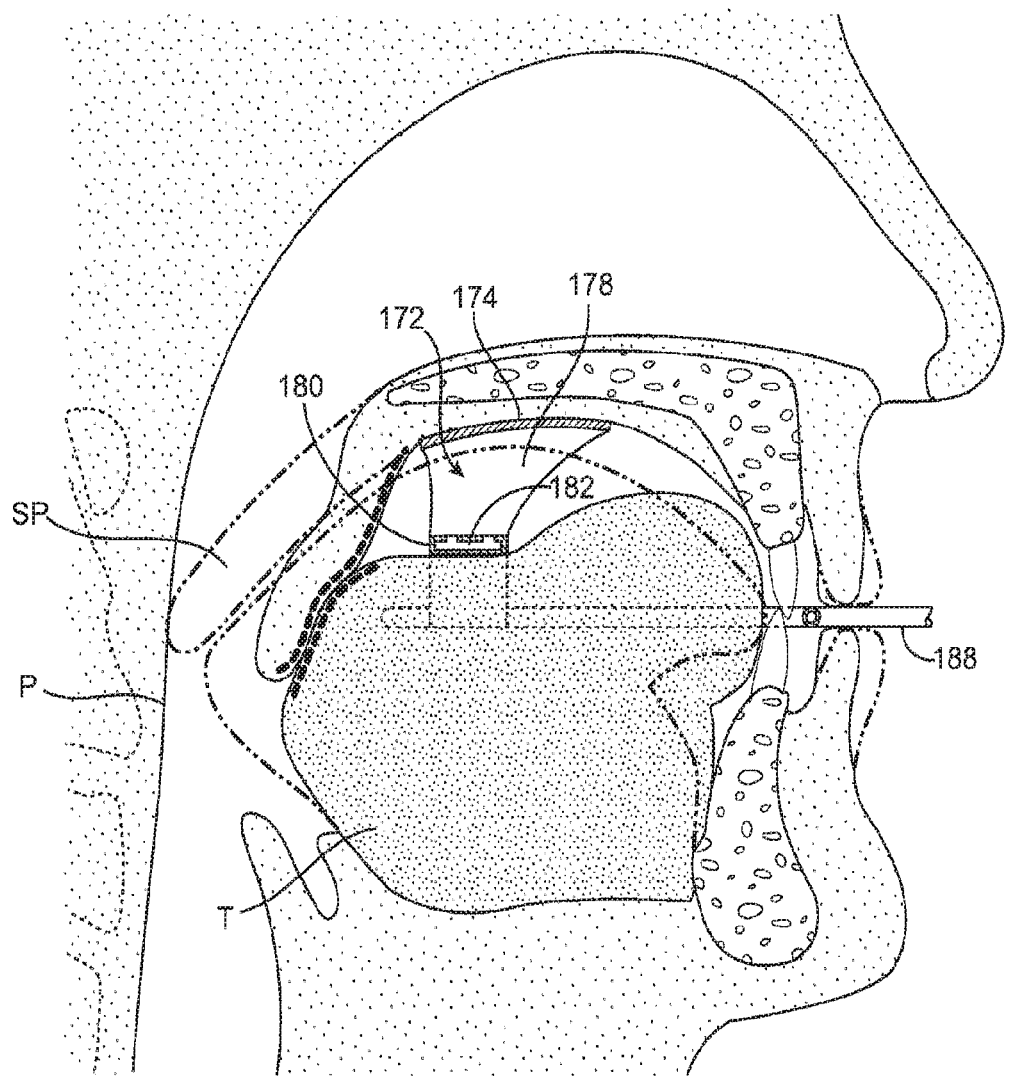
FIG. 10D illustrates use of the device of FIGS. 10A-10C for inhibiting OSA when placed in an oral cavity of a patient.

Referring now to FIGS. 10A-10D, an oral device 170 having an alternative anchor structure 172 will be described. In all previous embodiments, the anchor structure of the oral device has been intended to be held between the patient's teeth in order to provide a support for the tongue constraint. That is, the anchor structure held between the patient's teeth is attached to the tongue constraint and transmits force to maintain the tongue position through the anchor between the teeth. In the oral device 170, the anchor structure 172 has an upper surface 174 which is configured to rest against the inferior surface of the palate, as best seen in FIG. 10D. A pair of depending sidewalls 176 and 178 adjoins to a curved or arcuate tongue constraint 180 which includes an open interior or plenum 182 having a plurality of ports 184 over its upper surface.

Vacuum or negative pressure can be provided to the plenum 182 by a U-shaped tube 186 which is adapted to circumscribe the patient's teeth TE, as best shown in FIG. 10B. It can be seen that the teeth can be fully closed with the tube extending around the rear molars when the anchor structure 172 is positioned in the oral cavity, as shown in FIG. 10D. A flexible tube 188 is connected to the vacuum supply tube 186 through a lip seal structure 190, as shown in cross section in FIG. 10C. The lip seal structure 190 has a flat and tapered shape so the patient's upper and lower lips can conform to it thereby facilitating the seal in the oral cavity as a vacuum or negative pressure is drawn through the device.

Figure 11:
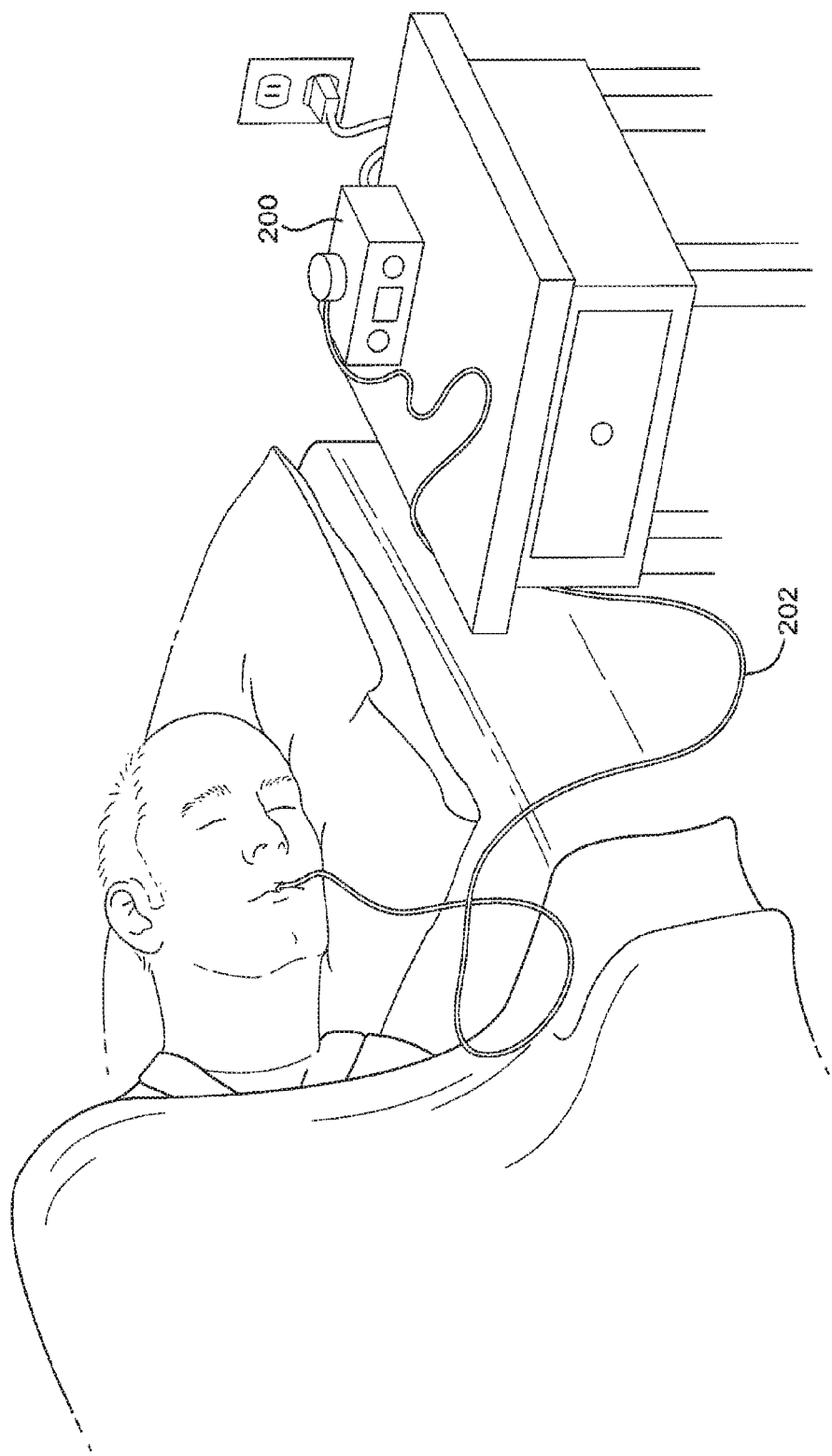
FIG. 11 is a perspective view illustrating a patient asleep at night using the apparatus of the present invention.

Referring now to FIG. 11, in addition to the portable battery powered vacuum source described earlier, the oral devices of the present invention may receive the desired vacuum or negative pressure from a tabletop unit 200 which can be operated off of house current and/or battery power. The tabletop unit 200 may be connected to the oral device (within the patient's mouth in FIG. 11) through a relatively long, flexible, crush-resistant, small and lightweight connector tube 202. The long connector tube is convenient and allows the patient to sleep comfortably in any position with minimal disruption.

Figure 12:
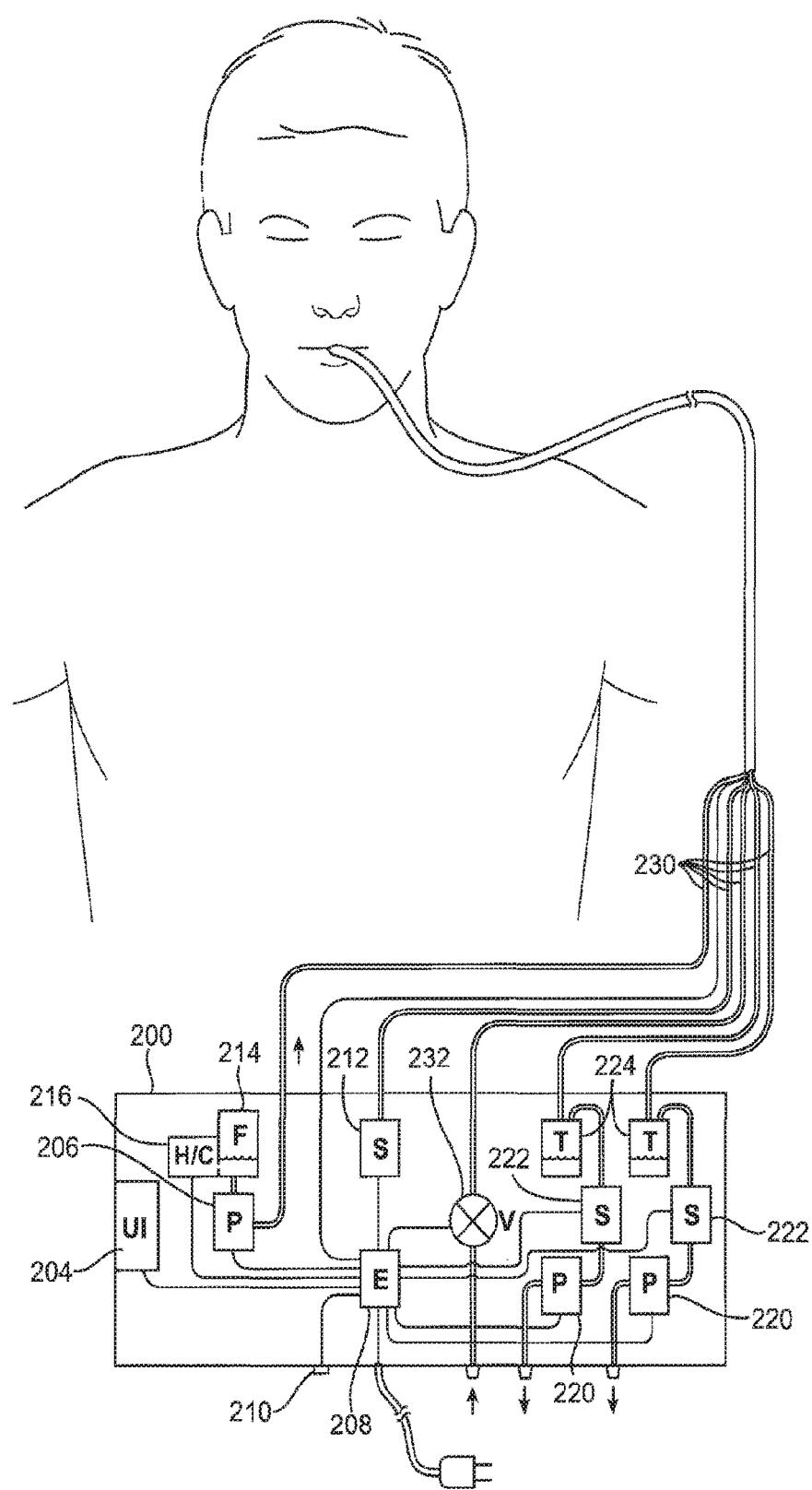
FIG. 12 is a schematic illustration of a control system or console for use in aspirating a negative pressure in the oral devices of the present invention.

The tabletop control unit 200 may comprise a number of internal components, as best illustrated in FIG. 12. The tabletop control unit will usually include a user interface 204. In order to generate the negative pressure used by the oral devices described above and to reduce the accumulation of fluid within the mouth, one or more pumps 220, sensors 222 for flow, pressure, or the like and traps 224 will usually be provided. The traps 224 remove saliva and other substances from the tubing to prevent them from entering the pumps 220. The sensors 222 may be used to determine if the device is operating and being applied properly. For example an air leak would generate higher than normal flow and the user could be alerted that there is a problem. Optionally valve 232 may be provided for briefly allowing air to enter the device or oral cavity in order to facilitate aspiration of fluids that have collected in the oral cavity or device. Optionally fluid source 214 and pump 206 for providing moisture and a heater/cooler 216 for heating or cooling the fluid may be provided. Electronics and power control module 208 will provide for the desired control functions of the unit. Optionally a feedback loop may be configured to monitor the pressure in the oral cavity for example as described above using tubes 80 and 82 connected to a pressure sensor 212 and to adjust the power of the one or more vacuum pumps 220 in order to maintain the desired level of negative pressure in the oral cavity. Varying distributions of saliva in the tubing that connects the control unit 200 to the oral devices described above will create a pressure differential and such a feedback loop could continually compensate for this varying differential. Optionally, a port 210 may be provided for external connection of the control unit to a computer or data distribution network. Each of these components may be connected to the oral device through appropriate tubes, wires or other connectors 230.

Figure 13A:
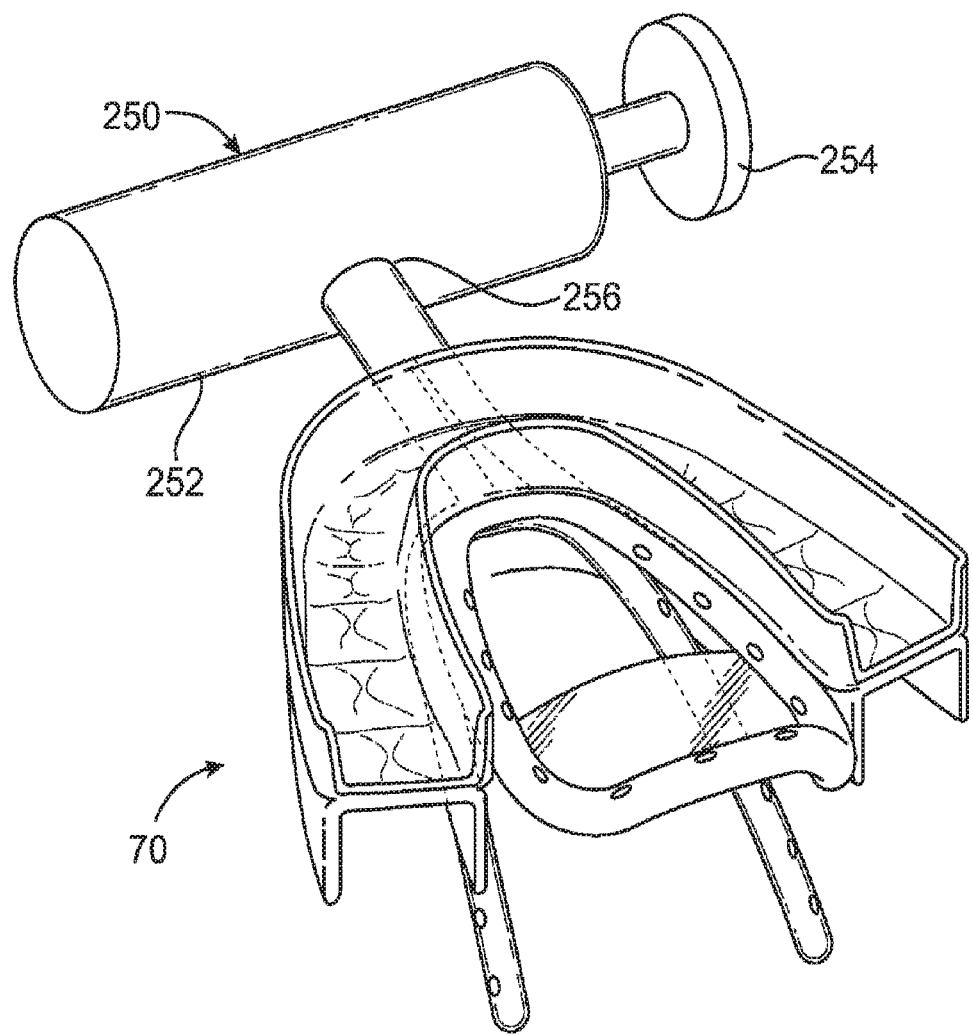
FIGS. 13A-13C illustrate a mechanical or manual vacuum generator that can be used with any of the oral devices of the present invention, where
Figure 13B:
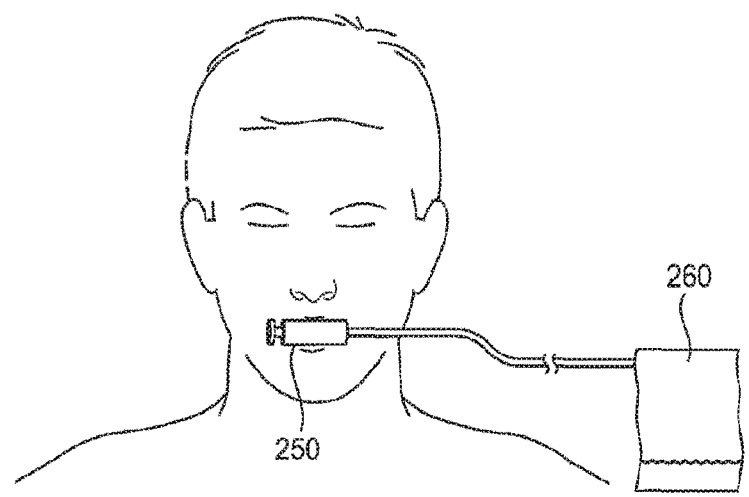
Figure 13C:
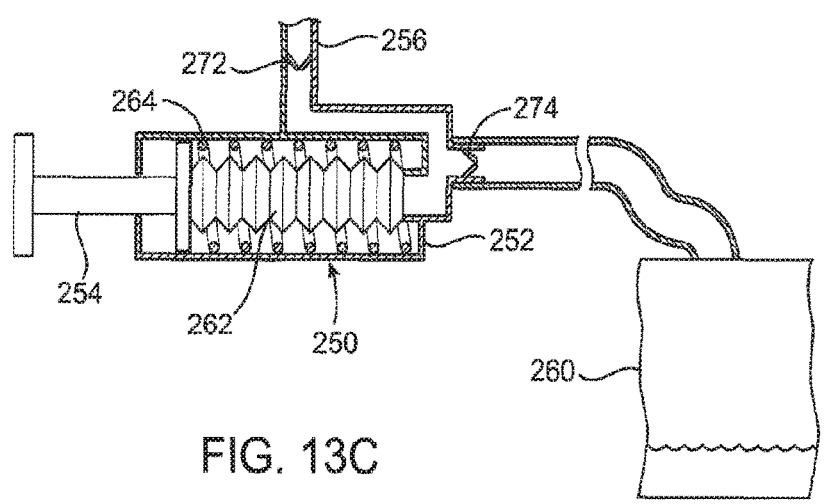

Referring now to FIGS. 13A-13C, a mechanical vacuum generator 250 will be described. The mechanical vacuum generator 250 includes a cylindrical body 252, a plunger 254, and an attachment port or tube 256 which can be fixedly or removably attached to the plenum structure of any of the oral devices described previously. Shown in FIG. 13A, the mechanical vacuum generator 250 is connected to the oral device 70 of FIG. 4.

The mechanical vacuum generator 250 may be attached to a saliva collection reservoir 260 which may be generally the same as the saliva collection reservoir 136 described previously in FIGS. 7F and 7E. Of course, other saliva-collecting or saliva-absorbing configurations may be employed without departing from the scope of the invention.

The mechanical vacuum generator 250 includes a bellows 262 attached to the plunger 254. A spring 264 is configured to urge the bellows to an expanded volume configuration, i.e. to the left, as shown in FIG. 13C. Thus, when the patient depresses the plunger 254, the bellows 262 may be compressed to the right, which at the same time compresses spring 264. The spring will urge the bellows to open and draw a vacuum through connecting line 256, which is connected to the oral device. One-way flow valves 272 and 274 permit saliva to pass into the cylindrical body 252 where it collects. When the user depresses the plunger 254, the saliva is expelled into the collection bag 260 through one-way valve 274. Plunger 254 may be depressed as often as necessary to maintain the desired vacuum or negative pressure within the oral device.

A further embodiment of an oral device according to the invention is illustrated in FIGS. 14A-14D. Oral device 280 has a tongue constraint 282 with a bite structure 284 integrally formed with or fixed to the tongue constraint 282 around its anterior and lateral edges. Similar to previous embodiments, bite structure 284 has a U-shaped channel 286 adapted to receive the upper teeth so as to anchor the oral device 280 in the oral cavity. U-shaped channel has an outer wall 287 which extends superiorly to cover at least a portion of the upper teeth, and an inner wall 289 which may be shorter or optionally eliminated entirely. Outer wall 287 and/or inner way 289 may have a height to cover the upper teeth entirely so as to inhibit leaks from the oral cavity posterior to the teeth.

Tongue constraint 282 comprises a curved or dome-shaped plate 288 having a concave inferior surface adapted to engage the superior surface of the tongue to constrain at least a portion of the tongue in a position spaced apart from the patient's hard palate, thereby creating a clear region superior to plate 288 and inferior to the hard palate that continuously extends from the posterior side of bite structure 284 to the soft palate. In preferred embodiments, the superior surface of tongue constraint 282 is spaced apart from the patient's hard palate by at least about 0.5 mm. Tongue constraint 282 preferably has sufficient rigidity to constrain the tongue in a position-spaced apart from the hard palate. While some flexibility is possible, tongue constraint 282 will have sufficient resilience and strength to overcome any deflection caused by movement of the tongue to return to an unbiased position in which the tongue is spaced apart from the hard palate. In order to apply a distributed force across a broad area of the tongue, tongue constraint 282 is preferably configured to engage at least ½ of the width of the tongue (in the lateral direction, left to right). In this embodiment, plate 288 of tongue constraint 282 spans the entire distance across the open end of U-shaped bite structure 284 between the patient's left and right molars and is thus configured to engage substantially the entire width of the tongue.

As in previous embodiments, the plate 288 preferably engages the medial region of the tongue so as not to contact the region of the tongue that tends to initiate the gag reflex. Plate 288 is preferably continuous throughout the area circumscribed by bite structure 284 (except for vacuum ports 296, described below). Plate 288 will usually engage the medial surface of the tongue at a location that is at least about ⅓ of the way, more preferably at least about ½ of the way, from the anterior tip of the tongue to the posterior end of the tongue. Usually, plate 288 engages the medial surface at a point posterior to the midpoint between the anterior and posterior ends of the hard palate. Plate 288 may engage the tongue as far back as or even beyond the posterior end of the hard palate where it joins to the soft palate; however, plate 288 is configured to allow the soft palate to engage the posterior side of plate 288 in a position in which the airway is at least partially open, so will usually not extend posteriorly more than about 20 mm beyond the posterior end of the hard palate HP, and preferably not more than about 25 mm posteriorly beyond the normal location of the patient's second molars. If an imaginary cylinder were drawn between the patient's nasopharynx and laryngopharynx with diameter about the same as the laryngopharynx, in preferred embodiments plate 288 would not intersect such a cylinder.

Plate 288 forms a soft palate landing pad 290 on its posterior side having a posterior surface 292 which angles inferiorly and posteriorly from the apex A of the dome-shaped plate 288. Soft palate landing pad 290 is adapted to engage the soft palate when vacuum is applied through the oral device. Posterior surface 292 may be arcuate, spherical, planar or a combination thereof. In exemplary embodiments, as shown in FIG. 14D, posterior surface 292 extends a length L of at least about 5 mm from the inferior surface 295 of bite structure 284, and posterior surface 292, or a plane P tangential with posterior surface 292, is disposed at an angle α of at least about 45°, more preferably about 60-135°, and most preferably about 90-135°, relative to a horizontal plane H containing an inferior surface 295 of the bite structure 284. Horizontal plane H is generally coplanar with the occlusal plane, the plane in which the upper and lower teeth meet when the patient bites together.

Plate 288 has a plurality of vacuum ports 296 extending entirely through its thickness. Vacuum ports 296 are disposed in locations on plate 288 selected to direct negative pressure (suction) within the clear region superior to plate 288 against the superior surface of the tongue on the inferior side of plate 288. Various locations and arrangements are possible, but in one embodiment vacuum ports 296 are disposed within a central region of plate 288 which contacts the medial region of the tongue. In this embodiment vacuum ports 296 are arranged in a grid generally centered on apex A in a central portion of plate 288 and extending laterally in both directions to points adjacent to U-shaped channel 286, with soft palate landing pad being free of vacuum ports. Optionally, vacuum ports 296 may also be provided on soft palate landing pad 290.

As an alternative to vacuum ports 296 shown, plate 288 may be made of a porous material to allow air to pass through it, such as a porous polyethylene or other porous polymer. As a further alternative, plate 288 may have very small or even microscopic holes created by laser drilling, etching, or other suitable process throughout its entire area or in a selected region or regions thereof.

A vacuum tube 298 is fixed to the surface of plate 288 and extends anteriorly through plate 288 and bite structure 284 where it connects to an extension tube 300, which is connectable to a suction source such as a vacuum pump or portable vacuum source as described in earlier embodiments. Optionally, a detachable connector (not shown) may be connected to the end of extension tube 300 to allow detachable connection to a complementary connector (not shown) on a portable vacuum source or a tube extending to the vacuum source. Vacuum tube 298 preferably has a plurality of holes 302 on a sidewall thereof, and may have an open distal end 304, through which vacuum is applied to the clear space created superiorly of plate 288. Vacuum tube 298 may be straight and located in the center of plate 288 as shown, or alternatively may have a variety of other configurations and locations on the oral device as described elsewhere herein. Vacuum tube 298 may terminate at a point anterior to apex A as illustrated, or may extend to a point further posterior on the plate 288. As an alternative to the vacuum tube 298 illustrated, a vacuum lumen may be formed integrally within plate 288 with outlet ports in the superior surface and/or inferior surface of plate 288 in communication with the vacuum lumen.

Oral device 280 further includes a lip seal 306 configured to be placed between the teeth and lips to help inhibit air from leaking between the lips so as to maintain a seal in the oral cavity. Lip seal 306 may comprise a flexible polymeric sheet slidably mounted over extension tube 300 and fluidly sealed therewith. Lip seal 306 will have sufficient flexibility to conform to the shape of the user's teeth and lips so as to provide a substantially air-tight seal.

Figure 14E:
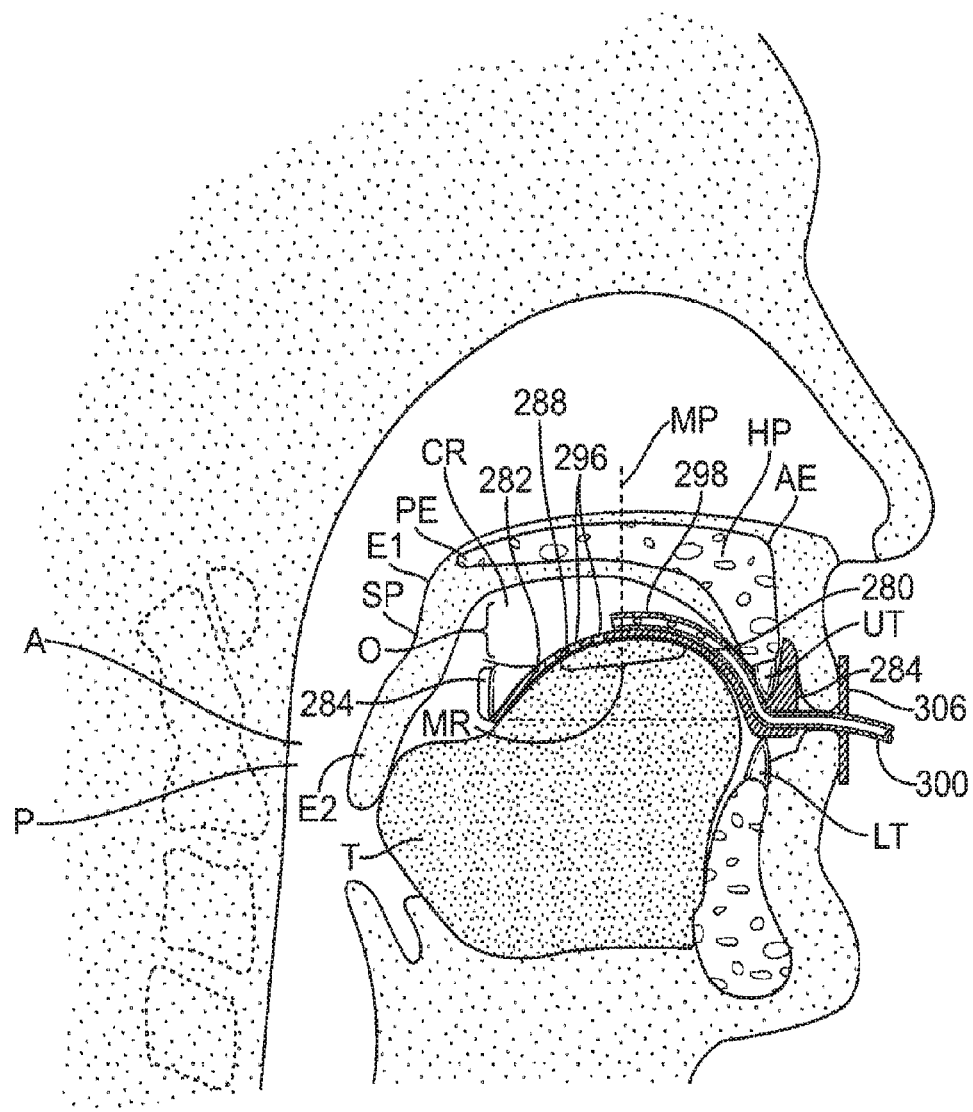
FIG. 14E is a side cross-sectional view of the oral device of FIGS. 14A-D positioned in a patient's oral cavity.

Referring to FIG. 14E, tongue constraint 282 preferably engages and constrains a region of the tongue T which is at least in part posterior to the midpoint MP between the anterior end AE and the posterior end PE of hard palate HP. In the embodiment shown, tongue constraint 282 extends in the posterior direction substantially the entire distance from the anterior end AE to the posterior end PE of hard palate HP, thus engaging both a medial region MR of the tongue T (roughly the middle third) as well as regions of the tongue anterior and posterior to the medial region MR. Tongue constraint 282 creates a posterior opening O bounded superiorly by the hard palate, laterally by the teeth and bite structure 284, and inferiorly by the posterior edge of plate 288. This posterior opening faces directly toward the soft palate SP and airway A, creating a vacuum flow path from the clear region CR directly to the soft palate. This allows vacuum to be applied to at least the upper portion of the soft palate SP, from the superior end E1 where it joins the hard palate to a point closer the free inferior tip E2. Exerting vacuum force on the superior portion of the soft palate effectively maintains the entire soft palate structure in a position in which the airway is unobstructed.

In use, vacuum applied through vacuum tube 298 is directed to the tongue T through vacuum ports 296 and holds the tongue in engagement with the inferior surface of plate 288. Although some or all of vacuum ports 296 may be blocked by the tongue, because the clear region maintained over oral device 280 is open posteriorly all the way to the soft palate, a vacuum flow path is maintained from vacuum tube 298 directly to the soft palate. Thus the negative pressure within the clear region exerts a force directly upon the soft palate through this vacuum flow path, maintaining the soft palate in an anterior position in which it does not obstruct the airway. Preferably, the suction force exerted on the soft palate through the clear region maintains the soft palate in sealing engagement with the tongue and/or with the soft palate landing pad 290, while the tongue is held in engagement with the inferior surface of the tongue restraint 282. This allows the airway to be substantially fluidly isolated from clear space CR where the vacuum is applied such that the pressure gradient between the airway and the oral cavity increases, thus urging the soft palate, tongue and other posterior oral tissues anteriorly out of the airway.

Still another embodiment of an oral device according to the invention is illustrated in FIGS. 15A-15E. In this embodiment, oral device 310 is identical to oral device 280 of FIGS. 14A-14D except as described below. Oral device 310 has a bite structure 311 like that of the previous embodiment, and a tongue constraint 312 comprising a plate 313 with a soft palate landing pad 314. Unlike the straight posterior edge of landing pad 290 in the previous embodiment, landing pad 314 has a posterior edge 315 with an arcuate shape that curves outwardly in the posterior and (optionally) inferior directions beyond the open end of bite structure 311. With this shape landing pad 314 may be more suitably located to engage the soft palate in some patients. In addition, landing pad 314 optionally includes a plurality of ribs 318 extending laterally across landing pad 314. Ribs 318 stand in relief on the posterior surface 316 of landing pad 314 to enhance engagement with the soft palate tissue, as well as help to channel the vacuum flow laterally. Ribs 318 may comprise tubular, round, or partially-round strips affixed to landing pad 314, or ribs 318 may be integrally formed with landing pad 314. Ribs may also be provided along the superior surface of plate 313 oriented either laterally like ribs 318 illustrated, in the anterior-posterior direction, or in other orientations.

A further difference from the embodiment of FIGS. 14A-14D is the vacuum tube 320, which extends past apex A to a point near the posterior edge 315 of oral device 310. In this way, vacuum tube 320 ensures that negative pressure is applied along the posterior edge of oral device 310, a location closer to the soft palate. Vacuum tube 320 includes side holes 322 and an open distal end 324 through which negative pressure may be applied. Additionally, in this embodiment, tongue constraint 312 has no vacuum ports extending through plate 313 as in the earlier embodiment.

Another unique aspect of oral device 310 is the placement of spacing elements 324 on the inferior surface 326 of bite structure 311. Spacing elements 324 are a soft pliable material, e.g. polymeric tubing or foam, having a thickness of about 2-12 mm. Each spacing elements 324 is positioned at or near a posterior end 329 of bite structure 311 and extends anteriorly approximately 25-75% of the way around to the front of bite structure 311. Alternatively, multiple spacing elements of shorter length may be placed at intervals along each side of bite structure 31. In this way spacing elements 325 sit between the patient's upper and lower teeth and hold open the lower jaw slightly. Such slight opening of the jaw during sleep has been shown to improve airway patency in some circumstances.

A further unique aspect of oral device 310 is that a jaw positioning tab 328 is disposed on the anterior closed end of bite structure 311 and extends downwardly therefrom sufficiently to engage the posterior surface of the lower front teeth when oral device 310 is positioned in the oral cavity. Jaw positioning tab 328 is of sufficient stiffness and positioned in a suitable location on bite structure 311 to maintain the patient's lower jaw in a position slightly forward of a normal relaxed position. Such forward positioning of the jaw has been found to improve airway patency in some circumstances.

It should be understood that ribs 318, spacing element 324, and jaw positioning tab 328 are optional features of oral device 310 and that any or both of these features may be eliminated without departing from the scope of the invention or limiting its utility.

In other respects oral device 310 is similar to oral device 280 of FIGS. 14A-14D and operates in the same way. It will be understood that oral device 310 will usually include a lip seal like lip seal 306 of the previously described embodiment although in FIGS. 15A-15D the lip seal is removed for added clarity. It should be further understood that any or all of the features of oral device 310 may optionally be included in oral device 280 or in other embodiments described herein.

Figure 16A:
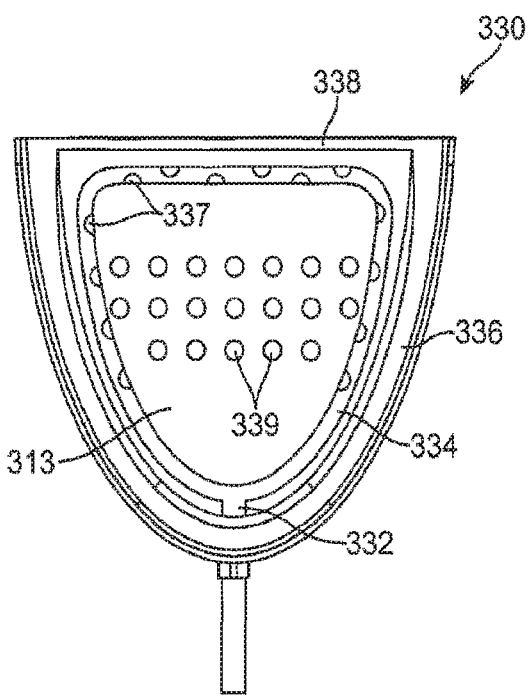
FIGS. 16A-16C are top, front and side cross-sectional views, respectively, of an oral device according to the invention in still another embodiment thereof, in which the lip seal is removed for clarity.
Figure 16B:
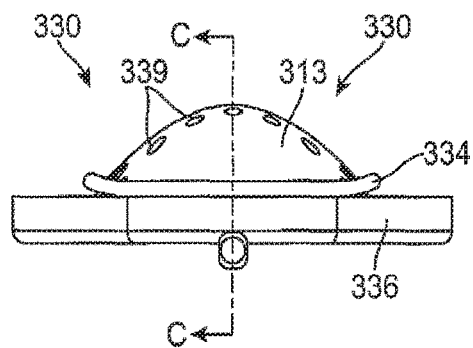
Figure 16C:
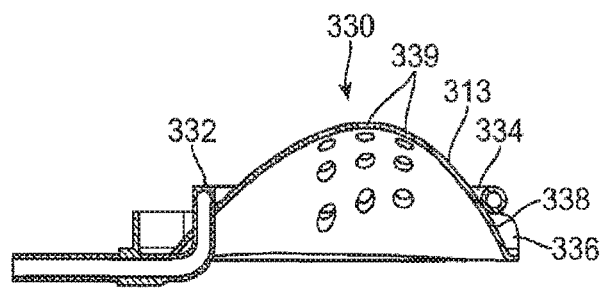

FIGS. 16A-16C illustrate an oral device 330 identical to oral device 280 of FIGS. 14A-14D except an alternative configuration of vacuum tube 320 is shown. In this embodiment, vacuum tube 332 has a loop 334 extending around tongue constraint 313 near the outer edges thereof adjacent bite structure 336 and along the posterior edge 338 of tongue constraint 313. Vacuum tube 320 has a plurality of side holes 337 distributed evenly around loop 334. A plurality of vacuum ports 339 are disposed in a central region of tongue constraint 313 with loop 334 encircling most if not all of vacuum ports 339. In this way negative pressure is distributed by vacuum tube 320 directly to the outer edges and posterior region of tongue constraint 313 to ensure adequate negative pressure is available in those regions. In addition, loop 334 more evenly distributes negative pressure across a larger portion of the surface of tongue constraint 313.

FIGS. 17A-17D illustrate an oral device 340 according to the invention similar in many respects to oral device 280 of FIGS. 14A-14D except, in place of vacuum tube 320, oral device 340 has tongue constraint 341 having a hollow interior chamber 342 enclosed between a superior wall 344 and an inferior wall 346. A vacuum tube 348 is in fluid communication with chamber 342 and extends through inferior wall 346 and anteriorly through bite structure 350 where it may be connected to a vacuum source. A plurality of inferior vacuum ports 352 extend through inferior wall 346 in communication with chamber 342 and are positioned so as to apply suction to the tongue. A plurality of posterior vacuum ports 354 extend through superior wall 344 in communication with chamber 342 and are oriented to face in a posterior direction away from the tongue and toward the soft palate. Preferably, at least some of posterior ports 354 are disposed in a plane P which is at an angle β of at least about 45°, more preferably about 60°-180°, and most preferably about 90°-180° in the superior direction relative to the occlusal plane O which contains the inferior surface 349 of bite structure 343. Optionally, posterior vacuum ports 354 may be further distributed along the upper portion of superior wall 344 so as to face the hard palate. In this way, vacuum may be conveyed through vacuum tube 348 into chamber 342, from which suction is applied to the tongue through inferior vacuum ports 352 and to the soft palate through posterior vacuum ports 354.

In the embodiment of FIGS. 17A-17C, tongue constraint 341 has an overall thickness (or height) greater than that of oral device 280 in order to provide room for chamber 342; however, superior wall 344 will preferably be configured so that a clear region is maintained above tongue constraint 341 between the top surface of superior wall 344 and the hard palate when oral device 340 is positioned in the oral cavity.

As an alternative, FIGS. 18A-18C illustrate an oral device 340A substantially identical to oral device 340 except in this embodiment, the superior wall 344A extends upwardly to the hard palate such that the clear region CR formed by tongue constraint 341A is enclosed within chamber 342A. In this embodiment, superior wall 344A is shaped so as to conform generally to the shape of the hard palate and there will be little or no space between superior wall 344A and the surface of the hard palate when oral device 340A is positioned in the oral cavity. Posterior ports 354A as well as inferior ports 352A are thus in direct communication with the clear region CR within chamber 342A. As in the embodiment of FIGS. 17A-17D, posterior ports 354A face away from the tongue and toward the hard palate, preferably lying in a plane which forms an angle of at least about 45°, more preferably about 60°-180°, and most preferably about 90°-180° in the superior direction relative to the occlusal plane.

In the embodiment of FIGS. 19A-19D, oral device 360 is similar to oral device 340 of FIGS. 17A-17D, except that tongue constraint 362 comprises two separate hollow chambers within it, including an anterior chamber 364 and a posterior chamber 366, each enclosed by a superior wall 368 and an inferior wall 370. Preferably, tongue constraint 362 is a molded construction with anterior chamber 364 and posterior chamber 366 integrally formed within it. A transverse wall 372 divides anterior chamber 364 from posterior chamber 366. A plurality of inferior ports 374 are disposed in inferior wall 370 in communication with anterior chamber 364, and a plurality of posterior ports 376 are disposed in superior wall 368 in communication with posterior chamber 366. As in other embodiments, inferior ports 374 are positioned so as to apply suction to the tongue, while posterior ports 376 are positioned so as to face away from the tongue and toward the soft palate in order to apply suction to the soft palate and not be blocked by the tongue when it is engaged by inferior wall 370. As described above in connection with FIGS. 17A-17D, at least some of posterior ports 376 are disposed in a plane which is at an angle of at least about 45°, more preferably about 60°-180°, and most preferably about 90°-180° in the superior direction relative to the occlusal plane. An anterior supply conduit 380 extends through tongue constraint 362 from anterior chamber 364 to the anterior end of tongue constraint 362, while a posterior supply conduit 382 extends from posterior chamber 366 to the anterior end of tongue constraint 362. A first vacuum tube 384 connects to anterior supply conduit 380 and a second vacuum tube 386 connects to posterior supply conduit 382, each vacuum tube extending through bite structure 388 and being configured to connect to a vacuum source.

Figure 19E:
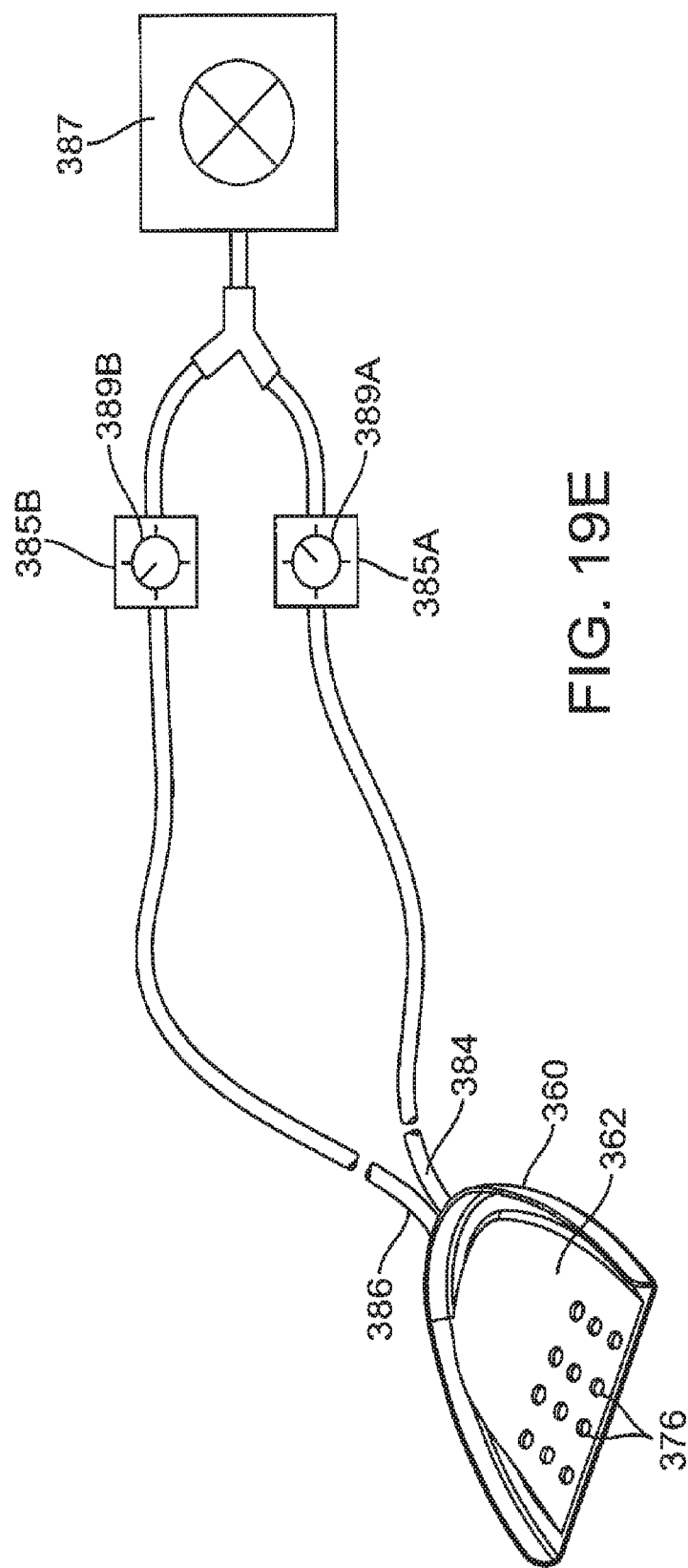
FIG. 19E is a schematic illustration of a system for applying different pressures to different regions of the oral cavity shown with the oral device of FIGS. 19A-D.

Oral device 360 is particularly advantageous in that the negative pressures within anterior chamber 364 and posterior chamber 366 can be controlled independently of one another. As illustrated in FIG. 19E, vacuum tubes 384, 386 may be connected to separate pressure regulators 385A, 385B, which are in turn fluidly connected to a single vacuum pump 387. Pressure regulators 385 are adjustable using control knobs 389A, 389B to set the level of negative pressure applied through each of vacuum tubes 384, 386. In this way, the negative pressure in each of anterior chamber 364 and posterior chamber 366 (not shown in FIG. 19E) can be independently controlled and optimized to keep the soft palate and tongue free of the airway. For example, different pressures could be applied to different regions of the oral cavity (e.g. the tongue and the soft palate) to achieve the desired displacement of different tissues. In addition, air under positive pressure can be delivered through either vacuum tube 384 or vacuum tube 386 while air at a different pressure or negative pressure is delivered through the other vacuum tube, for purposes of removing saliva from the vacuum tubes, delivering positive pressure to the airway or other regions, or achieving other desired effects. In an alternative embodiment, vacuum tubes 384, 386 may be connected to two separate pumps which are independently controllable to adjust the level of positive or negative pressure delivered, as shown in FIG. 23C, described below.

Figure 20A:
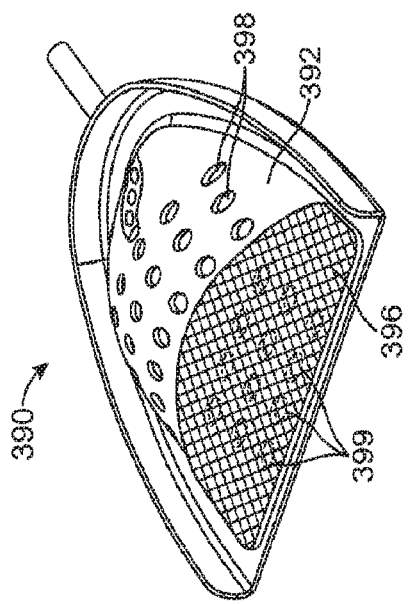
FIGS. 20A-20C are top, oblique and side cross-sectional views, respectively of an oral device according to the invention in still another embodiment thereof, in which the lip seal is removed for clarity.
Figure 20B:
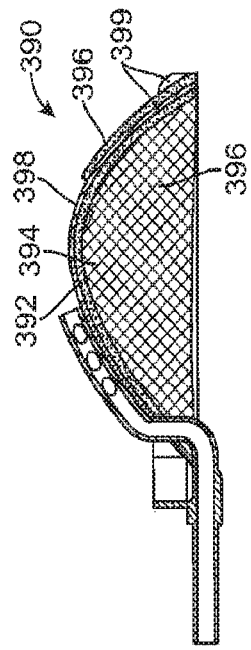
Figure 20C:
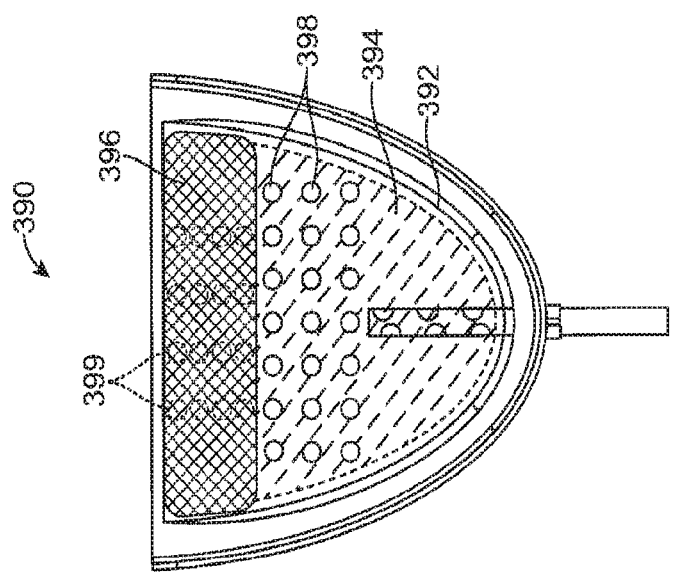

Turning to FIGS. 20A-20C, in a further embodiment, oral device 390 is constructed identically to oral device 280 of FIGS. 14A-14D except that tongue constraint 392 includes an inferior pad 394 adhered to the inferior surface of tongue constraint 392, and a posterior pad 396 adhered to a posterior surface of tongue constraint 392. Inferior pad 394 and posterior pad 396 are composed of a soft, flexible and porous material such as Dacron, cotton, or foam, and are adapted to reduce friction and abrasion of the tongue and/or soft palate tissues which engage tongue constraint 392. Inferior pad 394 and posterior pad 394 are sufficiently porous to allow vacuum to be applied through them from inferior vacuum ports 398 or posterior vacuum ports 399. It should be appreciated that either inferior pad 394 or posterior pad 396 may optionally be used without the other, and that either or both inferior pad 394 or posterior pad 396 could be used with any of the other embodiments described above or below.

Figure 21A:
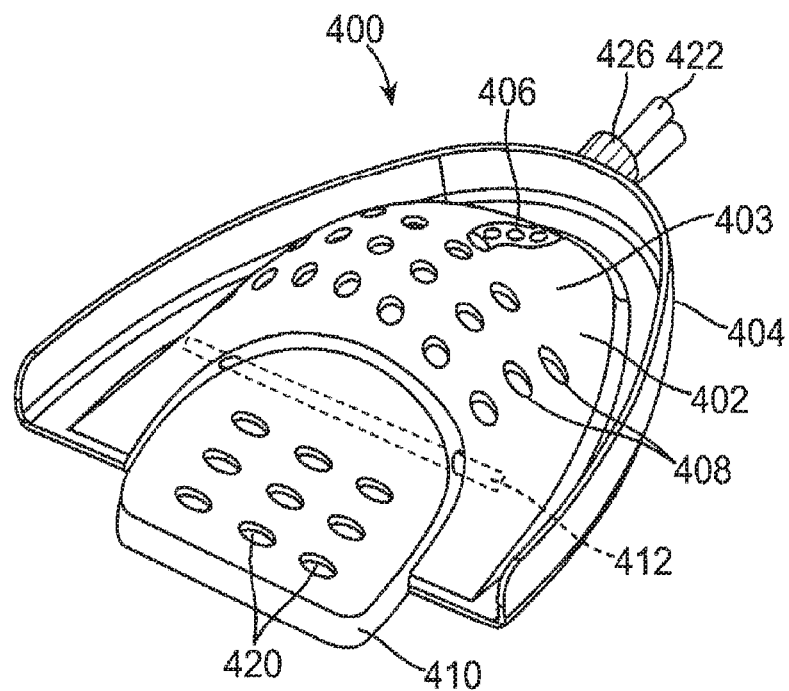
FIGS. 21A-21B are oblique and side cross-sectional views, respectively of an oral device according to the invention in still another embodiment thereof, in which the lip seal is removed for clarity.
Figure 21B:
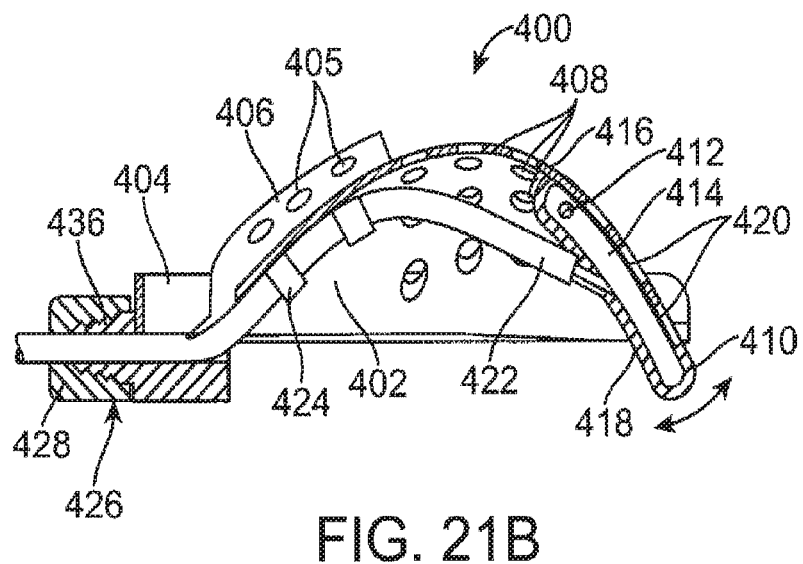

FIGS. 21A-21B illustrate a further embodiment of an oral device according to the invention. In this embodiment, like other embodiments elsewhere described, oral device 400 comprises a tongue constraint 402 and a bite structure 404. Tongue constraint 402 comprises a dome-shape plate 403 with a plurality of inferior vacuum ports 408 extending through plate 403 in a central region thereof. An anterior vacuum tube 406 is fixed to the superior surface of plate 403 and has a plurality of side holes 405 through which vacuum may be conveyed.

Different from previously describe embodiments, a landing pad 410 is pivotally coupled to tongue constraint 402 by a transverse pin 412, so that landing pad 410 is rotationally movable relative to plate 403. Landing pad 410 has a hollow interior chamber 414 enclosed by a posterior wall 416 and an anterior wall 418. A plurality of posterior ports 420 are disposed in posterior wall 416 in communication with chamber 414. As in the embodiments of FIGS. 17-19, posterior ports 420 are configured to face the soft palate and away from the tongue, preferably being disposed plane which is at an angle β of at least about 45°, more preferably about 60°-180°, and most preferably about 90°-180° in the superior direction relative to the occlusal plane. Notably, the angle of posterior ports 420 relative to the occlusal plane may be varied by pivoting landing pad 410 relative to plate 403.

A posterior vacuum tube 422 is connected to anterior wall 418 in communication with chamber 414. Posterior vacuum tube 422 extends anteriorly along the inferior side of plate 403, which optionally may include eyelets 424 through which posterior vacuum tube is slidably positioned to keep it close to plate 403. Posterior vacuum tube 422 extends slidably through bite structure 404 and a clamp 426 fixed to the anterior side thereof. Clamp 426 has a cap 428 threaded onto a tapered receptacle 430 each having a central passage through which posterior vacuum tube extends. Tapered receptacle 430 may be axially split and/or sufficiently conformable that tapered receptacle 430 is urged radially inward to engage posterior vacuum tube 422 as cap 428 is rotationally tightened. Of course, various clamps suitable for clamping posterior vacuum tube 422 are well known and may be used in place of the exemplary clamp illustrated. By sliding posterior vacuum tube 422 anteriorly or posteriorly, landing pad 410 is pivoted relative to plate 403. It should be understood that pull wires, rods, or other means could be used instead of posterior vacuum tube to pivot landing pad 403.

Advantageously, different negative pressures may be applied through anterior vacuum tube 406 and posterior vacuum tube 422 so that the suction applied to the soft palate through posterior ports 420 may be controlled independently of the suction applied to the tongue through inferior ports 408. For example, oral device 400 may be used with the system illustrated in FIG. 19E or the system illustrated in FIG. 23C. When vacuum has been applied through posterior ports 420 such the soft palate has become engaged against landing pad 410, posterior vacuum tube 422 maybe tensioned to pivot landing pad 410 anteriorly, thereby helping to draw the soft palate further away from the patient's airway. Once landing pad 410 is in the desired position, clamp 426 may be tightened to lock the posterior vacuum tube 422 and landing pad 410 in place.

Referring now to FIGS. 22 and 22A-22B, in a further embodiment an oral device 434 comprises a tongue constraint 436 movably coupled to a bite structure 438. Tongue constraint 436 has a superior wall 440 and an inferior wall 442 enclosing a hollow chamber 444. A plurality of inferior ports 446 extend through inferior wall 442 in communication with chamber 444. A plurality of posterior ports 448 are disposed in a posterior region of superior wall 440 in communication with chamber 444. Posterior ports face toward the soft palate and away from the tongue to remain unobstructed by the tongue when vacuum is applied therethrough, preferably lying in a plane which is at an angle of at least about 45°, more preferably about 60°-180°, and most preferably about 90°-180° in the superior direction relative to the occlusal plane. A vacuum tube 450 is connected to tongue constraint 436 in communication with chamber 444 and extends slidably through a channel 452 in bite structure 438. A clamp 454 is mounted to bite structure 438 and is adapted to lock vacuum tube 450 in position relative to bite structure 438. Clamp 454 may be constructed like clamp 426 of FIGS. 21A-21B or may have any other known clamp design suited for its purpose.

Bite structure 438 is U-shaped with a closed anterior end 439, an open posterior end 441, and an inner wall 456 along its interior side. A pair of channels 458 is disposed in inner wall 456 on opposing sides of bite structure 438 near its open end 441. A pair of pins 460 is attached to opposing lateral sides of tongue constraint 436 and extends laterally through channels 458. Pins 460 are slidable in channels 458 so that tongue constraint 436 is movably anteriorly and posteriorly relative to bite structure 438. In this way, vacuum may be applied through vacuum tube 450 and chamber 444 so as to apply suction through inferior ports 446 to the tongue, and through posterior ports 448 to the soft palate. When these tissues have been engaged, tension may be exerted on vacuum tube 450 to move tongue constraint 436 anteriorly relative to bite structure 438, thereby retracting the tongue and soft palate further forward and away from the airway. Once in the desired position, vacuum tube 450 may be clamped in place by tightening clamp 454 so as to hold tongue restraint 436 in position relative to bite structure 438.

Figure 23A:
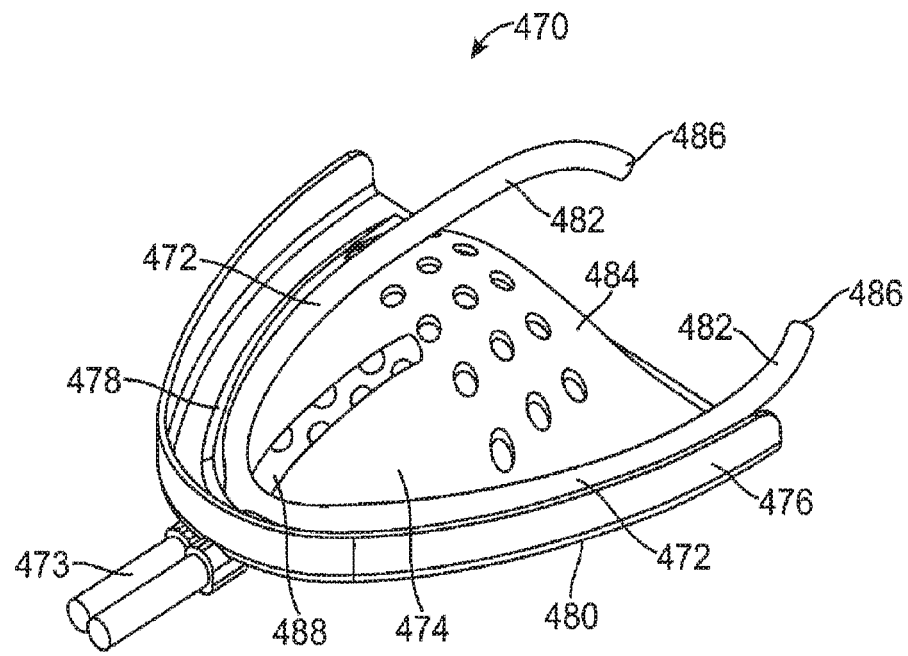
FIGS. 23A-23B are oblique and side cross-sectional views, respectively, of an oral device according to the invention in still another embodiment thereof, in which the lip seal is removed for clarity.
Figure 23B:
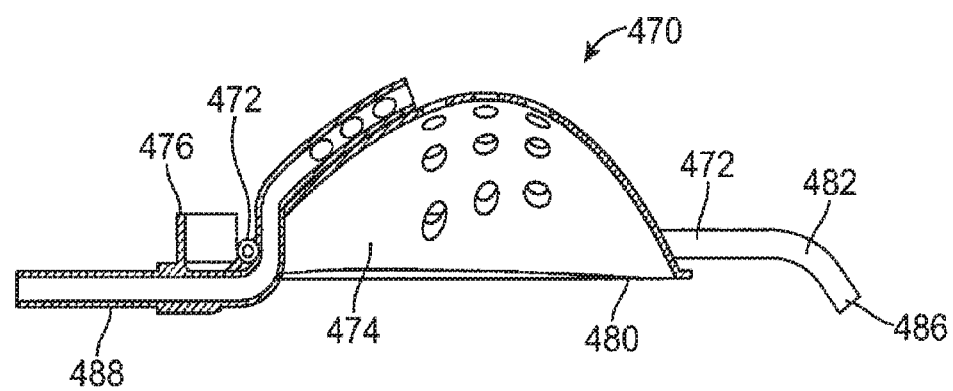
Figure 23C:
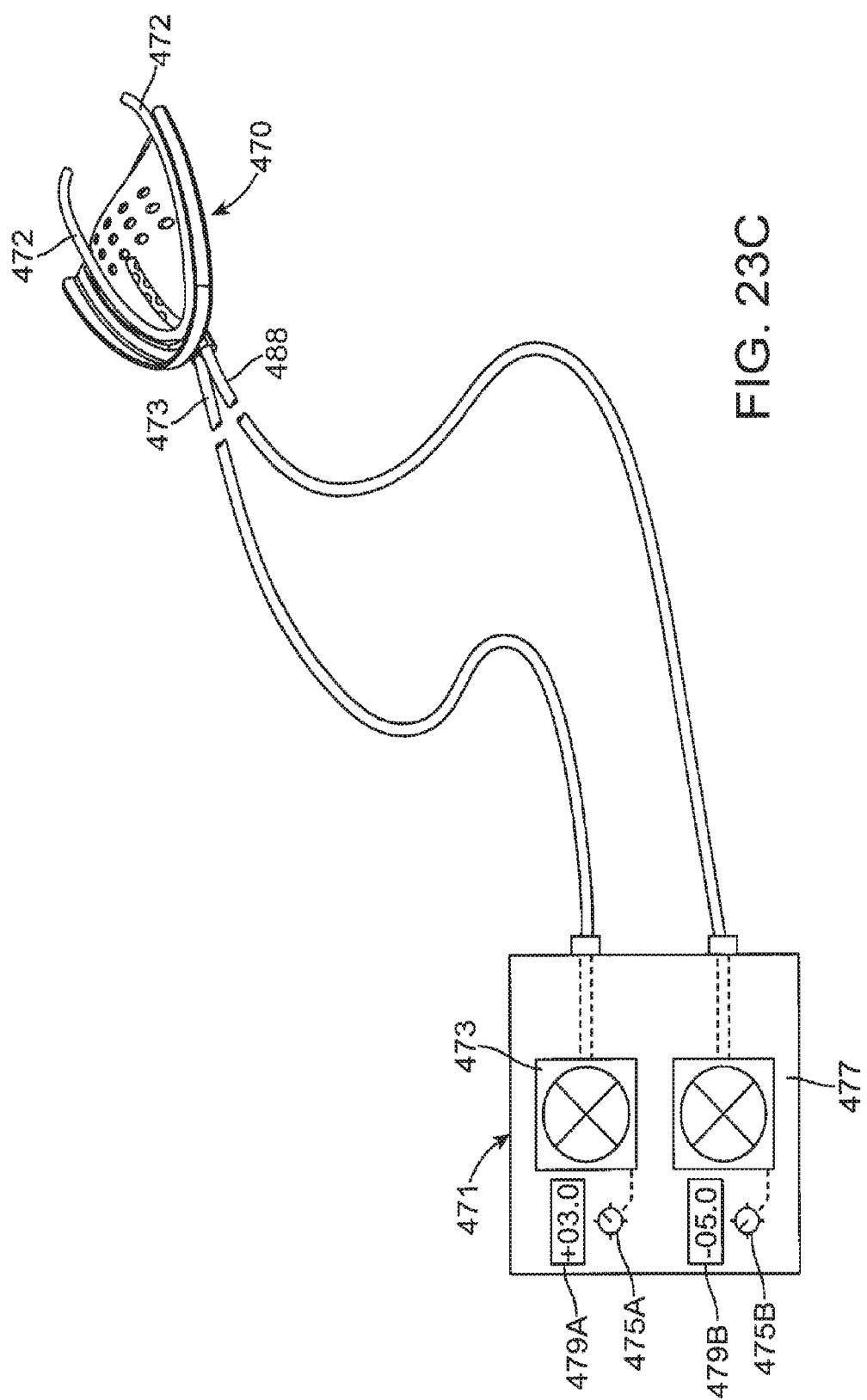
FIG. 23C is a schematic illustration of a system for delivering different pressures to different regions of the oral cavity, shown with the oral device of FIGS. 23A-B.

FIGS. 23A-23B illustrate another embodiment of an oral device according to the invention. In this embodiment, oral device 470 is identical to oral device 280 of FIGS. 14A-14D except that oral device 470 is adapted to deliver air under positive pressure into the patient's airway while the tongue is constrained and negative pressure is applied to the soft palate and tongue. Oral device 470 includes at least one, preferably two (as shown), delivery conduits 472 fixed to the upper surface of tongue constraint 474. Alternatively delivery conduits 472 may be fixed to bite structure 476, e.g. to its inner wall 478 or to its inferior surface 480. In the latter case delivery conduits 472 may serve the additional purpose of acting as a spacer between the patient's upper and lower teeth to keep them slightly apart when the oral device is in place. As a further alternative, all or part of delivery conduits 472 may be formed by an interior lumen (not shown) formed integrally within tongue constraint 474 or bite structure 476. Delivery conduits 472 have posterior portions 482 extending from the posterior edge 484 of tongue constraint 474 with free posterior ends 486 adapted to extend into the patient's airway. Delivery conduits 472 connect to a delivery tube 473 which extends through bite structure 476 and is adapted to connect to a fluid supply tube (not shown) outside the patient's oral cavity, which in turn may be connected to pump (not shown) for delivering air or other gasses under positive pressure. Alternatively, delivery tube 473 may be open to room air so that the airway is in communication with air outside the oral cavity in order to allow mouth breathing while the device is in place and while the oral cavity seal is maintained.

As in the case of oral device 280, with oral device 470 in place in the patient's oral cavity, tongue constraint 474 maintains at least a portion of the tongue in a position spaced apart from the patient's hard palate so as to maintain a clear region superior to tongue constraint 474. Negative pressure may be applied through vacuum lumen 488 to exert vacuum force on the soft palate and tongue, thereby causing the soft palate and tongue to be maintained in sealing engagement with one another anterior to the patient's airway, isolating the airway from the remainder of the oral cavity. The soft palate, tongue, and oral device may alternatively seal to each other in any combination in order to substantially fluidly isolate the airway. In this embodiment, delivery conduits 472 are adapted to extend into the airway between the soft palate and tongue while still allowing these tissues to seal against each other and around the periphery of delivery conduits 472. Air or other suitable gasses may be delivered to the airway under positive pressure through delivery conduits 472 thereby enhancing the pressure gradient between the airway and the oral cavity, helping to urge the soft palate and tongue anteriorly out of the airway and preferably in sealing engagement with one another. Positive pressure delivered to the airway may also apply forces to other tissues in a manner that improves airway patency.

A dual-pump system for use with oral device 470 is illustrated in FIG. 23C. System 471 comprises a first pump 473 controlled via a control knob 475A and a second pump 477 controlled via a second control know 475B. A first readout 479A displays the pressure level being applied by first pump 473, while a second readout 479B displays the pressure level being applied by second pump 477. Delivery tube 473 is connected to first pump 473 while vacuum tube 488 is connected to second pump 477. In this way, first pump 473 may deliver air under an adjustable level of positive pressure through delivery conduits 472, while second pump 477 may be adjusted to apply a desired level of negative pressure through vacuum lumen 488. Optionally, pressure lumens or sensors may be provided on oral device 470 to monitor negative pressure in the oral cavity and/or positive pressure in the airway. These may be coupled to first and second pumps 473, 477 which may be automatically controlled to adjust pump speed or pressure to maintain desired pressure levels or a desired pressure gradient between the airway and the oral cavity.

Figure 24A:
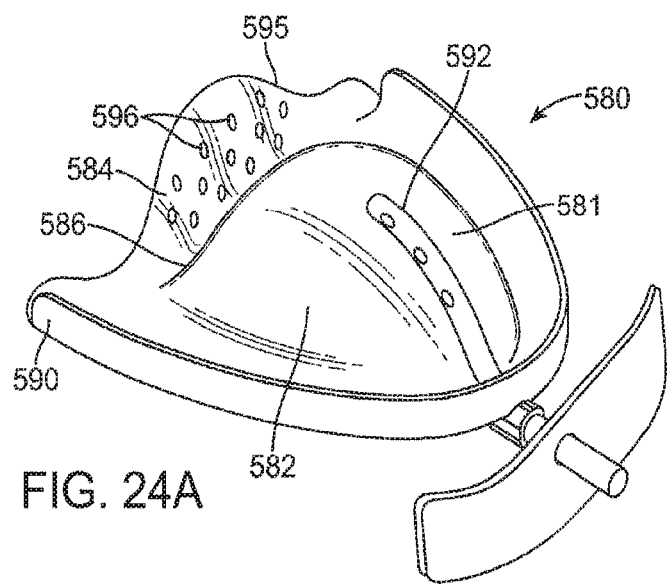
FIGS. 24A-24C are oblique, top, and side cross-sectional views, respectively, of an oral device according to the invention in still another embodiment thereof.
Figure 24B:
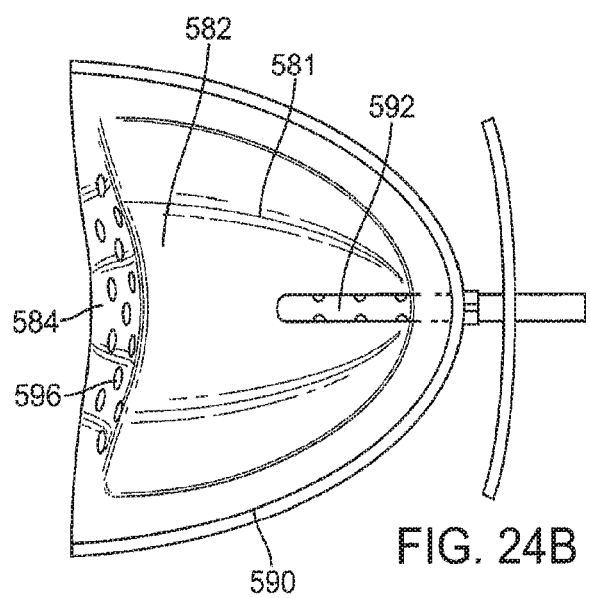
Figure 24C:
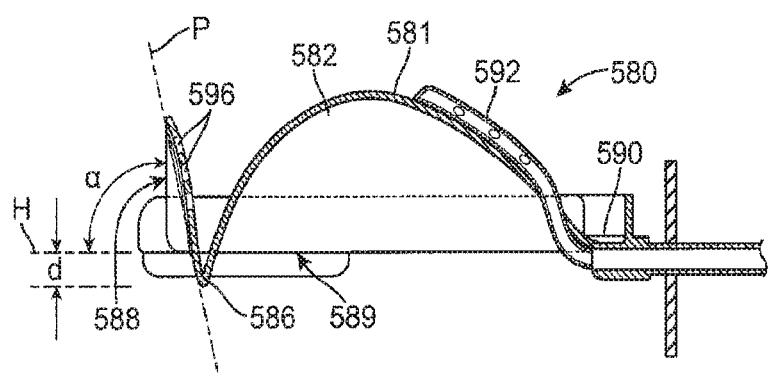

In a further embodiment of the invention, illustrated in FIGS. 24A-24C, an oral device 580 is substantially identical to oral device 280 of FIGS. 14A-14D, except in this embodiment, oral device 580 comprises a tongue constraint 581 having a plate 582 for engaging the patient's tongue and a landing pad 584 which extends in a generally superior direction from a posterior edge 586 of plate 582. As shown in FIG. 24C, landing pad 584 has a posterior surface 588 at least a portion of which lies in a plane P which is at an angle α of at least about 30°, more preferably about 45-135°, and most preferably about 60-100° relative to the occlusal plane H containing the inferior surface 589 of bite structure 590. In this way, posterior surface 588 is configured to receive and engage the soft palate as it is drawn forward by vacuum pressure applied through vacuum tube 592. Posterior surface 588 may have a curvature either or both laterally right-left and superiorly-inferiorly so as to present a concave surface into which the soft palate is drawn. The superior edge 595 of landing pad 584 preferably has an arched shape corresponding to the shape of the hard palate, and may be configured to engage the hard palate and even to seal therewith, or alternatively may be spaced apart from the hard palate. In addition, posterior edge 586 of plate 582, which forms the inferior edge of landing pad 584, may be disposed in various positions relative to the occlusal plane H, including both superior and inferior to plane H. In a particular embodiment, posterior edge 586 is disposed a distance d of about 2-7 mm, more preferably about 3-6 mm, inferior to plane H.

A plurality of posterior ports 596 are disposed in landing pad 584 and extend through its thickness so that, with oral device 580 in place in the patient's oral cavity, posterior ports 596, lying in plane P, face in a posterior direction directly toward the soft palate. In this way, the clear region created superior to plate P and below the hard palate communicates directly with the soft palate through posterior ports 596 so that vacuum applied through vacuum tube 592 is applied directly to the soft palate via posterior ports 596. Moreover, the vertical orientation of landing pad 584 and posterior ports 596 therein allows vacuum to be applied to the entire soft palate, from its free inferior tip to its posterior end where it attaches to the hard palate, enhancing the effectiveness of displacing the soft palate from the patient's airway. Because the patient's tongue is constrained under the inferior surface of plate 582, the tongue cannot be pulled by the vacuum forces to obstruct posterior ports 596. Inferior ports (not shown) may optionally be provided in plate 582 through which vacuum may be exerted upon the superior surface of the tongue, similar to the embodiment of FIGS. 14A-14D.

Figure 25:
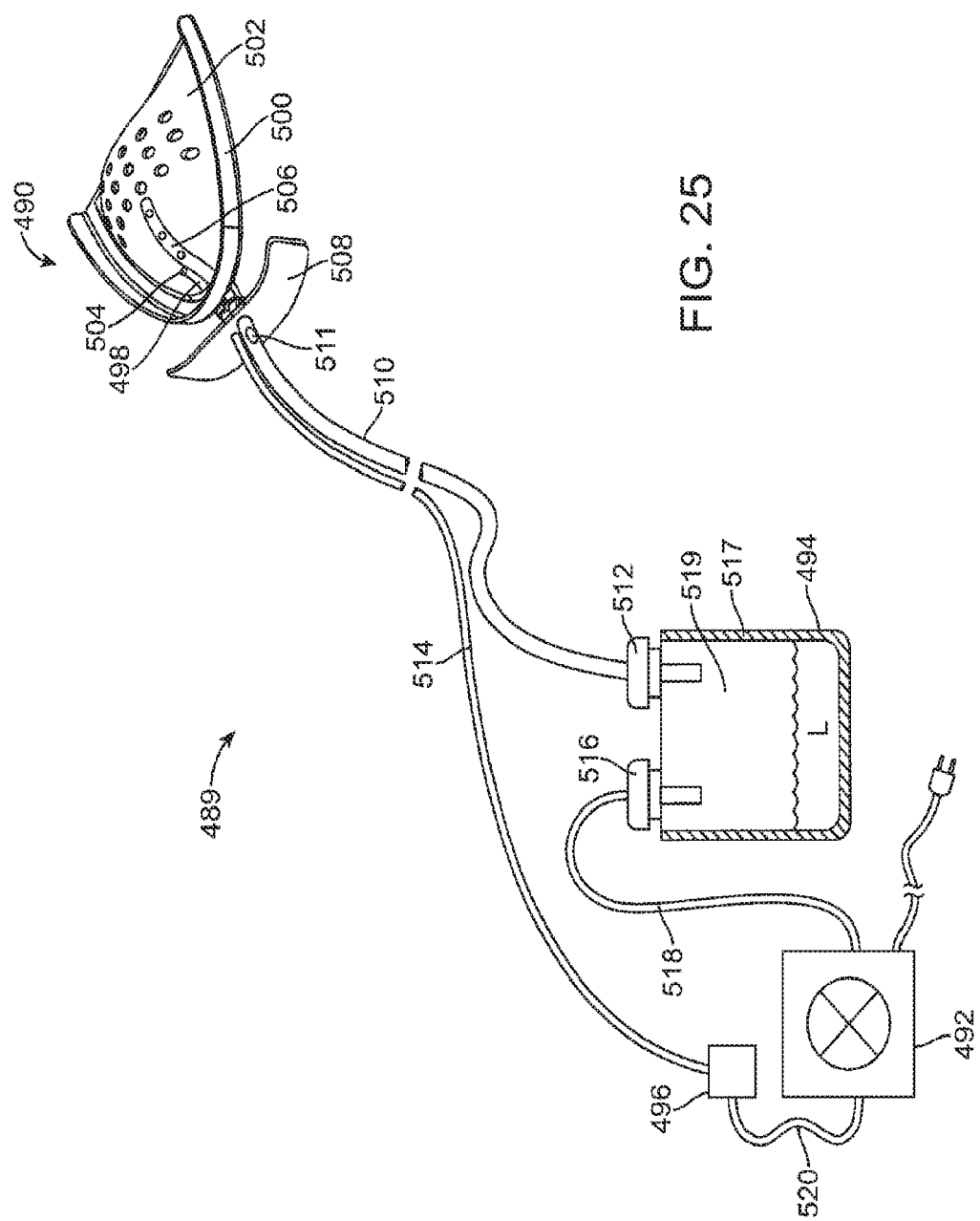
FIG. 25 is a schematic view of a system according to the invention in a further embodiment thereof.

FIG. 25 illustrates a further embodiment of a system 489 according to the invention including an oral device 490, a vacuum pump 492, a saliva reservoir 494, and a pressure sensor 496. Oral device 490 may be configured like any of the oral devices described above, such as oral device 280 of FIGS. 14A-14D. However, oral device 490 further includes a pressure conduit 498 extending through bite structure 500 to the superior side of tongue constraint 502 where pressure conduit 498 has a distal opening 504. It should be understood that pressure conduit 498 may alternatively comprise an inner lumen formed integrally within tongue constraint 502 or bite structure 500, and distal opening 504 could be positioned in any of various positions relative to bite structure 500 as may be desired to measure pressure within the oral cavity. A vacuum lumen 506 extends from the superior surface of tongue constraint 502 through bite structure 500 and both vacuum lumen 506 and pressure conduit 498 extend through lip seal 508. Vacuum lumen 506 is connected to a vacuum tube 510 which connects in an airtight manner to an input fitting 512 on saliva reservoir 494. Vacuum tube 510 has a vent hole 511 anterior to lip seal 508 so as to be outside the patient's oral cavity but positioned as close to oral device 490 as practicable while minimizing risk of obstruction by the patient's lips or other tissues. Alternatively vent hole 511 may be disposed in vacuum lumen 506 anterior to bite structure 500 or on the superior side of tongue constraint 502 so as to be located within the patient's oral cavity. When negative pressure is applied through vacuum lumen 506 within the patient's oral cavity, saliva or other liquids which collect may be aspirated through vacuum lumen 506 and vacuum tube 510. While removing excess liquids from the oral cavity is desirable, the weight of the liquid within vacuum tube 510 may create a pressure offset in vacuum tube 510 which would then affect the negative pressure applied within the oral cavity. System 489 alleviates this problem by providing vent hole 511 in vacuum tube 510, allowing any aspirated liquids to flow to saliva reservoir 494 more quickly.

Saliva reservoir 494 has an output fitting 516 which creates an airtight connection with an output tube 518 fluidly connected to vacuum pump 492. Saliva reservoir 494 has a liquid collector 517 which has an airtight interior and has sufficient depth to maintain liquid-free space 519 between the level of liquid L collected therein and the height of input fitting 512 and output fitting 516; in this way, negative pressure applied by vacuum pump 492 is exerted through the liquid-free space 519 within collector 517 and thus through vacuum tube 510. In an exemplary embodiment, collector 517 has an interior volume of about 20-1000 ml and will have an overall depth which exceeds the maximum liquid level expected to be collected in collector 517 over a typical 8 hour sleep cycle so that the liquid level does not rise to the level of fittings 512, 516. Saliva reservoir 494 may also contain a substance which absorbs, deodorizes, and/or sanitizes the saliva. In addition, saliva reservoir 494 may have a heating element to heat the saliva in order to evaporate or boil away excess volume.

Pressure lumen 498 is connected to a pressure tube 514 which connects to pressure sensor 496. Pressure sensor 496 is adapted to produce an electronic signal in response to the pressure sensed in pressure tube 514, and is electronically connected to vacuum pump 492 by a wire 520. Vacuum pump 492 has an electronic controller (not shown) responsive to signals received from pressure sensor 496, whereby the negative pressure applied by vacuum pump 492 may be regulated in a manner to maintain a desired level of negative pressure within the patient's oral cavity with oral device 490 in place. In this way, if the pressure within the oral cavity changes as a result of a loss of seal either in the lips or between the tongue and the soft palate, an excess of saliva aspirated through vacuum lumen 506, or other factors, pressure sensor 496 senses such change and vacuum pump 492 is automatically regulated to maintain the negative pressure at the desired level.

Figure 26:
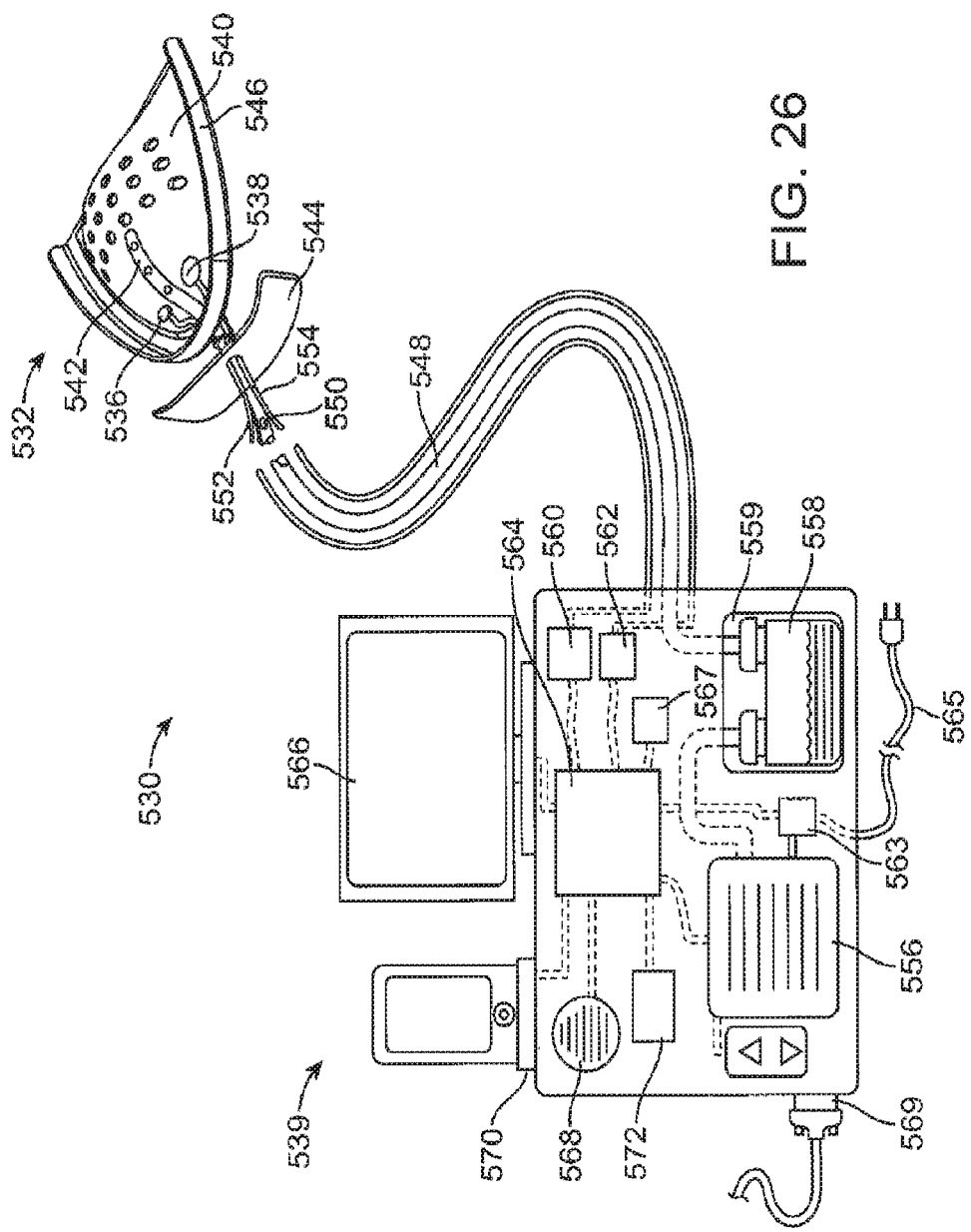
FIG. 26 is a schematic view of a system according to the invention in still another embodiment thereof.

A further embodiment of a system constructed in accordance with the invention is illustrated in FIG. 26. System 530 comprises an oral device 532 and a control unit 534. Oral device 532 may be configured as described in connection with in any of the other embodiments described herein, for example, oral device 280 of FIGS. 14A-14D. However, in this embodiment, oral device 532 further includes one or more sensors 536, 538 mounted thereon. Sensors 536, 538 may comprise any of a variety of sensors for detecting various physiological conditions within the oral cavity, including oximetry sensors for detecting oxygen levels in the oral cavity or in the blood within oral tissues, impedance sensors for detecting contact with the tongue or other tissues, accelerometers for detecting head position or orientation, thermistors for detecting temperature, microphones or piezoelectric sensors for detecting sounds or vibrations such as snoring or teeth grinding, or heartbeat, moisture sensors for detecting liquid or hydration of oral tissues, flow sensors for detecting air flow in the oral cavity or airway, or pressure sensors for detecting pressure within the oral cavity. The positions illustrated for sensors 536, 538 are merely exemplary and will be selected according to the type of sensor and the conditions being detected. For example, an impedance sensor for detecting contact with the patient's tongue could be mounted on the inferior side of tongue constraint 540 so as to directly contact the patient's tongue. A thermistor for detecting nasal air flow could be mounted on the superior side of vacuum lumen 542 anterior to lip seal 544 so as to be positioned directly under the patient's nostrils, thereby detecting the temperature (and presence) of exhaled air from the nostrils. Piezoelectric sensors for detecting teeth grinding could be mounted on bite structure 546 so as to be contacting or proximate to the teeth.

In a particular embodiment, sensor 536 comprises a pressure transducer for detecting pressure within the patient's oral cavity while sensor 538 comprises an oximetry sensor for detecting oxygen levels in the oral cavity or in surrounding tissues or blood therein. Detecting pressure within the oral cavity may be useful to detect whether a seal is being maintained between the tongue and soft palate such that the airway is isolated from the that portion of the oral cavity in which negative pressure is being applied via oral device 532. In addition, pressure data may be used to provide feedback to the vacuum pump applying such negative pressure in order to automatically regulate and maintain the level of negative pressure being applied, as described above in connection with FIG. 25. Oximetry sensor 538 is preferably a pulse oximetry sensor for detecting oxygen saturation levels in the oral cavity or in the tissues surrounding the oral cavity such as the tongue, cheeks, gums, or hard or soft palates. Oxygen levels in the blood or in the oral cavity may be detected to determine whether the patient is receiving adequate oxygen during sleep, i.e., whether the patient's airway is unobstructed.

Vacuum lumen 542 extends through lip seal 544 and connects, preferably through a detachable fitting (not shown), to a vacuum tube 548 having a vent hole 550 as in the embodiment of FIG. 25. A pressure lead 552 is coupled to pressure transducer 536 and extends through lip seal 544 to control unit 530. An oximeter lead 554 is coupled to oximetry sensor 538 and extends through lip seal 544 to control unit 530. Preferably pressure lead 552 and oximeter lead 554 have detachable couplings (not shown) anterior to lip seal 544 to allow detachment of oral device 532 from control unit 530.

Control unit 534 includes a vacuum pump 556 the output (suction) orifice of which is fluidly coupled to a saliva reservoir 558 constructed and operated as described above in connection with FIG. 25. Preferably, control unit 534 has an opening 559 through which saliva reservoir 558 may be removed and emptied. Vacuum tube 548 connects to control unit 530 in which it is fluidly connected to saliva reservoir 558. Vacuum pump 556 is connected to a power supply 563 which connects to an AC power source via cord 565. The speed and/or pressure of vacuum pump 556 may be manually controlled by a switch 561 electrically coupled to vacuum pump 556 or to power supply 563.

Pressure lead 552 is coupled to a pressure sensor interface 560 and oximeter lead 554 is coupled to an oximeter sensor interface 562. Pressure sensor interface 560 and oximeter sensor interface 562 are each connected to a computerized controller 564. Controller 564 is adapted to receive signals generated by pressure signal generator 560 and oximeter signal generator 562, process those signals, and electronically control vacuum pump 556 to regulate the negative pressure being applied therewith and thereby optimize device performance and the physiologic condition of the patient. Preferably, so long as oxygen levels detected by oximetry sensor 538 are satisfactory, controller 564 will regulate vacuum pump 556 to maintain constant pressure as measured by pressure transducer 536. However, if the detected oxygen reaches an unacceptably low level, controller 564 may be adapted to automatically boost pump speed to increase the level of negative pressure being applied via oral device 532. Computerized controller 564 will include a central processing unit (CPU) and will be connected to a memory device 567 which may comprise a fixed read only memory device and/or random access memory device, and optionally a removable memory device such as a flash drive, optical disk, or other removable data storage medium. Data collected from sensors 536, 538, as well as system performance data and other information may be saved in memory device 567 and recalled by controller 564.

Additional optional components of control unit 534 include an electronic display 566, audio speaker 568, a docking station 570 suitable for iPhone, iPod or other portable device, a wireless transceiver (e.g. Bluetooth) or modem 572, a data connector 569 for connection to data cables from other computerized devices, and saliva level sensor (not shown) in saliva reservoir 558, each being electrically coupled to controller 564. Display 566 displays information output to the user from controller 564 including information regarding pressure readings, oximetry readings, data from any other sensors on oral device 532, current pump speed or outlet pressure, sensor readings over a desired time period, messages or reminders to the user, indications that vacuum tube 548 is clogged or saliva reservoir 558 is full, and other pertinent information. Control unit 534 preferably includes a user input device to allow the user to input commands and other information. Display 566 may be a touchscreen display or a separate keyboard (not shown) may be coupled to controller 564. Speaker 568 may similarly provide information to the user including alerts or alarms, e.g. that the pressures are not being maintained or oxygen levels are too low, as well as playing music or other sounds to help the patient sleep or to wake at a desired time. Logged data, saved in memory device 567, may be output to display 566, to a portable device via docking station 570, or to another device via data connector 569 or wireless transmitter/modem 572. Control unit 534 is preferably programmable such that the user may select the amount of negative pressure applied, the length of time it is to be applied, alarms to triggered, data to be recorded and logged, and other parameters, according to conditions detected in the oral cavity by sensors 536, 538, time of day, or other factors. Control unit 534 may also employ software to allow it to calculate and automatically select suitable operating parameters based on personal health information input by the user.

In other alternative embodiments, the oral device of the invention may include features to treat other conditions during sleep along with sleep apnea. For example, the oral device of the invention may include a bite structure like bite structure 284 of FIGS. 14A-14D which is adapted to apply forces to the patient's teeth to straighten the teeth gradually over time, similar to orthodontic appliances. The bite structure may be custom molded to the patient's teeth and periodically replaced with structures of gradually altered shapes to gently move the teeth into a desired position. Optionally, the bite structure may be detachable from the tongue constraint and vacuum lumen(s) to allow for easy replacement of various bite structures. In another alternative embodiment, the bite structure may be adapted to reduce bruxism, or teeth grinding, while the oral device of the invention is being used to maintain airway patency.

As a further optional feature, the bite structure of the oral device may be adapted to retain bleaching agents or other cosmetic or therapeutic materials in contact with the patient's teeth while the oral device is being worn. The bite structure may again have the U-shaped configuration of bite structure 284 of FIGS. 14A-14D, and may be custom molded to fit closely around the patient's top teeth. A separate bleaching tray of conventional design could be used for the bottom teeth, or optionally the bite structure could be configured to fit around both the top and bottom teeth so that the agents could be applied to both with the same device. The bite structure will be continuous and free of holes or voids throughout the area where the agent is to be applied so that the agent does not leak out while the device is being worn.

The invention may further be utilized in conjunction with other apparatus for the treatment of sleep apnea. For example, oral devices and systems described herein may be used in conjunction with a conventional CPAP apparatus for delivering air under positive pressure to the nasal airway. In this way, with the device of the invention applying negative pressure within the oral cavity, and the CPAP apparatus increasing pressure in the airway, the pressure gradient between the airway and the oral cavity is further increased, thus urging the soft palate and tongue anteriorly out of the airway.

In addition the devices and systems of the invention may be used in conjunction with one-way nasal valve devices, such as those described in, for example, U.S. patent application Ser. No. 11/941,915, filed Nov. 16, 2007, and Ser. No. 11/811,339, filed Jun. 7, 2007, which are hereby incorporated herein by reference. Again, by increasing airway pressure using such nasal valve devices while decreasing pressure in the oral cavity using the present invention, the pressure gradient from airway to oral cavity is increased, thus urging the soft palate and tongue out of the airway.

While the above is a complete description of the preferred embodiments of the invention, various alternatives, modifications, substitutions, and equivalents may be used. Therefore, the above description should not be taken as limiting the scope of the invention, which is defined by the appended claims.

What is claimed is:

1. A method for improving airway patency in a patient having an oral cavity, a hard palate, a soft palate, a tongue, lips, and an airway, said method comprising: constraining a medial surface of the patient's tongue with a tongue constraint of an oral device placed in the oral cavity to generate a clear region between the medial surface and the hard palate, the clear region being in fluid communication with the soft palate, and the tongue constraint having superior surface and inferior surfaces configured to generate the clear region; and applying a negative pressure within the oral cavity to hold the soft palate in a position in which the airway is at least partially open, the negative pressure being applied through one or more ports of the oral device, the one or more ports remaining unobstructed by the tongue when the negative pressure is applied, wherein the applied negative pressure causes the soft palate and tongue form a seal whereby the patient's airway is substantially fluidly isolated from the clear region.

2. A method as in claim 1, wherein constraining the medial surface of the patient's tongue comprises engaging only a middle portion of the tongue with the oral device while leaving lateral areas of the tongue unconstrained.

3. A method as in claim 1, wherein applying the negative pressure comprises applying the negative pressure through a posterior port of the one or more ports facing away from the tongue so that the posterior port remains unblocked by the tongue.

4. A method as in claim 1, further comprising sealing the lips to inhibit air entering the oral cavity.

5. A method as in claim 1, further comprising positioning a lip seal coupled to the oral device between the lips and teeth of the patient to seal the lips to inhibit leaks into the oral cavity and to inhibit movement of the oral device positioned in the oral cavity.

6. A method as in claim 1, wherein applying the negative pressure comprises applying the negative pressure through a lumen integral with or coupled to the oral device.

7. A method as in claim 1, applying the negative pressure comprises applying the negative pressure with an inferior port of the one or more ports facing toward a superior surface of the tongue.

8. A method as in claim 1, wherein constraining the medial surface of the patient's tongue comprises engaging the medial surface of the tongue with the oral device at a point at least ⅓ of the distance from an anterior tip of the tongue to a posterior end of the tongue.

9. A method as in claim 1, further comprising monitoring a pressure in the oral cavity as the negative pressure is applied.

10. A method as in claim 1, further comprising monitoring blood oxygenation of the patient as the negative pressure is applied.

11. A method as in claim 1, applying the negative pressure comprises applying the negative pressure with a lateral port of the one or more ports facing toward a lateral surface of the tongue.

12. A method as in claim 1, applying the negative pressure comprises coupling a vacuum source to the oral device to be in fluid communication with the one or more ports of the oral device.

13. A method as in claim 1, wherein the negative pressure is in the range from −5 cm $H_2O$ to −150 cm $H_2O$.

14. A method as in claim 1, further comprising collecting saliva aspirated from the oral cavity by the negative pressure.

15. A method as in claim 1, wherein the clear region is defined between the superior and inferior surfaces of the oral device.

16. A method as in claim 1, wherein tongue constraint comprises a tube.

17. Apparatus for improving airway patency of a patient having an oral cavity, a hard palate, a soft palate, a tongue, lips, and an airway, the apparatus comprising: an oral device positionable in the oral cavity, the oral device comprising one or more ports through which negative pressure is applied to provide a continuous pathway for pressure delivery from the lips to the soft palate when the oral device is placed in the oral cavity, wherein the oral device is configured to apply negative pressure to generate a seal between the soft palate and a posterior region of the tongue to isolate the airway from the oral cavity, and wherein the oral device comprises a tongue constraint having a superior surface and an inferior surface, the surfaces being configured to maintain a clear region between a medial region of the tongue and the hard palate.

18. An apparatus as in claim 17, wherein the oral device is configured to provide a continuous air flow path from the lips to the soft palate when the oral device is placed in the oral cavity.

19. An apparatus as in claim 18, wherein the continuous air flow path comprises an air flow lumen integral with or coupled to the oral device.

20. An apparatus as in claim 17, wherein the tongue constraint is configured to engage only a middle portion of the tongue with lateral areas of the tongue remaining unconstrained.

21. An apparatus as in claim 17, wherein the one or more ports comprises a posterior port facing away from the tongue so as to remain unblocked by the tongue when the negative pressure is applied.

22. An apparatus as in claim 17, further comprising a lip seal positionable between the lips and teeth of the patient, the lip seal being configured to seal the lips to inhibit leaks into the oral cavity.

23. An apparatus as in claim 17, wherein the one or more ports comprise an inferior port in fluid communication with the oral cavity and configured to apply the negative pressure to a superior surface of the tongue.

24. An apparatus as in claim 17, wherein the tongue constraint is configured to engage the medial surface at a point at least ⅓ of the distance from an anterior tip of the tongue to a posterior end of the tongue.

25. An apparatus as in claim 17, wherein the clear region is defined between the superior and inferior surfaces of the tongue constraint.

26. An apparatus as in claim 17, further comprising a pressure monitor coupled to the oral device.

27. An apparatus as in claim 17, further comprising an oximetry sensor coupled to the oral device.

28. An apparatus as in claim 17, wherein the one or more ports comprise a lateral port configured to apply the negative pressure to a lateral surface of the tongue.

29. An apparatus as in claim 17, further comprising a negative pressure source connectable to the oral device in fluid communication with the continuous air flow path.

30. An apparatus as in claim 17, further comprising a saliva collector or absorber connectable to the oral device to collect or absorb saliva aspirated from the oral cavity by the negative pressure.

31. An apparatus as in claim 17, wherein tongue constraint comprises a tube.

* * * * *